US007994124B2

(12) United States Patent
Cox

(10) Patent No.: US 7,994,124 B2
(45) Date of Patent: Aug. 9, 2011

(54) METHODS OF USE OF G-CSF CYSTEINE MUTEINS

(75) Inventor: George N. Cox, Louisville, CO (US)

(73) Assignee: Bolder Biotechnology, Inc., Boulder, CO (US)

(*) Notice: Subject to any disclaimer, the term of this patent is extended or adjusted under 35 U.S.C. 154(b) by 0 days.

(21) Appl. No.: 12/610,891

(22) Filed: Nov. 2, 2009

(65) Prior Publication Data

US 2010/0266529 A1 Oct. 21, 2010

Related U.S. Application Data

(60) Continuation of application No. 11/857,399, filed on Sep. 18, 2007, now abandoned, which is a continuation of application No. 10/685,288, filed on Oct. 13, 2003, now Pat. No. 7,270,809, which is a continuation of application No. 10/400,377, filed on Mar. 26, 2003, now Pat. No. 7,148,333, which is a division of application No. 09/462,941, filed as application No. PCT/US98/14497 on Jul. 13, 1998, now Pat. No. 6,608,183, said application No. 10/685,288 is a continuation-in-part of application No. 10/298,148, filed on Nov. 15, 2002, now Pat. No. 7,153,943, and a continuation-in-part of application No. 09/462,941, filed on Jan. 14, 2000, now Pat. No. 6,608,183, said application No. 10/685,288 is a continuation-in-part of application No. 09/889,273, filed as application No. PCT/US00/00931 on Jan. 14, 2000, now Pat. No. 6,753,165, said application No. 10/685,288 is a continuation-in-part of application No. 10/276,358, filed as application No. PCT/US01/16088 on May 16, 2001, now Pat. No. 7,306,931.

(60) Provisional application No. 60/418,106, filed on Oct. 11, 2002, provisional application No. 60/052,516, filed on Jul. 14, 1997, provisional application No. 60/418,040, filed on Oct. 11, 2002, provisional application No. 60/332,285, filed on Nov. 15, 2001, provisional application No. 60/116,041, filed on Jan. 14, 1999, provisional application No. 60/204,617, filed on May 16, 2000, provisional application No. 60/418,105, filed on Oct. 11, 2002.

(51) Int. Cl.
A61K 38/19 (2006.01)
A61K 39/00 (2006.01)
A61K 38/00 (2006.01)

(52) U.S. Cl. .................. 514/7.6; 424/198.1; 514/3.2
(58) Field of Classification Search .................. None
See application file for complete search history.

(56) References Cited

U.S. PATENT DOCUMENTS

| 4,588,585 A | 5/1986 | Mark et al. |
| 4,636,463 A | 1/1987 | Altman et al. |
| 4,678,751 A | 7/1987 | Goeddel |
| 4,738,844 A | 4/1988 | Bell et al. |
| 4,751,077 A | 6/1988 | Bell et al. |
| 4,810,643 A | 3/1989 | Souza |
| 4,855,238 A | 8/1989 | Gray et al. |
| 4,904,584 A | 2/1990 | Shaw |
| 4,921,699 A | 5/1990 | DeChiara et al. |
| 4,929,554 A | 5/1990 | Goeddel et al. |
| 5,096,705 A | 3/1992 | Goeddel et al. |
| 5,153,265 A | 10/1992 | Shadle et al. |
| 5,162,111 A | 11/1992 | Grabstein et al. |
| 5,166,322 A | 11/1992 | Shaw et al. |
| 5,178,855 A | 1/1993 | Bonnem |
| 5,206,344 A | 4/1993 | Katre et al. |
| 5,208,158 A | 5/1993 | Bech et al. |
| 5,214,132 A | 5/1993 | Kuga et al. |
| 5,223,407 A | 6/1993 | Wong et al. |
| 5,229,496 A | 7/1993 | Deeley et al. |
| 5,382,657 A | 1/1995 | Karasiewicz et al. |
| 5,391,485 A | 2/1995 | Deeley et al. |
| 5,393,870 A | 2/1995 | Deeley et al. |
| 5,441,734 A | 8/1995 | Reichert et al. |
| 5,574,137 A | 11/1996 | Gray et al. |
| 5,578,301 A | 11/1996 | Myers |
| 5,582,824 A | 12/1996 | Goeddel et al. |
| 5,595,888 A | 1/1997 | Gray et al. |
| 5,602,007 A | 2/1997 | Dunn et al. |
| 5,629,283 A | 5/1997 | Nicola et al. |
| 5,681,720 A | 10/1997 | Kuga et al. |
| 5,690,925 A | 11/1997 | Gray et al. |
| 5,720,952 A | 2/1998 | Clark et al. |
| 5,766,897 A | 6/1998 | Braxton |
| 5,824,778 A | 10/1998 | Ishikawa et al. |
| 5,824,784 A | 10/1998 | Kinstler et al. |
| 5,849,535 A | 12/1998 | Cunningham et al. |
| 5,891,429 A | 4/1999 | Clark et al. |

(Continued)

FOREIGN PATENT DOCUMENTS

CA 2066370 4/1996

(Continued)

OTHER PUBLICATIONS

Walter M.R. et al. Crystal structure of a complex between interferon-gamma and its soluble high-affinity receptor. Nature. 2000. vol. 376, p. 230-235.
Watson JD-Molecular Biology of the gene, third edition, WA Benjamin, eds. ISBN 0-8053-9609-8, p. 367, 1977.
U.S. Appl. No. 12/001,639, filed Dec. 11, 2007, Rosendahl et al.
U.S. Appl. No. 12/391,896, filed Feb. 24, 2009, Cox.
U.S. Appl. No. 12/502,839, filed Jul. 14, 2009, Cox et al.
U.S. Appl. No. 12/604,165, filed Oct. 22, 2009, Cox.
Abdel-Meguide et al., "Three dimensional structure of a genetically engineered variant of porcine growth hormone", 1987, PNAS, vol. 84, pp. 6434-6437.

(Continued)

Primary Examiner — Elly-Gerald Stoica
(74) Attorney, Agent, or Firm — Sheridan Ross P.C.

(57) ABSTRACT

The present invention relates to therapeutic methods for a protecting an animal from a disease or condition that can be treated by granulocyte colony-stimulating factor (G-CSF) wherein a composition comprising a cysteine variant of G-CSF is provided. Also disclosed herein are preferred cysteine variants of G-CSF for use in the composition.

28 Claims, No Drawings

U.S. PATENT DOCUMENTS

| | | | |
|---|---|---|---|
| 5,895,646 | A | 4/1999 | Wang |
| 5,908,621 | A | 6/1999 | Glue et al. |
| 5,908,763 | A | 6/1999 | Clark et al. |
| 5,916,773 | A | 6/1999 | Mele et al. |
| 5,942,221 | A | 8/1999 | Clark et al. |
| 6,042,822 | A | 3/2000 | Gilbert et al. |
| 6,171,824 | B1 | 1/2001 | Todaro et al. |
| 6,177,074 | B1 | 1/2001 | Glue et al. |
| 6,250,469 | B1 | 6/2001 | Kline |
| 6,287,557 | B1 | 9/2001 | Boursnell et al. |
| 6,323,006 | B1 | 11/2001 | Peregrino Ferreira et al. |
| 6,362,162 | B1 | 3/2002 | Rybak et al. |
| 6,461,605 | B1 | 10/2002 | Cutler et al. |
| 6,472,373 | B1 | 10/2002 | Albrecht |
| 6,497,871 | B1 | 12/2002 | Gray et al. |
| 6,514,729 | B1 | 2/2003 | Bentzien |
| 6,524,570 | B1 | 2/2003 | Glue et al. |
| 6,531,122 | B1 | 3/2003 | Pedersen et al. |
| 6,608,183 | B1 | 8/2003 | Cox, III |
| 6,632,426 | B2 | 10/2003 | Osslund |
| 6,753,165 | B1 | 6/2004 | Cox et al. |
| 6,780,613 | B1 | 8/2004 | Wells et al. |
| 6,800,740 | B1 | 10/2004 | Cunningham et al. |
| 7,038,015 | B2 | 5/2006 | Jensen |
| 7,148,333 | B2 | 12/2006 | Cox, III |
| 7,153,943 | B2 | 12/2006 | Cox, III et al. |
| 7,214,779 | B2 | 5/2007 | Cox, III |
| 7,232,885 | B2 | 6/2007 | Cox, III |
| 7,253,267 | B2 | 8/2007 | Cox, III |
| 7,270,809 | B2 | 9/2007 | Cox, III |
| 7,306,931 | B2 | 12/2007 | Rosendahl et al. |
| 7,309,781 | B2 | 12/2007 | Cox, III |
| 7,314,921 | B2 | 1/2008 | Cox, III |
| 7,345,149 | B2 | 3/2008 | Cox, III |
| 7,345,154 | B2 | 3/2008 | Cox, III |
| 7,399,839 | B2 | 7/2008 | Cox et al. |
| 7,495,087 | B2 | 2/2009 | Cox, III |
| 7,629,314 | B2 | 12/2009 | Cox, III |
| 2003/0166865 | A1 | 9/2003 | Cox, III |
| 2004/0136955 | A1 | 7/2004 | Barker et al. |
| 2004/0230040 | A1 | 11/2004 | Cox, III |
| 2005/0214254 | A1 | 9/2005 | Cox, III |
| 2007/0253929 | A1 | 11/2007 | Cox, III |
| 2008/0076706 | A1 | 3/2008 | Cox |
| 2008/0219950 | A1 | 9/2008 | Cox |
| 2008/0317713 | A1 | 12/2008 | Cox |
| 2009/0060863 | A1 | 3/2009 | Cox |

FOREIGN PATENT DOCUMENTS

| | | |
|---|---|---|
| CA | 2287521 | 10/1998 |
| EP | 0185459 | 6/1986 |
| EP | 0243153 | 10/1987 |
| EP | 0312358 | 4/1989 |
| EP | 0355460 | 2/1990 |
| EP | 0458064 | 11/1991 |
| EP | 0612846 | 8/1994 |
| EP | 0668354 | 8/1995 |
| JP | 02-234692 | 9/1990 |
| JP | 04-164098 | 9/1992 |
| JP | 4-507099 | 12/1992 |
| JP | 5-268983 | 10/1993 |
| JP | 6-510904 | 12/1994 |
| JP | 9-503396 | 4/1997 |
| JP | 10-507080 | 7/1998 |
| WO | WO 86/05804 | 10/1986 |
| WO | WO 87/01132 | 2/1987 |
| WO | WO 90/12874 | 11/1990 |
| WO | WO 90/13310 | 11/1990 |
| WO | WO 93/00109 | 1/1993 |
| WO | WO 93/06217 | 4/1993 |
| WO | WO 94/01453 | 1/1994 |
| WO | WO 94/12219 | 6/1994 |
| WO | WO 94/12638 | 6/1994 |
| WO | WO 94/12639 | 6/1994 |
| WO | WO 94/22466 | 10/1994 |
| WO | WO 95/11987 | 5/1995 |
| WO | WO 95/32003 | 11/1995 |
| WO | WO 95/034326 | 12/1995 |
| WO | WO 96/04385 | 2/1996 |
| WO | WO 96/11949 | 4/1996 |
| WO | WO 96/31537 | 10/1996 |
| WO | WO 96/36362 | 11/1996 |
| WO | WO 97/11370 | 3/1997 |
| WO | WO 98/25971 | 6/1998 |
| WO | WO 98/37200 | 8/1998 |
| WO | WO 99/03887 | 1/1999 |
| WO | WO 00/42175 | 7/2000 |
| WO | WO 01/87925 | 11/2001 |
| WO | WO 02/44717 | 6/2002 |

OTHER PUBLICATIONS

Alberts et ai, The birth, assembly and death of proteins. Chapter 5 in Molecular biology of the cell, Third edition, Garland Publishing, Inc. New York, NY, 1994; ISBN 0-8153-1619-4.

Barton et al., "Identification of Three Distinct Receptor Binding Sites of Murine Interleukin-11" The Journal of Biological Chemistry, vol. 274 No. 9, pp. 5755-5761 (Feb. 1999).

Bazan et al., "Unraveling the Structure of IL-2" Science, vol. 257 No. 5068, pp. 410-413 (Jul. 1992).

Bazan, "Haemopoietic receptors and helical cytokines" Immunology Today, 11:350-354 (1990).

Beilharz et al., "Antiviral and Antiproliferative Activities of Interferon-$\alpha$1: The Role of Cysteine Residues" J. Interferon Res., 6:677-685 (1986).

Bill et al., "Expression and mutagenesis of recombinant human and murine erythropoietins in *Escherichia coli*" Biochimica et Biophysica Acta, 1261: 34-43 (1995).

Bittorf et al., "Structural and functional characterisation of recombinant human erythropoietin analogues" Febs. Lett., 366: 133-136 (1993).

Black RJ, "Animal Studies of Prophylaxis" Am. J. Med. 102 39-44 (1997).

Boissel et al., "Erythropoietin Structure-Function Relationships" J. Biol. Chem., 268(21):15983-15993 (1993).

Bowie et al., "Deciphering the Message in Protein Sequences: Tolerance to Amino Acid Substitutions" Science, vol. 247 No. 4948, pp. 1306-1310 (Mar. 1990).

Campbell et al., "Pegylated peptides V" J. Peptide Res., 49:527-537 (1997).

Cantrell et al., "Cloning, sequence, and expression of a human granulocyte/macrophage colony-stimulating factor." Proceedings of the National Academy of Sciences, USA, vol. 82 No. 18, pp. 6250-6254 (1985).

Cheetham et al., "NMR structure of human erythropoietin and a comparison with its receptor bound conformation" Nat. Structural Biol., 5: 861-866 (1998).

Cheetham et al., "Structure-function studies of human interferons-$\alpha$: enhanced activity on human and murine cells", Antiviral Research 15 (1991) 27-40.

Chene et al. "Crystallization of the Complex of Human IFN-gamma and the Extracellular Domain of the IFN-gamma Receptor."Proteins: Structure, Function, and Genetics: 23:591-594 (1995).

Chern et al, "Structural role of amino acids 99-110 in recombinant human erythropoietin", European Journal of Biochemistry, vol. 202 No. 2, pp. 225-229 (Dec. 1991).

Clark et al., "Long-acting Growth Hormones Produced by Conjugation with Polyethylene Glycol" J. Biol. Chem., 271 (36):21969-21977 (1996).

Clark-Lewis et al., "Structure-function studies of human granulocyte-macrophage colony-stimulating factor. Identification of residues required for activity" Journal of Immunology, vol. 141 No. 3, pp. 881-889 (Aug. 1988).

Cosenza et al. "Disulfide Bond Assignment in Human Interleukin-7 by Matrix-assisted Laser Desorption/Ionization Mass Spectroscopy and Site-directed Cysteine to Serine Mutational Analysis" The Journal of Biological Chemistry, vol. 272, No. 52, Issue of Dec. 26, pp. 32995-33000, 1997.

Cox et al., "A long acting mono-pegylated human growth hormone analog is a potent stimulator of weight gain and bone growth in hypophysectiomized rates", 2007, Endocrinology, vol. 148, Issue 4, pp. 1590-1597.

Cunningham BC, Wells JA. "High-Resolution Epitope Mapping of hGH-Receptor Interactions by Alanine-Scanning Mutagenesis" Science. 244:1081-5, (1989).

Cunningham et al., "Receptor and Antibody Epitopes in Human Growth Hormone Identified by Homolog-Scanning Mutagenesis" Science, 243:1330-1336 (1989).

Czupryn et al. "Alanine-scanning Mutagenesis of Human Interleukin-11: Identification of Regions Important for Biological Activity" Annals of the New York Academy of Sciences, vol. 762, pp. 152-164 (Jul. 1995).

Czupryn et al., "Structure-Function Relationships in Human Interleukin-11" Journal of Biological Chemistry, vol. 270 No. 2, pp. 978-985 (Jan. 1995).

DeChiara, T.M. et al., "Procedures for in Vitro DNA Mutagenesis of Human Leukocyte Interferon Sequences." Methods in Enzymology, vol. 119(58). pp. 403-415. (1986).

Diederichs et al., "Novel fold and putative receptor binding site of granulocyte-macrophage colony-stimulating factor." Science, vol. 254 No. 5039, pp. 1779-1782 (1991).

Dube et al., "Glycosylation at Specific Sites of Erythropoietin Is Essential for Biosynthesis, Secretion, and Biological Function" The Journal of Biol. Chem., vol. 263, No. 33: 17516-17521, 1988.

Edge et al., "Interferon Analogues from Synthetic Genes: An Approach to Protein Structure-Activity Studies", Interferon, vol. 7, pp. 1-46, 1986.

Elliot et al., "Mapping of the Active Site of Recombinant Human Erythropoietin" Blood, 89:493-502 (1997).

Evinger et al., "Recombinant Human Leukocyte Interferon Produced in Bacteria Has Antiproliferative Activity" J. Biol. Chem. 256(5):2113-2114 (1981).

Fibi et al., "Evidence for the Location of the Receptor-Binding Site of Human Erythropoietin at the Carboxyl-Terminal Domain", Blood, vol. 77, No. 6, Mar. 15, 1991; pp. 1203-1210.

Fujii et al., "Structure of KW-2228, a tailored human granulocyte colony-stimulating factor with enhanced biological activity and stability", FEBS Lett. 410: 131-5, 1997.

Ganser et al., "The effect of recombinant human granulocyte-macrophage colony-stimulating factor on neutropenia and related morbidity in chronic severe neutropenia" Annals of Internal Medicine, vol. 111 No. 11, pp. 887-892 (Dec. 1989).

Goodson and Katre, "Site-Directeed Pegylation of Recombinant Interleukin-2 at its Glycosylation Site" Bio/Technology, 8:343-346 (1990).

Goodwin et al. "Human interleukin 7: Molecular cloning and growth factor activity on human and murine B-lineage cells" Proc. Natl. Acad. Sci. USA, vol. 86, pp. 302-306, Jan. 1989.

Grodberg et al., "Alanine scanning mutagenesis of humna erythropoietin identifies four amino acids which are critical for biological activity", European Journal of Biochemistry, vol. 218, No. 2, pp. 597-601 (1993).

Harmegnies et al., Characterization of a potent human interleukin-11 agonist, 2003, Biochemical Journal, vol. 375, pp. 23-32.

Hill et al., "The structure of granulocyte-colony-stimulating factor and its relationship to other growth factors" Proc. Natl. Acad. Sci. USA, 90:5167-5171 (1993).

Hu et al., "Human IFN-α Protein Engineering: The Amino Acid Residues at Positions 86 and 90 Are Important for Antiproliferative Activity" Journal of Immunology. 167:1482-1489 (2001).

Karpusas et al., The crystal structure of human interferon β at 2.2-Å resolution Proc. Natl. Acad. Sci. USA, 94:11813-11818 (1997).

Karpusas et al., "The structure of human interferon-beta: implications for activity", Cell. Mol. Life sci., 54, p. 1203-1216, 1998.

Kawashima et al., "Molecular cloning of cDNA encoding adipogenesis inhibitory factor and identity with interleukin-11" FEBS Letters, vol. 283 No. 2, pp. 199-202 (Jun. 1991).

Knulsi et al., "Polyethylene glycol (PEG) modification of granulocyte-macrophage colony stimulating factor (GM-CSF) enhances neutrophil priming activity but not colony stimulating activity" British Journal of Haematology, vol. 82 No. 4, pp. 654-663 (1992).

Kroemer et al. Prediction of three-dimensional structure of IL-7 by homology modeling, Protein Engineering, 9,493-498, 1996.

Kuga et al., "Mutagenesis of human granulocyte colony stimulating factor" Biochem Biophys Res Commun. 159: 103-11, 1989.

Lee et al., "Isolation of cDNA for a human granulocyte-macrophage colony-stimulating factor by functional expression in mammalian cells" Proceedings of the National Academy of Sciences, USA, vol. 82 No. 13, pp. 4360-4364 (1985).

Lin et al., "Cloning and expression of the human erythropoietin gene", Proceedings of the National Academy of Sciences, USA, vol. 82 No. 22, pp. 7580-7584 (Nov. 1985).

Lowman and Wells, "Affinity Maturation of Human Growth Hormone by Monovalent Phage Display" J. Mol. Biol., 234:564-578 (1993).

Lydon et al., "Immunochemical Mapping of α-2 Interferon", Biochemistry 1985, 24, 4131-4141.

Matthews et al., "A sequential dimerization mechanism for erythropoietin receptor activation" PNAS, 93: 9471-9476 (1996).

Miyadi et al., "Importance of the Carboxy-terminus of Human Interleukin-11 in Conserving Its Biological Activity" Bioscience, biotechnology, and biochemistry, vol. 60 No. 3, pp. 541-542 (Mar. 1996).

Mori et al., "Recombinant human granulocyte-macrophage colony-stimulating factor (rhGM-CSF) and rhG-CSF in the treatment of a child with severe chronic neutropenia" Blood, vol. 84 No. 9, pp. 3244-3245 (Nov. 1994).

Mott and Campbell, "Four-helix bundle growth factors and their receptors: protein-protein interactions" Curr Opin Struct Biol, 5:114-121 (1995).

Nagata S., Cytokine Handbook, chapter 20, p. 371-385, ISBN 0-12-689661-5, Thomson A Wed., Academic Press, Harocurt Brace & Co. publishers, London, San Diego, New York, Boston, Sydney, Tokyo, Toronto, 1994.

Nielson et al., "Erythropoietin-beta-D-galactosidase. The generation, purification and use of a fusion protein", Journal of Immunological Methods, vol. 111, No. 1, pp. 1-9 (Jun. 1988).

Nisbet et al., "Single Amino Acid Substitutions at Conserved Residues of Human Interferon-α Can Effect Antiviral Specific Activity" Biochem. Int., 11:301-309 (1985).

Olins P.O. et al: 'Saturation muatgenesis of human interleukin-3' Journal of Biological Chemistry vol. 270, No. 40, Oct. 6, 1996, pp. 23754-23760.

Paul et al., "Molecular cloning of a cDNA encoding interleukin 11, a stromal cell-derived lymphonpoietic and hematopoietic cytokine" Proceedings of the National Academy of Sciences, USA, vol. 87, No. 19, pp. 7512-7516 (Oct. 1990).

Quelle, "Phosphorylatable and epitope-tagged human erythropoietins: utility and purification of native baculovirus-derived forms" Protein Expr Purif, Dec. 1992; 3(6); 461-9, PubMed Abstract only, PMID 1283094.

Radhakrishnan et al., "Zinc mediated dimer of human interferon-α2b revealed by X-ray crystallography" Structure, 4(12):1453-1463 (1996).

Rozwarski et al., "Refined crystal structure and mutagenesis of human granulocyte-macrophage colony-stimulating factor." Proteins, vol. 26 No. 3, pp. 304-313 (Nov. 1996).

Senda et al., "Refined crystal structure of recombinant murine interferon-beta at 2.15 A resolution.", J. Mol. Biol., 1995, vol. 253, pp. 187-207.

Shanafelt et al., "Identification of critical regions in mouse granulocyte-macrophage colony-stimulating factor by scanning-deletion analysis" Proceedings of the National Academy of Sciences, USA, vol. 86, pp. 4872-4876 (1989).

Sprang and Bazan, "Cytokine structural taxonomy and mechanisms of receptor engagement" Curr. Opin. Struct. Biol., 3:815-827 (1993).

Syed et al., "Efficiency of sinalling through ecytokine receptors depends critically on receptor orientation" Nature, 395:511-516, (1998).

Sytkowski et al, "Immunoshemical studies of human erythropoietin using site-specific anti-peptide antibodies", Journal of Biological Chemistry, vol. 262, No. 3, pp. 1161-1165 (1987).

Sytkowski et al., "Human erythropoietin dimers with markedly enhance in vivo activity" Proc. Nat. Acad. Sci. USA, 95:1184-1188 (1998).

Tacken et al., "Definition of receptor binding sites on human interleukin-11 by molecular modeling-guided mutagenesis" European Journal of Biochemistry, vol. 265 No. 2, pp. 645-655 (Oct. 1999).

Takahashi et al. "Short stature caused by a mutant growth hormone with an antagonistic effect.", Endocr J. Oct. 1996;43 Suppl:S27-32. Abstract only, PMID 9076339.

Tanaka et al., "Pharmacokinetics of Recombinant Human Granulocyte Colony-stimulating Factor Conjugated to Polyethylene Glycol in Rats" (1991) Cancer Research 51: 3710-3714.

Tang et al. "Studies on the PEGylation of Protein at a Specific Site: Sulfhydryl-PEGylation of 97Cys-IFN-gamma.", Sheng Wu Hua Xue Yu Sheng Wu Wu Li Xue Bao (Shanghai). 1996;28(3):312-315. Abstract only, PMID:12237688.

Tymms et al., "Functional significance of amino acid residues within conserved hydrophilic regions in human interferons-α" Antiviral Res., 12:37-47 (1989).

Valenzuela D. et al., "Is Sequence Conservation in Interferons Due to Selection for Functional Proteins." Nature, vol. 313(21). pp. 698-700. Feb. 1985.

Walter et al., "Crystal Structure of Interleukin 10 Reveals and Interferon γ-like fold" Biochemistry 1995, 34, p. 12118-12125.

Walter et al., "Three-dimensional structure of recombinant human granulocyte-macrophage colony-stimulating factor." J. Mol. Biol., 224:1075-1085 (1992).

Wang et al., "Engineering and use of (32)P-labeled human recombinant interleukin-11 for receptor binding studies", Eur. J. Biochem. 269, 61-68 (2002).

Watson JD, Molecular biology of the GENE 3rd edition, p. 337, W. A. Benjamin, Inc. Menlo Park, California, Reading, Massachusetts, London, Amsterdam, Don Mills, Ontario. Sydney, 1977, ISBN 0-8053-9609-8.

Weich et al., "Interleukin-3/erythropoietin fusion proteins: in vitro effects on hematopoietic cells", Experimental Hematology, vol. 21, No. 5, pp. 647-655 (May 1993).

Wells, "Additivity of Mutational Effects in Proteins" Biochemistry, vol. 29 No. 37, pp. 8509-8517 (Sep. 1990).

Wells, "Hematopoietic Receptor Complexes" Ann. Rev. Biochem., 65:609-634 (1996).

Wen et al., "Erythropoietin Structure-Function Relationships", The Journal of Biol. Chem., vol. 269, No. 36: 22839-22846 (1994).

Wojchowski et al., "Biotinylated Recombinant Human Erythropoietins: Bioactivity and Utility as Receptor Ligand", Blood, vol. 74, No. 3, Aug. 15, 1989; pp. 952-958.

Yamasaki et al., "Effect of Divalent Polyethylene Glycol Units, Conjugated on Human Granulocyte Colony-Stimulating Factor, on Biological Activities In vitro and In Vivo", Drugs Exptl.Clin. Res., vol. 24 No. 4, pp. 191-196 (1998).

Zalipsky, "Chemistry of polyethylene glycol conjugates with biologically active molecules" Adv. Drug Delivery Reviews, 16:157-182 (1995).

Zhang et al., "Characterization of asparagine deamidation and aspartate isomerization in recombinant human interleukin-11", Pharmaceutical Research, vol. 19 No. 8, pp. 1223-1231 (Aug. 2002).

Zurawaki et al. "Definition and spatial location of mouse interleukin-2 residues that interact with the heterotrmeric receptor", Embo Journal 12, 5113-5119, 1993.

International Preliminary Examination Report for International (PCT) Patent Application No. PCT/US98/14497, mailed May 11, 1999 (4152-1-PCT).

International Search Report for International (PCT) Patent Application No. PCT/US98/14497, mailed Oct. 22, 1998 (4152-1-PCT).

Ishikawa et al., "The Substitution of Cysteine 17 of Recombinant Human G-CSF with Alanine Greatly Enhanced its Stability," Cell Structure and Function, 1992, vol. 17(1), pp. 61-65.

Caron et al., "Engineered humanized dimeric forms of IgG are more effective antibodies," J Exp Med, Oct. 1992, vol. 176(4), pp. 1191-1195.

Tiebel et al., "Conformational changes necessary for gene regulation by Tet repressor assayed by reversible disulfide bond formation," The EMBO Journal, Sep. 1998, vol. 17(17), pp. 5112-5119.

METHODS OF USE OF G-CSF CYSTEINE MUTEINS

CROSS-REFERENCE TO RELATED APPLICATIONS

This application is a continuation of 35 U.S.C. §120 of U.S. application Ser. No. 11/857,399, filed Sep. 18, 2007, which is a continuation under 35 U.S.C. §120 of U.S. application Ser. No. 10/685,288, filed Oct. 13, 2003, now U.S. Pat. No. 7,270,809, which claims the benefit of priority under 35 U.S.C. 119(e) from U.S. Provisional Application Ser. No. 60/418,106, filed Oct. 11, 2002, entitled "Methods of Use for Granulocyte Colony Stimulating Factor Cysteine Muteins", and from U.S. Provisional Application Ser. No. 60/418,105, filed Oct. 11, 2002, entitled "Methods of Use for Erythropoietin Cysteine Muteins".

U.S. application Ser. No. 10/685,288, supra, is also a continuation-in-part of U.S. application Ser. No. 10/400,377, filed Mar. 26, 2003, now U.S. Pat. No. 7,148,333, which is a divisional of U.S. application Ser. No. 09/462,941, filed Jan. 14, 2000, now U.S. Pat. No. 6,608,183, which is a national stage filing under 35 U.S.C. 371 of PCT Application Serial No. PCT/US98/14497, filed Jul. 13, 1998, which designates the United States, was published in English, and claims the benefit of priority under 35 U.S.C. 119(e) from U.S. Provisional Application Ser. No. 60/052,516, filed Jul. 14, 1997.

U.S. application Ser. No. 10/685,288, supra, is also a continuation-in-part of U.S. application Ser. No. 10/298,148, filed Nov. 15, 2002, now U.S. Pat. No. 7,153,943, which claims priority under 35 U.S.C. 119(e) from U.S. Provisional Application Ser. No. 60/418,040, filed Oct. 11, 2002 and from U.S. Provisional Application Ser. No. 60/332,285, filed Nov. 15, 2001, and which also claims priority as a continuation-in-part from said U.S. application Ser. No. 09/462,941, now U.S. Pat. No. 6,608,183.

U.S. application Ser. No. 10/685,288, supra, is also a continuation-in-part of U.S. application Ser. No. 09/889,273, filed Sep. 6, 2001, now U.S. Pat. No. 6,753,165, which is a national stage filing under 35 U.S.C. 371 of PCT Application Serial No. PCT/US00/00931, filed Jan. 14, 2000, which designates the United States, was published in English, and which claims priority under 35 U.S.C. 119(e) from U.S. Provisional Application Ser. No. 60/116,041, filed Jan. 14, 1999.

U.S. application Ser. No. 10/685,288, supra, is also a continuation-in-part of U.S. application Ser. No. 10/276,358, filed Apr. 10, 2003, now U.S. Pat. No. 7,306,931, which is a national stage filing under 35 U.S.C. 371 of PCT Application Serial No. PCT/US01/16088, filed May 16, 2001, which designated the United States, was published in English, and which claims priority under 35 U.S.C. 119(e) from U.S. Provisional Application Ser. No. 60/204,617, filed May 16, 2000.

The entire disclosure of each of the above-identified applications is incorporated herein by reference.

REFERENCE TO SEQUENCE LISTING

This application contains a Sequence Listing submitted as an electronic text file named "Sequence_Listing", having a size in bytes of 102 kb, and created on 13 Oct. 2003. The information contained in this electronic file is hereby incorporated by reference in its entirety pursuant to 37 CFR §1.52 (e)(5).

GOVERNMENT SUPPORT

This invention was made in part with government support under Grant Nos. 1R43 CA78094-01A1 and 2R44 CA78094-02,awarded by the National Cancer institute and the National Institutes of Health. The government has certain rights in the invention.

FIELD OF THE INVENTION

The present invention relates to genetically engineered therapeutic proteins and methods of using such proteins. More specifically, the engineered proteins include cysteine variants of growth hormone and related members of the growth hormone supergene family.

BACKGROUND OF THE INVENTION

The following proteins are encoded by genes of the growth hormone (GH) supergene family (Bazan (1990); Mott and Campbell (1995); Silvennoinen and Ihle (1996); Blumberg et al. (2001)): growth hormone, prolactin, placental lactogen, erythropoietin (EPO), thrombopoietin (TPO), interleukin-2 (IL-2), IL-3, IL-4, IL-5, IL-6, IL-7, IL-9, IL-10, IL-11, IL-12 (p35 subunit), IL-13, IL-15, IL-19, IL-20, IL-21, MDA-7, IL-TIF, AK-155, oncostatin M, ciliary neurotrophic factor, leukemia inhibitory factor, alpha interferon, beta interferon, gamma interferon, omega interferon, tau interferon, granulocyte-colony stimulating factor (G-CSF), granulocyte-macrophage colony stimulating factor (GM-CSF), macrophage colony stimulating factor (M-CSF) and cardiotrophin-1 (CT-1) ("the GH supergene family"). It is anticipated that additional members of this gene family will be identified in the future through gene cloning and sequencing. Members of the GH supergene family have similar secondary and tertiary structures, despite the fact that they generally have limited amino acid or DNA sequence identity. The shared structural features allow new members of the gene family to be readily identified.

There is considerable interest on the part of patients and healthcare providers in the development of long acting, "user-friendly" protein therapeutics. Proteins are expensive to manufacture and, unlike conventional small molecule drugs, are not readily absorbed by the body. Moreover, they are digested if taken orally. Therefore, natural proteins must be administered by injection. After injection, most proteins are cleared rapidly from the body, necessitating frequent, often daily, injections. Patients dislike injections, which leads to reduced compliance and reduced drug efficacy. Some proteins, such as erythropoietin (EPO), are effective when administered less often (three times per week for EPO) because they are glycosylated. However, glycosylated proteins are produced using expensive mammalian cell expression systems.

The length of time an injected protein remains in the body is finite and is determined by, e.g., the protein's size and whether or not the protein contains covalent modifications such as glycosylation. Circulating concentrations of injected proteins change constantly, often by several orders of magnitude, over a 24-hour period. Rapidly changing concentrations of protein agonists can have dramatic downstream consequences, at times under-stimulating and at other times over-stimulating target cells. Similar problems plague protein antagonists. These fluctuations can lead to decreased efficacy and increased frequency of adverse side effects for protein therapeutics. The rapid clearance of recombinant proteins from the body significantly increases the amount of protein required per patient and dramatically increases the cost of treatment. The cost of human protein pharmaceuticals is expected to increase dramatically in the years ahead as new and existing drugs are approved for more disease indications.

Thus, there is a need to develop protein delivery technologies that lower the costs of protein therapeutics to patients and healthcare providers. The present invention provides a solution to this problem by providing methods to prolong the circulating half-lives of protein therapeutics in the body so that the proteins do not have to be injected frequently. This solution also satisfies the needs and desires of patients for protein therapeutics that are "user-friendly", i.e., protein therapeutics that do not require frequent injections. The present invention solves these and other problems by providing biologically active, cysteine-added variants of members of the growth hormone supergene family. The invention also provides for the chemical modification of these variants with cysteine-reactive polymers or other types of cysteine-reactive moieties to produce derivatives thereof and the molecules so produced. The invention also provides for therapeutic methods using the protein variants described herein.

SUMMARY OF THE INVENTION

The present invention provides cysteine variants of members of the GH supergene family and uses of such cysteine variants. The variants comprise a cysteine residue substituted for a nonessential amino acid of the proteins. Preferably, the variants comprise a cysteine residue substituted for an amino acid selected from amino acids in the loop regions, the ends of the alpha helices, proximal to the first amphipathic helix, and distal to the final amphipathic helix or wherein the cysteine residue is added at the N-terminus or C-terminus of the proteins. Preferred sites for substitution are the N- and O-linked glycosylation sites. According to the present invention, "proximal to the first amphipathic helix" refers to a position preceding, or N-terminal to, the first amphipathic helix (i.e., closer to the amino-terminus of the protein than the first amphipathic helix). Similarly, "distal to the final amphipathic helix" refers to a position following, or C-terminal to, the final amphipathic helix (i.e., further away from the amino-terminus of the protein than the final amphipathic helix).

Also provided are cysteine variants wherein the amino acid substituted for is in the A-B loop, B-C loop, the C-D loop or D-E loop of interferon/interferon-10-like members of the GH supergene family.

Also provided are cysteine variants of members of the GH supergene family wherein the cysteine residue is introduced between two amino acids in the natural protein. In particular, the cysteine residue is introduced into the loop regions, the ends of the alpha helices, proximal to the first amphipathic helix, or distal to the final amphipathic helix. Even more particularly, the cysteine variant is introduced between two amino acids in an N-O-linked glycosylation site or adjacent to an amino acid in an N-linked or O-linked glycosylation site.

More particularly are provided cysteine variants wherein the loop region where the cysteine is introduced is the A-B loop, the B-C loop, the C-D loop or D-E loop of interferon/interferon-10-like members of the GH supergene family.

Such cysteine substitutions or insertion mutations also can include the insertion of one or more additional amino acids amino acids at the amino-terminal or carboxy-terminal to the cysteine substitution or insertion.

Also provided are cysteine variants that are further derivatised by PEGylating the cysteine variants and including the derivatised proteins produced thereby.

As set forth in the examples, specific cysteine variants of the members of the GH supergene family also are provided, including for example, variants of GH. The GH cysteine variants can have the substituted-for amino acid or inserted cysteine located at the N-terminal end of the A-B loop, the B-C loop, the C-D loop, the first three or last three amino acids in the A, B, C and D helices and the amino acids proximal to helix A and distal to helix D.

More particularly, the cysteine can be substituted for the following amino acids: F1, T3, P5, E33, A34, K38, E39, Q40, S43, Q46, N47, P48, Q49, T50, S51, S55, T60, A98, N99, S100, G104, A105, S106, E129, D130, G131, S132, P133, T135, G136, Q137, K140, Q141, T142, S144, K145, D147, T148, N149, S150, H151, N152, D153, S184, E186, G187, S188, and G190.

Other examples of cysteine variants according to the invention include erythropoietin variants. Erythropoietin variants include those wherein the substituted for amino acid is located in the A-B loop, the B-C loop, the C-D loop, the amino acids proximal to helix A and distal to helix D and the N- or C-terminus. Even more specifically, the EPO cysteine variants include molecules wherein the amino acids indicated below have a cysteine substituted therefor: serine-126, N24, I25, T26, N38, I39, T40, N83, S84, A1, P2, P3, R4, D8, S9, T27, G28, A30, E31, H32, S34, N36, D43, T44, K45, N47, A50, K52, E55, G57, Q58, G77, Q78, A79, Q86, W88, E89, T107, R110, A111, G113, A114, Q115, K116, E117, A118, S120, P121, P122, D123, A124, A125, A127, A128, T132, K154, T157, G158, E159, A160, T163, G164, D165, R166 and S85.

The members of the GH supergene family include growth hormone, prolactin, placental lactogen, erythropoietin, thrombopoietin, interleukin-2, interleukin-3, interleukin-4, interleukin-5, interleukin-6, interleukin-7, interleukin-9, interleukin-10, interleukin-11, interleukin-12 (p35 subunit), interleukin-13, interleukin-15, oncostatin M, ciliary neurotrophic factor, leukemia inhibitory factor, alpha interferon, beta interferon, gamma interferon, omega interferon, tau interferon, granulocyte-colony stimulating factor, granulocyte-macrophage colony stimulating factor, macrophage colony stimulating factor, cardiotrophin-1 and other proteins identified and classified as members of the family. The proteins can be derived from any animal species including human, companion animals and farm animals.

Also provided are therapeutic methods for protecting an animal from a disease or condition that is amenable to treatment by any of the wild-type growth hormone superfamily proteins described herein. The methods include administration of one or more cysteine variants (cysteine muteins) of the invention (including those with agonist or antagonist functions) to an animal for treatment of a disease or condition.

In one aspect, provided is a method to protect an animal from a disease or condition, comprising administering to the animal a composition comprising a granulocyte-macrophage colony stimulating factor (GM-CSF) cysteine mutein as described herein.

In one aspect, provided is a method to protect an animal from a disease or condition, comprising administering to the animal a composition comprising a granulocyte colony stimulating factor (G-CSF) cysteine mutein as described herein.

In one aspect, provided is a method to protect an animal from a disease or condition, comprising administering to the animal a composition comprising an erythropoietin (EPO) cysteine mutein as described herein.

In one aspect, provided is a method to protect an animal from a disease or condition, comprising administering to the animal a composition comprising an alpha interferon cysteine mutein as described herein.

Also provided is a method to prevent or treat the occurrence of neutropenia in an animal comprising administering to the animal a composition comprising a granulocyte-macrophage colony stimulating factor (GM-CSF) cysteine mutein as described herein. The neutropenia to be prevented or treated using this method can include, but is not limited to: (a) neutropenia resulting from myelosuppressive chemotherapy; (b) neutropenia associated with bone marrow transplantation (c) neutropenia associated with infection with the human immunodeficiency virus; (d) neutropenia associated with burns, surgery, dilatation, anemia and neonatal septicemia; (e) severe chronic neutropenia; or neutropenia associated with aplastic anemia and acute leukemia.

Also provided is a method to protect an animal from a disease or condition by stimulating proliferation and differentiation of hematopoietic cells in the animal, comprising administering to the animal a composition comprising a granulocyte-macrophage colony stimulating factor (GM-CSF) cysteine mutein as described herein.

Also provided is a method for stimulating the expansion and proliferation of peripheral blood progenitor cells in an animal comprising administering to the animal a composition comprising a granulocyte-macrophage colony stimulating factor (GM-CSF) cysteine mutein as described herein.

Also provided are therapeutic methods for accelerating recovery from neutropenia in patients using cysteine variants of granulocyte colony stimulating factor (G-CSF).

Also provided is a method to protect an animal from a disease or condition by stimulating proliferation and differentiation of hematopoietic cells in the animal, comprising administering to said animal a composition comprising a G-CSF cysteine mutein.

Also provided is a method for stimulating the expansion and proliferation of peripheral blood progenitor cells in an animal comprising administering to the animal a composition comprising a G-CSF cysteine mutein.

Also provided are therapeutic methods for increasing red blood cell formation and increasing hematocrit levels in patients using a cysteine variant of erythropoietin (EPO).

Also provided are therapeutic methods to regulate the proliferation and differentiation of hematopoietic progenitor cells into mature cells such as red blood cells using a cysteine variant of erythropoietin (EPO).

Also described herein are therapeutic methods for inhibiting growth of cancer cells in patients using cysteine variants of alpha interferon.

Other variations and modifications to the invention will be obvious to those skilled in the art based on the specification and the "rules" set forth herein. All of these are considered as part of the invention.

DETAILED DESCRIPTION OF THE INVENTION

The present invention relates to cysteine variants and, among other things, the site-specific conjugation of such proteins with polyethylene glycol (PEG) or other such moieties. PEG is a non-antigenic, inert polymer that significantly prolongs the length of time a protein circulates in the body. This allows the protein to be effective for a longer period of time. Covalent modification of proteins with PEG has proven to be a useful method to extend the circulating half-lives of proteins in the body (Abuchowski et al., 1984; Hershfield, 1987; Meyers et al., 1991). Covalent attachment of PEG to a protein increases the protein's effective size and reduces its rate of clearance rate from the body. PEGs are commercially available in several sizes, allowing the circulating half-lives of PEG-modified proteins to be tailored for individual indications through use of different size PEGs. Other benefits of PEG modification include an increase in protein solubility, an increase in vivo protein stability and a decrease in protein immunogenicity (Katre et al., 1987; Katre, 1990).

The preferred method for PEGylating proteins is to covalently attach PEG to cysteine residues using cysteine-reactive PEGs. A number of highly specific, cysteine-reactive PEGs with different reactive groups (e.g., maleimide, vinylsulfone) and different size PEGs (2-20 kDa) are commercially available (e.g., from Shearwater, Polymers, Inc., Huntsville, Ala.). At neutral pH, these PEG reagents selectively attach to "free" cysteine residues, i.e., cysteine residues not involved in disulfide bonds. The conjugates are hydrolytically stable. Use of cysteine-reactive PEGs allows the development of homogeneous PEG-protein conjugates of defined structure.

Considerable progress has been made in recent years in determining the structures of commercially important protein therapeutics and understanding how they interact with their protein targets, e.g., cell-surface receptors, proteases, etc. This structural information can be used to design PEG-protein conjugates using cysteine-reactive PEGs. Cysteine residues in most proteins participate in disulfide bonds and are not available for PEGylation using cysteine-reactive PEGs. Through in vitro mutagenesis using recombinant DNA techniques, additional cysteine residues can be introduced anywhere into the protein. The added cysteines can be introduced at the beginning of the protein, at the end of the protein, between two amino acids in the protein sequence or, preferably, substituted for an existing amino acid in the protein sequence. The newly added "free" cysteines can serve as sites for the specific attachment of a PEG molecule using cysteine-reactive PEGs. The added cysteine must be exposed on the protein's surface and accessible for PEGylation for this method to be successful. If the site used to introduce an added cysteine site is non-essential for biological activity, then the PEGylated protein will display essentially wild type (normal) in vitro bioactivity. The major technical challenge in PEGylating proteins with cysteine-reactive PEGs is the identification of surface exposed, non-essential regions in the target protein where cysteine residues can be added or substituted for existing amino acids without loss of bioactivity.

Cysteine-added variants of a few human proteins and PEG-polymer conjugates of these proteins have been described. U.S. Pat. No. 5,206,344 describes cysteine-added variants of IL-2. These cysteine-added variants are located within the first 20 amino acids from the amino terminus of the mature IL-2 polypeptide chain. The preferred cysteine variant is at position 3 of the mature polypeptide chain, which corresponds to a threonine residue that is O-glycosylated in the naturally occurring protein. Substitution of cysteine for threonine at position 3 yields an IL-2 variant that can be PEGylated with a cysteine-reactive PEG and retain full in vitro bioactivity (Goodson and Katre, 1990). In contrast, natural IL-2 PEGylated with lysine-reactive PEGs displays reduced in vitro bioactivity (Goodson and Katre, 1990). The effects of cysteine substitutions at other positions in IL-2 were not reported.

U.S. Pat. No. 5,166,322 teaches cysteine-added variants of IL-3. These variants are located within the first 14 amino acids from the N-terminus of the mature protein sequence. The patent teaches expression of the proteins in bacteria and covalent modification of the proteins with cysteine-reactive PEGs. No information is provided as to whether the cysteine-added variants and PEG-conjugates of IL-3 are biologically active. Cysteine-added variants at other positions in the polypeptide chain were not reported.

PCT Publication No. WO 9412219 and PCT Application No. PCT/US95/06540 teach cysteine-added variants of insulin-like growth factor-I (IGF-I). IGF-I has a very different structure from GH and is not a member of the GH supergene family (Mott and Campbell, 1995). Cysteine substitutions at many positions in the IGF-I protein are described. Only certain of the cysteine-added variants are biologically active. The preferred site for the cysteine added variant is at amino acid position 69 in the mature protein chain. Cysteine substitutions at positions near the N-terminus of the protein (residues 1-3) yielded IGF-I variants with reduced biological activities and improper disulfide bonds.

PCT Publication No. WO 9422466 teaches two cysteine-added variants of insulin-like growth factor (IGF) binding protein-1, which has a very different structure than GH and is not a member of the GH supergene family. The two cysteine-added IGF binding protein-1 variants disclosed are located at positions 98 and 101 in the mature protein chain and correspond to serine residues that are phosphorylated in the naturally-occurring protein.

U.S. patent application Ser. No. 07/822,296 teaches cysteine added variants of tumor necrosis factor binding protein, which is a soluble, truncated form of the tumor necrosis factor cellular receptor. Tumor necrosis factor binding protein has a very different structure than GH and is not a member of the GH supergene family.

IGF-I, IGF binding protein-1 and tumor necrosis factor binding protein have secondary and tertiary structures that are very different from GH and the proteins are not members of the GH supergene family. Because of this, it is difficult to use the information gained from studies of IGF-I, IGF binding protein-1 and tumor necrosis factor binding protein to create cysteine-added variants of members of the GH supergene family. The studies with IL-2 and IL-3 were carried out before the structures of IL-2 and IL-3 were known (McKay 1992; Bazan, 1992) and before it was known that these proteins are members of the GH supergene family. Previous experiments aimed at identifying preferred sites for adding cysteine residues to IL-2 and IL-3 were largely empirical and were performed prior to experiments indicating that members of the GH supergene family possessed similar secondary and tertiary structures.

Based on the structural information now available for members of the GH supergene family, the present invention provides "rules" for determining a priori which regions and amino acid residues in members of the GH supergene family can be used to introduce or substitute cysteine residues without significant loss of biological activity. In contrast to the naturally occurring proteins, these cysteine-added variants of members of the GH supergene family will possess novel properties such as the ability to be covalently modified at defined sites within the polypeptide chain with cysteine-reactive polymers or other types of cysteine-reactive moieties. The covalently modified proteins will be biologically active.

GH is the best-studied member of the GH supergene family. GH is a 22 kDa protein secreted by the pituitary gland. GH stimulates metabolism of bone, cartilage and muscle and is the body's primary hormone for stimulating somatic growth during childhood. Recombinant human GH (rhGH) is used to treat short stature resulting from GH inadequacy and renal failure in children. GH is not glycosylated and can be produced in a fully active form in bacteria. The protein has a short in vivo half-life and must be administered by daily subcutaneous injection for maximum effectiveness (MacGillivray et al., 1996). Recombinant human GH (rhGH) was approved recently for treating cachexia in AIDS patients and is under study for treating cachexia associated with other diseases.

The sequence of human GH is well known (see, e.g., Martial et al. 1979; Goeddel et al. 1979 which are incorporated herein by reference; SEQ ID NO:1). GH is closely related in sequence to prolactin and placental lactogen and these three proteins were considered originally to comprise a small gene family. The primary sequence of GH is highly conserved among animal species (Abdel-Meguid et al., 1987), consistent with the protein's broad species cross-reactivity. The three dimensional folding pattern of porcine GH has been solved by X-ray crystallography (Abdel-Meguid et al., 1987). The protein has a compact globular structure, comprising four amphipathic alpha helical bundles joined by loops. Human GH has a similar structure (de Vos et al., 1992). The four alpha helical regions are termed A-D beginning from the N-terminus of the protein. The loop regions are referred to by the helical regions they join, e.g., the A-B loop joins helical bundles A and B. The A-B and C-D loops are long, whereas the B-C loop is short. GH contains four cysteine residues, all of which participate in disulfide bonds. The disulfide assignments are cysteine53 joined to cysteine165 and cysteine182 joined to cysteine189.

The crystal structure of GH bound to its receptor revealed that GH has two receptor binding sites and binds two receptor molecules (Cunningham et al., 1991; de Vos et al., 1992). The two receptor binding sites are referred to as site I and site II. Site I encompasses the Carboxy (C)-terminal end of helix D and parts of helix A and the A-B loop, whereas site II encompasses the Amino (N)-terminal region of helix A and a portion of helix C. Binding of GH to its receptor occurs sequentially, with site I always binding first. Site II then engages a second GH receptor, resulting in receptor dimerization and activation of the intracellular signaling pathways that lead to cellular responses to GH. A GH mutein in which site II has been mutated (a glycine to arginine mutation at amino acid 120) is able to bind a single GH receptor, but is unable to dimerize GH receptors; this mutein acts as a GH antagonist in vitro, presumably by occupying GH receptor sites without activating intracellular signaling pathways (Fuh et al., 1992).

The roles of particular regions and amino acids in GH receptor binding and intracellular signaling also have been studied using techniques such as mutagenesis, monoclonal antibodies and proteolytic digestion. The first mutagenesis experiments entailed replacing entire domains of GH with similar regions of the closely related protein, prolactin (Cunningham et al., 1989). One finding was that replacement of the B-C loop of GH with that of prolactin did not affect binding of the hybrid GH protein to a soluble form of the human GH receptor, implying that the B-C loop was non-essential for receptor binding. Alanine scanning mutagenesis (replacement of individual amino acids with alanine) identified 14 amino acids that are critical for GH bioactivity (Cunningham and Wells, 1989). These amino acids are located in the helices A, B, C, and D and the A-B loop and correspond to sites I and II identified from the structural studies. Two lysine residues at amino acid positions 41 and 172, K41 and K172, were determined to be critical components of the site I receptor binding site, which explains the decrease in bioactivity observed when K172 is acetylated (Teh and Chapman, 1988). Modification of K168 also significantly reduced GH receptor binding and bioactivity (de la Llosa et al., 1985; Martal et al., 1985; Teh and Chapman, 1988). Regions of GH responsible for binding the GH receptor have also been studied using monoclonal antibodies (Cunningham et al., 1989). A series of eight monoclonal antibodies was generated to human GH and analyzed for the ability to neutralize GH activity and prevent binding of GH to its recombinant soluble receptor. The latter studies allowed the putative binding site for each monoclonal antibody to be localized within the GH three-dimensional structure. Of interest was that monoclonal antibodies 1 and 8 were unable to displace GH from binding its receptor. The binding sites for these monoclonal antibodies were localized to the B-C loop (monoclonal number 1) and the N-terminal end of the A-B loop (monoclonal number 8). No monoclonals were studied that bound the C-D loop specifically. The monoclonal antibody studies suggest that the B-C loop and N-terminal end of the A-B loop are non-essential for receptor binding. Finally, limited cleavage of GH with trypsin was found to produce a two chain derivative that retained full activity (Mills et al., 1980; Li, 1982). Mapping studies indicated that trypsin cleaved and/or deleted amino acids between positions 134 and 149, which corresponds to the C-D loop. These studies suggest the C-D loop is not involved in receptor binding or GH bioactivity.

Structures of a number of cytokines, including G-CSF (Hill et al., 1993), GM-CSF (Diederichs et al., 1991; Walter et al., 1992), IL-2 (Bazan, 1992; McKay, 1992), IL-4 (Redfield et al., 1991; Powers et al., 1992), and IL-5 (Milburn et al., 1993) have been determined by X-ray diffraction and NMR studies and show striking conservation with the GH structure, despite a lack of significant primary sequence homology. EPO is considered to be a member of this family based upon modeling and mutagenesis studies (Boissel et al., 1993; Wen et al., 1994). A large number of additional cytokines and growth factors including ciliary neurotrophic factor (CNTF), leukemia inhibitory factor (LIF), thrombopoietin (TPO), oncostatin M, macrophage colony stimulating factor (M-CSF), IL-3, IL-6, IL-7, IL-9, IL-12, IL-13, IL-15, and alpha, beta, omega, tau and gamma interferon belong to this family (reviewed in Mott and Campbell, 1995; Silvennoinen and Ihle 1996). All of the above cytokines and growth factors are now considered to comprise one large gene family, of which GH is the prototype.

In addition to sharing similar secondary and tertiary structures, members of this family share the property that they must oligomerize cell surface receptors to activate intracellular signaling pathways. Some GH family members, e.g., GH and EPO, bind a single type of receptor and cause it to form homodimers. Other family members, e.g., IL-2, IL-4, and IL-6, bind more than one type of receptor and cause the receptors to form heterodimers or higher order aggregates (Davis et al., 1993; Paonessa et al., 1995; Mott and Campbell, 1995). Mutagenesis studies have shown that, like GH, these other cytokines and growth factors contain multiple receptor binding sites, typically two, and bind their cognate receptors sequentially (Mott and Campbell, 1995; Matthews et al., 1996) Like GH, the primary receptor binding sites for these other family members occur primarily in the four alpha helices and the A-B loop (reviewed in Mott and Campbell, 1995). The specific amino acids in the helical bundles that participate in receptor binding differ amongst the family members (Mott and Campbell, 1995). Most of the cell surface receptors that interact with members of the GH supergene family are structurally related and comprise a second large multi-gene family (Bazan, 1990; Mott and Campbell, 1995; Silvennoinen and Ihle 1996).

A general conclusion reached from mutational studies of various members of the GH supergene family is that the loops joining the alpha helices generally tend to not be involved in receptor binding. In particular the short B-C loop appears to be non-essential for receptor binding in most, if not all, family members. For this reason, the B-C loop is a preferred region for introducing cysteine substitutions in members of the GH supergene family. The A-B loop, the B-C loop, the C-D loop (and D-E loop of interferon/IL-10-like members of the GH superfamily) also are preferred sites for introducing cysteine mutations. Amino acids proximal to helix A and distal to the final helix also tend not to be involved in receptor binding and also are preferred sites for introducing cysteine substitutions. Certain members of the GH family, e.g., EPO, IL-2, IL-3, IL-4, IL-6, G-CSF, GM-CSF, TPO, IL-10, IL-12 p35, IL-13, IL-15 and beta-interferon contain N-linked and O-linked sugars. The glycosylation sites in the proteins occur almost exclusively in the loop regions and not in the alpha helical bundles. Because the loop regions generally are not involved in receptor binding and because they are sites for the covalent attachment of sugar groups, they are preferred sites for introducing cysteine substitutions into the proteins. Amino acids that comprise the N- and O-linked glycosylation sites in the proteins are preferred sites for cysteine substitutions because these amino acids are surface-exposed, the natural protein can tolerate bulky sugar groups attached to the proteins at these sites and the glycosylation sites tend to be located away from the receptor binding sites.

Many additional members of the GH gene family are likely to be discovered in the future. New members of the GH supergene family can be identified through computer-aided secondary and tertiary structure analyses of the predicted protein sequences. Members of the GH supergene family will possess four or five amphipathic helices joined by non-helical amino acids (the loop regions). The proteins may contain a hydrophobic signal sequence at their N-terminus to promote secretion from the cell. Such later discovered members of the GH supergene family also are included within this invention.

The present invention provides "rules" for creating biologically active cysteine-added variants of members of the GH supergene family. These "rules" can be applied to any existing or future member of the GH supergene family. The cysteine-added variants will posses novel properties not shared by the naturally occurring proteins. Most importantly, the cysteine added variants will possess the property that they can be covalently modified with cysteine-reactive polymers or other types of cysteine-reactive moieties to generate biologically active proteins with improved properties such as increased in vivo half-life, increased solubility and improved in vivo efficacy.

Specifically, the present invention provides biologically active cysteine variants of members of the GH supergene family by substituting cysteine residues for non-essential amino acids in the proteins. Preferably, the cysteine residues are substituted for amino acids that comprise the loop regions, for amino acids near the ends of the alpha helices and for amino acids proximal to the first amphipathic helix or distal to the final amphipathic helix of these proteins. Other preferred sites for adding cysteine residues are at the N-terminus or C-terminus of the proteins. Cysteine residues also can be introduced between two amino acids in the disclosed regions of the polypeptide chain. The present invention teaches that N- and O-linked glycosylation sites in the proteins are preferred sites for introducing cysteine substitutions either by substitution for amino acids that make up the sites or, in the case of N-linked sites, introduction of cysteines therein. The glycosylation sites can be serine or threonine residues that are O-glycosylated or asparagine residues that are N-glycosylated. N-linked glycosylation sites have the general structure asparagine-X-serine or threonine (N-X-S/T), where X can be any amino acid. The asparagine residue, the amino acid in the X position and the serine/threonine residue of the N-linked glycosylation site are preferred sites for creating biologically active cysteine-added variants of these proteins. Amino acids immediately surrounding or adjacent to the O-linked and N-linked glycosylation sites (within about 10 residues on either side of the glycosylation site) are preferred sites for introducing cysteine-substitutions.

More generally, certain of the "rules" for identifying preferred sites for creating biologically active cysteine-added protein variants can be applied to any protein, not just proteins that are members of the GH supergene family. Specifically, preferred sites for creating biologically active cysteine variants of proteins (other than IL-2) are O-linked glycosylation sites. Amino acids immediately surrounding the O-linked glycosylation site (within about 10 residues on either side of the glycosylation site) also are preferred sites. N-linked glycosylation sites, and the amino acid residues immediately adjacent on either side of the glycosylation site (within about 10 residues of the N-X-S/T site) also are preferred sites for creating cysteine added protein variants. Amino acids that can be replaced with cysteine without significant loss of biological activity also are preferred sites for creating cysteine-added protein variants. Such non-essential amino acids can be identified by performing cysteine-scanning mutagenesis on the target protein and measuring effects on biological activity. Cysteine-scanning mutagenesis entails adding or substituting cysteine residues for individual amino acids in the polypeptide chain and determining the effect of the cysteine substitution on biological activity. Cysteine scanning mutagenesis is similar to alanine-scanning mutagenesis (Cunningham et al., 1992), except that target amino acids are individually replaced with cysteine rather than alanine residues.

Application of the "rules" to create cysteine-added variants and conjugates of protein antagonists also is contemplated. Excess production of cytokines and growth factors has been implicated in the pathology of many inflammatory conditions such as rheumatoid arthritis, asthma, allergies and wound scarring. Excess production of GH has been implicated as a cause of acromegaly. Certain growth factors and cytokines, e.g., GH and IL-6, have been implicated in proliferation of particular cancers. Many of the growth factors and cytokines implicated in inflammation and cancer are members of the GH supergene family. There is considerable interest in developing protein antagonists of these molecules to treat these diseases. One strategy involves engineering the cytokines and growth factors so that they can bind to, but not oligomerize receptors. This is accomplished by mutagenizing the second receptor binding site (site II) on the molecules. The resulting muteins are able to bind and occupy receptor sites but are incapable of activating intracellular signaling pathways. This strategy has been successfully applied to GH to make a GH antagonist (Cunningham et al., 1992). Similar strategies are being pursued to develop antagonists of other members of the GH supergene family such as IL-2 (Zurawski et al., 1990; Zurawski and Zurawski, 1992), IL-4 (Kruse et al., 1992), IL-5 (Tavernier et al., 1995), GM-CSF (Hercus et al., 1994) and EPO (Matthews et al., 1996). Since the preferred sites for adding cysteine residues to members of the GH supergene family described here lie outside of the receptor binding sites in these proteins, and thus removed from any sites used to create protein antagonists, the cysteine-added variants described herein could be used to generate long-acting versions of protein antagonists. As an example, Cunningham et al. (1992) developed an in vitro GH antagonist by mutating a glycine residue (amino acid 120) to an arginine. This glycine residue is a critical component of the second receptor binding site in GH; when it is replaced with arginine, GH cannot dimerize receptors. The glycine to arginine mutation at position 120 can be introduced into DNA sequences encoding the cysteine-added variants of GH contemplated herein to create a cysteine-added GH antagonist that can be conjugated with cysteine-reactive PEGs or other types of cysteine-reactive moieties. Similarly, amino acid changes in other proteins that turn the proteins from agonists to antagonists could be incorporated into DNA sequences encoding cysteine-added protein variants described herein. Considerable effort is being spent to identify amino acid changes that convert protein agonists to antagonists. Hercus et al. (1994) reported that substituting arginine or lysine for glutamic acid at position 21 in the mature GM-CSF protein converts GM-CSF from an agonist to an antagonist. Tavernier et al. (1995) reported that substituting glutamine for glutamic acid at position 13 of mature IL-5 creates an IL-5 antagonist. Prolactin antagonists can be created by substituting other amino acids, in particular alanine, aspartic acid and glutamic acid, for serine-179 of prolactin (Chen et al., 1998). Receptor antagonists of erythropoietin can be created by substituting alanine for arginine-103 of erythropoietin (Matthews et al., 1996).

Experimental strategies similar to those described above can be used to create cysteine-added variants (both agonists and antagonists) of members of the GH supergene family derived from various animals. This is possible because the primary amino acid sequences and structures of cytokines and growth factors are largely conserved between human and animal species. For this reason, the "rules" disclosed herein for creating biologically active cysteine-added variants of members of the GH supergene family will be useful for creating biologically active cysteine-added variants of members of the GH supergene family of companion animals (e.g., dogs, cats, horses) and commercial animal (e.g., cow, sheep, pig) species. Conjugation of these cysteine-added variants with cysteine-reactive PEGs will create long-acting versions of these proteins that will benefit the companion animal and commercial farm animal markets.

Proteins that are members of the GH supergene family (hematopoietic cytokines) are provided in Silvennoimem and Ihle (1996). Silvennoimem and Ihle (1996) also provide information about the structure and expression of these proteins. DNA sequences, encoded amino acids and in vitro and in vivo bioassays for the proteins described herein are described in Aggarwal and Gutterman (1992; 1996), Aggarwal (1998), and Silvennoimem and Ihle (1996). Bioassays for the proteins also are provided in catalogues of various commercial suppliers of these proteins such as R&D Systems, Inc. and Endogen, Inc.

The cysteine variants of the present invention can be used for any of the known therapeutic uses of the native proteins in essentially the same forms and doses all well known in the art. By way of example, therapeutic methods for increasing hematopoeisis in a patient and for accelerating recovery from neutropenia are described herein which use a cysteine variant of granulocyte macrophage colony stimulating factor (GM-CSF) according to the present invention. Also described herein are therapeutic methods for accelerating recovery from neutropenia in patients using cysteine variants of granulocyte colony stimulating factor (G-CSF), therapeutic methods for increasing red blood cell formation and increasing hematocrit levels in patients using a cysteine variant of erythopoietin (EPO), and therapeutic methods for inhibiting growth of cancer cells in patients using cysteine variants of alpha interferon. It is to be understood, however, that general discussion regarding modes of administration, dosage and delivery of cysteine variants such as the GM-CSF, G-CSF, EPO and alpha interferon cysteine muteins, is generally intended to apply to therapeutic methods using any of the cysteine variants described herein.

One embodiment of the invention relates to a method to treat or protect an animal from a disease or condition that is amenable to treatment with granulocyte-macrophage colony stimulating factor (GM-CSF), comprising administering to the animal a composition comprising a granulocyte-macrophage colony stimulating factor (GM-CSF) cysteine mutein as described herein. In one embodiment, the cysteine mutein is prepared using methods described in PCT Application No. PCT/US01/16088 (PCT Publication No. WO 01/87925 A2, published Nov. 22, 2001), incorporated herein by reference in its entirety.

Another embodiment of the invention relates to a method to treat or protect an animal from a disease or condition which is amenable to treatment with granulocyte colony stimulating factor (G-CSF), comprising administering to the animal a composition comprising a granulocyte colony stimulating factor (G-CSF) cysteine mutein as described herein. In one embodiment, the cysteine mutein is prepared using methods described in PCT Application No. PCT/US01/16088, supra.

Another embodiment of the invention relates to a method to treat or protect an animal from a disease or condition that is amenable to treatment with erythropoietin (EPO), comprising administering to the animal a composition comprising an erythropoietin (EPO) cysteine mutein as described herein. In one embodiment, the cysteine mutein is prepared using methods described in PCT Application No. PCT/US00/00931 (PCT Publication No. WO 00/42175, published Jul. 20, 2000), incorporated herein by reference in its entirety.

Another embodiment of the invention relates to a method to protect an animal from a disease or condition that is amenable to treatment with alpha interferon, comprising administering to the animal a composition comprising an alpha interferon cysteine mutein as described herein. In one embodiment, the cysteine mutein is prepared using methods described in PCT Application No. PCT/US00/00931, supra, and PCT Application No. PCT/US01/16088, supra.

Another embodiment of the invention relates to a method to prevent or treat the occurrence of neutropenia in an animal comprising administering to the animal a composition comprising a granulocyte-macrophage colony stimulating factor (GM-CSF) cysteine mutein as described herein and in one embodiment, as prepared using methods described in PCT Application No. PCT/US01/16088, supra. Another embodiment of the invention relates to a method to prevent or treat the occurrence of neutropenia in an animal comprising administering to the animal a composition comprising a G-CSF cysteine mutein as described herein and in one embodiment, as prepared using methods described in PCT Application No. PCT/US01/16088, supra. The neutropenia to be prevented or treated using this method can include, but is not limited to: (a) neutropenia resulting from myelosuppressive chemotherapy; (b) neutropenia associated with bone marrow transplantation (c) neutropenia associated with infection with the human immunodeficiency virus; (d) neutropenia associated with burns, surgery, dilatation, anemia and neonatal septicemia; (e) severe chronic neutropenia; or neutropenia associated with aplastic anemia and acute leukemia.

Another embodiment of the present invention relates to a method to protect an animal from a disease or condition by stimulating proliferation and differentiation of hematopoietic cells in the animal, comprising administering to said animal a composition comprising a granulocyte-macrophage colony stimulating factor (GM-CSF) cysteine mutein as described herein and in one embodiment, as prepared using methods described in PCT Application No. PCT/US01/16088, supra.

Another embodiment of the present invention relates to a method to protect an animal from a disease or condition by stimulating proliferation and differentiation of hematopoietic cells in the animal, comprising administering to said animal a composition comprising a G-CSF cysteine mutein as described herein and in one embodiment, as prepared using methods described in PCT Application No. PCT/US01/16088, supra.

Another embodiment of the present invention relates to a method to protect an animal from a disease or condition by stimulating proliferation and differentiation of hematopoietic cells in the animal, comprising administering to said animal a composition comprising an EPO cysteine mutein as described herein and in one embodiment, as prepared using methods described in PCT Application No. PCT/US00/00931, supra.

Hematopoeitic cells include, but are not limited to, neutrophil, monocyte, eosinophil, erythroid, and megakaryocyte cell lineages. According to the present invention, a cell of hematopoietic lineage is able to develop into cell types including, but not limited to, erythrocyte cells (i.e. a red blood cell), leukocyte cells (i.e. a white blood cell), or thrombocyte cells (i.e. platelet cell). Leukocyte cells include, but are not limited to, granular leukocytes, including eosinophils, basophils, neutrophils, and mast cells; as well as non-granular leukocytes, including megakaryocytes, polymorphonuclear cells, lymphocytes and monocytes (i.e. macrophages). According to the present invention, the term "lineage" refers to all of the stages of the development of a cell type, from the earliest precursor cell to a completely mature cell (i.e. a specialized cell). As used herein, the terms "develop", "differentiate" and "mature" all refer to the progression of a cell from the stage of having the potential to differentiate into at least two different cellular lineages to becoming a specialized cell. Such terms can be used interchangeably for the purposes of the present application.

Yet another embodiment of the present invention relates to a method for stimulating the expansion and proliferation of peripheral blood progenitor cells in an animal comprising administering to the animal a composition comprising a granulocyte-macrophage colony stimulating factor (GM-CSF) cysteine mutein as described herein and in one embodiment, as prepared using methods described in PCT Application No. PCT/US01/16088, supra.

Another embodiment of the present invention relates to a method for stimulating the expansion and proliferation of peripheral blood progenitor cells in an animal comprising administering to the animal a composition comprising a G-CSF cysteine mutein as described herein and in one embodiment, as prepared using methods described in PCT Application No. PCT/US01/16088, supra.

Reference to a progenitor cell or a precursor cell is reference to a group of cells capable of developing into a more mature cell. A precursor cell population can comprise cells that are totipotent, cells that are pluripotent and cells that are stem cell lineage restricted (i.e. cells capable of developing into less than all hematopoietic lineages, or into, for example, only cells of erythroid lineage). Peripheral blood progenitor cells are cells that differentiate into various cells that circulate in the blood, such as peripheral blood mononuclear cells (PBMC).

Granulocyte-Macrophage Colony Stimulating Factor (GM-CSF) is a glycoprotein having a molecular mass of 14.5-35 kDa that regulates the proliferation and differentiation of hematopoietic progenitor cells into mature cells such as mature neutrophils, macrophages and eosinophils. GM-CSF also stimulates the functional properties of mature monocytes, neutrophils and eosinophils. Recombinant GM-CSF is used to ameliorate neutropenia following myelosuppressive chemotherapy and bone marrow transplantation. GM-CSF also has been used to treat severe chronic neutropenia, aplastic anemia, and acute leukemia, and to mobilize peripheral blood progenitor cells for transplantation and blood banking. GM-CSF also may be useful for reversing neutropenia associated with the human immunodeficiency virus, burns, surgery, dilatation, anemia and neonatal septicemia. The ability of GM-CSF to enhance the functional properties of monocytes, neutrophils and eosinophils suggests that GM-CSF may have utility as an anti-neoplastic agent either alone or in combination with other anti-neoplastic agents such as cytotoxic drugs, chemotherapeutic agents, polyclonal antibodies and monoclonal antibodies targeting tumor cells. The immunomodulatory properties of GM-CSF also suggest that GM-CSF may have utility as an adjuvant for vaccines against tumors and infectious agents.

GM-CSF has a short circulating half life, which necessitates daily subcutaneous injections for maximum effectiveness in humans. The present inventors have created novel GM-CSF analogs (i.e., the GM-CSF cysteine muteins described herein) with improved in vivo characteristics such as increased circulating half-life and improved therapeutic efficacy through site-specific chemical modification of the protein with cysteine-reactive Polyethylene Glycol (PEG) reagents. These analogs were created by introducing a "free" cysteine residue (i.e., a cysteine residue not involved in a disulfide bond) into the protein using site-directed mutagenesis. The free cysteine residue serves as the site for covalent modification of the protein with cysteine-reactive PEG reagents. The present application teaches a variety of human GM-CSF cysteine muteins that can be modified with cysteine-reactive PEG reagents and retain biological activity, and PCT Application No. PCT/US01/16088, supra, describes additional methods of preparing such muteins.

Human and rodent GM-CSF proteins perform similar functions in their respective species and studies with rodent GM-CSF proteins can be used to predict the function of human GM-CSF in humans. Human and rodent GM-CSF proteins share 50-60% amino acid identity, but there is no cross species cross-reactivity in terms of biological activity or receptor binding. It is possible to use the significant amino acid identity between human and rodent GM-CSF proteins to construct murine GM-CSF cysteine muteins that are analogues of human GM-CSF cysteine muteins. The murine GM-CSF cysteine analogs can be expressed, purified and PEGylated using procedures similar to those described for human GM-CSF cysteine variants herein and in PCT Application No. PCT/US01/16088, supra. Biological activities of the PEGylated murine GM-CSF cysteine muteins can be tested in rodent animal disease models and used to predict the effectiveness of PEGylated human GM-CSF cysteine analogs in humans. Toward that end, the present inventors constructed the murine GM-CSF T3C mutein, which is an analog of the human GM-CSF A3C mutein described herein. As shown in Example 26, the PEGylated murine T3C analog is effective at stimulating hematopoiesis in a mammal (a rodent), which indicates that PEGylated human GM-CSF cysteine muteins will be effective at stimulating hematopoiesis in humans. Stimulating hematopoiesis will be useful for ameliorating disease indications in which hematopoiesis is impaired, such as neutropenia (see Example 27). PEGylated human GM-CSF cysteine analogs can used to ameliorate neutropenia following myelosuppressive chemotherapy and bone marrow transplantation based on the observed efficacy of GM-CSF in these indications (Cebon and Lieschke 1994). Similarly PEGylated human GM-CSF cysteine analogs will be useful in treating diseases and conditions for which the therapeutic use of GM-CSF is well established (Armitage, 1998) such as peripheral blood cell progenitor cell transplantation, engraftment failure or delay after bone marrow transplantation, and induction therapy for acute myelogenous leukemia.

Similarly, based on the observed effects of GM-CSF, PEGylated human GM-CSF cysteine analogs also may be useful in treatment of a wide variety of cancers such as breast cancer, lung cancer, non-Hodgkin's lymphoma and ovarian cancer, by allowing chemotherapy dose intensification (Cebon and Lieschke 1994). Human GM-CSF also can be used to treat severe chronic neutropenia, for example in Felty syndrome (Joseph et al, 1991) or myelokathexis (Hess et al.), as well as aplastic anemia, and acute leukemia. Human GM-CSF (and therefore GM-CSF cysteine variants of the invention) also may be useful for reversing neutropenia associated with the human immunodeficiency virus infection, myelodysplastic syndrome and ideopathic neutropenia (Kaczmarski et al, 1993). Neutropenia resulting from other causes such as burns, surgery, dilatation, anemia and neonatal septicemia may also be treated by administration of PEGylated human GM-CSF cysteine analogs. The ability of GM-CSF to enhance the functional properties of monocytes, neutrophils and eosinophils suggests that PEGylated human GM-CSF cysteine analogs may have utility as an anti-neoplastic agent either alone or in combination with other anti-neoplastic agents such as cytotoxic drugs, chemotherapeutic agents, polyclonal antibodies and monoclonal antibodies targeting tumor cells (Armitage, 1998). GM-CSF administration may be useful in the treatment of prostate cancer (Small et al, 1999). GM-CSF monotherapy also has been reported to reduce melanoma metastases (Hoeller et al, 2001). GM-CSF also may be useful in the treatment of melanoma when co-administered with anti-neoplastic agents (Vaughan et al, 2000). The immunomodulatory properties of GM-CSF also suggest that PEGylated human GM-CSF cysteine analogs may have utility as an adjuvant for vaccines against tumors and infectious agents (Gaudernack and Gjertsen, 1999, Warren and Weiner, 2000). For example adjuvant therapy using GM-CSF may be useful in treatment of malignant melanoma (Spitler et al, 2000) following surgical resection. GM-CSF co-administration with a monoclonal antibody-based immunogen may be useful in the treatment of metastatic coleorectal cancer (Rucker et al. 1999). The immunomodulatory properties of GM-CSF indicate that PEGylated human GM-CSF cysteine analogs may also provide useful therapy for enhancing immune function in immunocompromised patients such as those infected with the HIV virus (Armitage, 1998). The immunomodulatory properties of GM-CSF indicate that PEGylated human GM-CSF cysteine analogs may also provide useful therapy against bacterial and fungal infections (Armitage, 1998; Jones, 1999).

GM-CSF also may be used to accelerate wound healing of surgical incisions (Jyung et al., 1994) and also to accelerate healing of refractory wounds or ulcers such as those of patients with diabetes Canturk et al, 1999) and PEGylated human GM-CSF cysteine analogs may also be used in these indications.

In some diseases, antagonists of GM-CSF activity could provide therapeutic benefit. For example there is evidence that rheumatoid arthritis is promoted by GM-CSF activity (Campbell et al, 1997; Bischof et al, 2000; Campbell et al., 1998; Yang and Hamilton, 2001) and an anti-GM-CSF antibody has been shown to reduce the severity of arthritis observed in a murine model (Cook et al, 2001). Therefore PEGylated human GM-CSF cysteine analogs that contain one or more additional mutations that result in GM-CSF antagonist activity could be used to treat arthritis. GM-CSF activity is similarly implicated in the development and progression of multiple sclerosis (McQualter et al., 2001) and PEGylated human GM-CSF cysteine analogs that contain one or more additional mutations that result in GM-CSF antagonist activity could be used to treat multiple sclerosis.

As discussed above, various embodiments of the invention relate to methods of use of GM-CSF cysteine muteins. In particular, the present invention relates to the use of these muteins to protect an animal from a disease or condition that is amenable to treatment by the use of wild-type GM-CSF or an antagonist thereof, or which might be particularly amenable to treatment using the GM-CSF cysteine muteins of the present invention.

Erythropoietin (EPO) is a 35-39 kDa glycoprotein hormone produced by the kidney that stimulates red blood cell formation. EPO is used to treat anemia or low hematocrit levels resulting from chemotherapy, renal failure, and drug complications, and to boost red blood cell levels prior to elective surgeries. A limitation of recombinant human EPO in the clinical setting is the fact that EPO, although highly glycosylated, has a relatively short circulating half-life in humans, and pharmacodynamic studies indicate that it is best given by intravenous or subcutaneous injections 2 to 3 times per week. The present inventors have created novel EPO analogs (i.e., the EPO cysteine muteins described herein) with improved in vivo characteristics such as increased circulating half-life and improved therapeutic efficacy through site-specific chemical modification of the protein with cysteine-reactive PEG reagents. These analogs were created by introducing a "free" cysteine residue (i.e., a cysteine residue not involved in a disulfide bond) into the protein using site-directed mutagenesis. The free cysteine residue serves as the site for covalent modification of the protein with cysteine-reactive PEG reagents. The present application teaches a variety of human EPO cysteine muteins that can be modified with cysteine-reactive PEG reagents and retain biological activity, and PCT Application No. PCT/US00/00931, supra, describes additional methods of preparing such muteins.

The present invention generally relates to methods of use of erythropoietin ("EPO") cysteine muteins. In particular, the present invention relates to the use of these muteins to protect an animal from a disease or condition that is amenable to treatment by the use of wild-type EPO, or which might be particularly amenable to treatment using the EPO cysteine muteins of the present invention. In particular, protecting an animal from a disease is accomplished by inducing a beneficial or protective therapeutic response in the animal by administration of an EPO cysteine mutein of the present invention.

G-CSF is a 19 kDa glycoprotein cytokine that stimulates the proliferation, differentiation and functional activation of neutrophilic granulocytes. G-CSF is widely used to ameliorate neutropenia following myelosuppressive chemotherapy and bone marrow transplantation. G-CSF also is used to treat severe chronic neutropenia, aplastic anemia, acute leukemia and to mobilize peripheral blood progenitor cells for transplantation and blood banking. A limitation of G-CSF in the clinical setting is the fact that G-CSF has a short circulating half-life in humans, which necessitates daily subcutaneous injections for maximum effectiveness. The present inventors have created novel G-CSF analogs (i.e., the G-CSF cysteine muteins described herein) with improved in vivo characteristics such as increased circulating half-life and improved therapeutic efficacy through site-specific chemical modification of the protein with cysteine-reactive PEG reagents. These analogs were created by introducing a "free" cysteine residue (i.e., a cysteine residue not involved in a disulfide bond) into the protein using site-directed mutagenesis. The free cysteine residue serves as the site for covalent modification of the protein with cysteine-reactive PEG reagents. The present application teaches a variety of human G-CSF cysteine muteins that can be modified with cysteine-reactive PEG reagents and retain biological activity, and PCT Application No. PCT/US01/16088, supra, describes additional methods of preparing such muteins.

The present invention also relates to methods of use of G-CSF cysteine muteins. In particular, the present invention relates to the use of these muteins to protect an animal from a disease or condition that is amenable to treatment by the use of wild-type G-CSF, or which might be particularly amenable to treatment using the G-CSF cysteine muteins of the present invention. Protecting an animal from a disease is accomplished by inducing a beneficial or protective therapeutic response in the animal by administration of a G-CSF cysteine mutein of the present invention.

Alpha interferon (IFN-$\alpha$) is a protein that exhibits antiviral and antiproliferative effects on many cell types. There are over 25 distinct IFN-$\alpha$ genes. The IFN-$\alpha$2 protein is approved for use in humans and the most is known about its activity in the human clinical setting. Recombinant IFN-c' is used to treat viral diseases such as Hepatitis B, Hepatitis C and genital warts, and cancers including, but not limited to, leukemias, including hairy cell leukemia, malignant melanoma, and AIDS-related Kaposi's sarcoma. A limitation of recombinant human IFN-$\alpha$ in the clinical setting is the fact that IFN-$\alpha$ has a short circulating half-life in humans and generally must be administered by daily subcutaneous or intramuscular injection or by thrice weekly injections. The present inventors have created novel IFN-$\alpha$ analogs (i.e., the IFN-$\alpha$ cysteine muteins described herein) with improved in vivo characteristics such as increased circulating half-life and improved therapeutic efficacy through site-specific chemical modification of the protein with cysteine-reactive PEG reagents. These analogs were created by introducing a "free" cysteine residue (i.e., a cysteine residue not involved in a disulfide bond) into the protein using site-directed mutagenesis. The free cysteine residue serves as the site for covalent modification of the protein with cysteine-reactive PEG reagents. The present application teaches a variety of human IFN-$\alpha$ cysteine muteins that can be modified with cysteine-reactive PEG reagents and retain biological activity, and PCT Application No. PCT/US01/16088, supra, and PCT/US00/00931, supra, describe additional methods of preparing such muteins. The present invention generally relates to methods of use of IFN-$\alpha$ cysteine muteins. In particular, the present invention relates to the use of these muteins to protect an animal from a disease or condition that is amenable to treatment by the use of wild-type IFN-$\alpha$, or which might be particularly amenable to treatment using the IFN-$\alpha$ cysteine muteins of the present invention. In particular, protecting an animal from a disease is accomplished by inducing a beneficial or protective therapeutic response in the animal by administration of an IFN-$\alpha$ cysteine mutein of the present invention.

As used herein, the phrase "protected from a disease" refers to reducing the symptoms of the disease, reducing the occurrence of the disease, and/or reducing the severity of the disease. Protecting an animal can refer to the ability of a therapeutic composition of the present invention, when administered to an animal, to prevent a disease from occurring and/or to cure or to alleviate disease symptoms, signs or causes. As such, to protect an animal from a disease includes both preventing disease occurrence (prophylactic treatment) and treating an animal that has a disease or that is experiencing initial symptoms of a disease (therapeutic treatment). In particular, protecting an animal from a disease is accomplished by inducing a beneficial or protective therapeutic response in the animal by administration of a GM-CSF cysteine mutein, a G-CSF cysteine mutein, an EPO cysteine mutein, an IFN-α cysteine mutein, or any of the other cysteine muteins of the present invention as described herein. The term, "disease" refers to any deviation from the normal health of a mammal and includes a state when disease symptoms are present, as well as conditions in which a deviation (e.g., infection, gene mutation, genetic defect, etc.) has occurred, but symptoms are not yet manifested.

Accordingly, a GM-CSF cysteine mutein of the present invention can be administered to regulate the proliferation and differentiation of hematopoietic progenitor cells into mature cells such as neutrophils, macrophages and eosinophils. A GM-CSF cysteine mutein can also be administered to stimulate the functional properties of mature monocytes, neutrophils and eosinophils. A GM-CSF cysteine mutein, or antagonist thereof, can be administered to an animal to prevent or ameliorate any disease or condition for which the use of the wild-type protein, or antagonist thereof, respectively, can be used. Such diseases and conditions are described in detail above. In one embodiment, a GM-CSF cysteine mutein of the present invention is used as an anti-neoplastic agent either alone or in combination with other anti-neoplastic agents such as cytotoxic drugs, chemotherapeutic agents, polyclonal antibodies and monoclonal antibodies targeting tumor cells. In yet another embodiment, the GM-CSF cysteine mutein of the present invention is used as an adjuvant for vaccines against tumors and infectious agents.

Accordingly, an EPO cysteine mutein of the present invention can be administered to regulate the proliferation and differentiation of hematopoietic progenitor cells into mature cells such as red blood cells. An EPO cysteine mutein, or antagonist thereof, can be administered to an animal to prevent or ameliorate any disease or condition for which the use of the wild-type protein, or antagonist thereof, respectively, can be used. Such diseases and conditions are described in detail above. Accordingly, an EPO cysteine mutein of the present invention can be administered to treat anemia or low blood hematocrit levels resulting from chemotherapy, renal disease, renal failure, and drug complications, and to boost red blood cell levels prior to elective surgeries.

As discussed above, an EPO cysteine mutein or composition comprising the same of the present invention is administered to an animal in a manner effective to deliver the composition to a target cell, a target tissue, or systemically to the animal, whereby provision of a therapeutic benefit is achieved as a result of the administration of the mutein or composition. Suitable administration protocols include any in vivo or ex vivo administration protocol. According to the present invention, suitable methods of administering a composition of the present invention to a patient include any route of in vivo administration that is suitable for delivering the composition into a patient. The preferred routes of administration will be apparent to those of skill in the art, depending on the type of condition to be prevented or treated and/or the target cell population.

The present invention also relates to methods of use of G-CSF cysteine muteins. A G-CSF cysteine mutein, or antagonist thereof, can be administered to an animal to prevent or ameliorate any disease or condition for which the use of the wild-type protein, or antagonist thereof, respectively, can be used. Accordingly, a G-CSF cysteine mutein of the present invention can be administered to regulate the proliferation and differentiation of hematopoietic progenitor cells into mature neutrophils, macrophages and eosinophils. A G-CSF cysteine mutein can also be administered to stimulates the functional properties of mature neutrophils and eosinophils. Another embodiment of the invention is the administration of a G-CSF cysteine mutein to ameliorate neutropenia following myelosuppressive chemotherapy and/or bone marrow transplantation. A G-CSF cysteine mutein of the present invention can also be administered to an animal to treat severe chronic neutropenia, aplastic anemia, and acute leukemia, and to mobilize peripheral blood progenitor cells for transplantation and blood banking. A G-CSF cysteine mutein of the present invention can also be administered to an animal to reverse neutropenia associated with the human immunodeficiency virus, burns, surgery, dilatation, anemia and neonatal septicemia.

As discussed above, a G-CSF cysteine mutein or composition comprising the same of the present invention is administered to an animal in a manner effective to deliver the composition to a target cell, a target tissue, or systemically to the animal, whereby provision of a therapeutic benefit is achieved as a result of the administration of the mutein or composition. Suitable administration protocols include any in vivo or ex vivo administration protocol. According to the present invention, suitable methods of administering a composition of the present invention to a patient include any route of in vivo administration that is suitable for delivering the composition into a patient. The preferred routes of administration will be apparent to those of skill in the art, depending on the type of condition to be prevented or treated and/or the target cell population.

The present invention also relates to methods of use of IFN-α cysteine muteins. An IFN-α cysteine mutein, or antagonist thereof, can be administered to an animal to prevent or ameliorate any disease or condition for which the use of the wild-type protein, or antagonist thereof, respectively, can be used. Accordingly, an IFN-α cysteine mutein of the present invention can be administered to treat viral diseases including, but not limited to Hepatitis B, Hepatitis C, Severe Acute Respiratory Syndrome (SARS) and genital warts, and to treat various cancers including, but not limited to leukemias, hairy cell leukemia, melanoma, breast cancer, colon cancer, and Kaposi's sarcoma. In one embodiment, an IFN-α cysteine mutein of the present invention is used as an anti-neoplastic agent either alone or in combination with other anti-neoplastic agents such as cytotoxic drugs, chemotherapeutic agents, polyclonal antibodies and monoclonal antibodies targeting tumor cells. In yet another embodiment, an IFN-α cysteine mutein of the present invention is used as an antiviral agent either alone or in combination with other antiviral agents such as other anti-viral drugs, including ribivarin and its derivatives, other cytokines such as GM-CSF, interleukin-2, other alpha interferon species, beta interferon, and gamma interferon, and polyclonal antibodies and monoclonal antibodies targeting viruses or virally infected cells.

As discussed above, an IFN-α cysteine mutein or composition comprising the same of the present invention is administered to an animal in a manner effective to deliver the composition to a target cell, a target tissue, or systemically to the animal, whereby provision of a therapeutic benefit is achieved as a result of the administration of the mutein or composition. Suitable administration protocols include any in vivo or ex vivo administration protocol. According to the present invention, suitable methods of administering a composition of the present invention to a patient include any route of in vivo administration that is suitable for delivering the composition into a patient. The preferred routes of administration will be apparent to those of skill in the art, depending on the type of condition to be prevented or treated and/or the target cell population.

Cysteine muteins of the present invention are preferably administered in a composition. Compositions can include a cysteine mutein of the invention and any other suitable pharmaceutically acceptable carrier, as well as, in some aspects, additional components that may be useful in the treatment of a give disease or condition. According to the present invention, a "pharmaceutically acceptable carrier" includes pharmaceutically acceptable excipients and/or pharmaceutically acceptable delivery vehicles, which are suitable for use in administration of the composition to a suitable in vitro, ex vivo or in vivo site. A suitable in vitro, in vivo or ex vivo site is preferably any site where the cysteine mutein will provide a detectable effect as compared to in the absence of the mutein, and includes a disease site or a site of cell types to be contacted with the mutein. Preferred pharmaceutically acceptable carriers are capable of maintaining the mutein of the present invention in a form that, upon arrival of the mutein at the cell target in a culture or in patient, the mutein is capable of interacting with its target (e.g., hematopoeitic cell for GM-CSF).

Suitable excipients of the present invention include excipients or formularies that transport or help transport, but do not specifically target a composition to a cell or area (also referred to herein as non-targeting carriers). Examples of pharmaceutically acceptable excipients include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity. Compositions of the present invention can be sterilized by conventional methods and/or lyophilized.

One type of pharmaceutically acceptable carrier includes a controlled release formulation that is capable of slowly releasing a composition of the present invention into a patient or culture. As used herein, a controlled release formulation comprises a cysteine mutein of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, liposheres, and transdermal delivery systems. Other carriers of the present invention include liquids that, upon administration to a patient, form a solid or a gel in situ. Preferred carriers are also biodegradable (i.e., bioerodible). In the event that a cysteine mutein of the invention is administered as a recombinant nucleic acid molecule encoding the cysteine mutein (e.g., gene therapy or genetic immunization), suitable carriers include, but are not limited to liposomes, viral vectors or other carriers, including ribozymes, gold particles, poly-L-lysine/DNA-molecular conjugates, and artificial chromosomes. Natural lipid-containing carriers include cells and cellular membranes. Artificial lipid-containing carriers include liposomes and micelles.

A carrier of the present invention can be modified to target to a particular site in a patient, thereby targeting and making use of a compound of the present invention at that site. A pharmaceutically acceptable carrier which is capable of targeting can also be referred to herein as a "delivery vehicle" or "targeting carrier". Suitable modifications include manipulating the chemical formula of the lipid portion of the delivery vehicle and/or introducing into the vehicle a targeting agent capable of specifically targeting a delivery vehicle to a preferred site or target site, for example, a preferred cell type. A "target site" refers to a site in a patient to which one desires to deliver a composition. Suitable targeting compounds include ligands capable of selectively (i.e., specifically) binding another molecule at a particular site. Examples of such ligands include antibodies, antigens, receptors and receptor ligands. Manipulating the chemical formula of the lipid portion of the delivery vehicle can modulate the extracellular or intracellular targeting of the delivery vehicle. For example, a chemical can be added to the lipid formula of a liposome that alters the charge of the lipid bilayer of the liposome so that the liposome fuses with particular cells having particular charge characteristics.

One delivery vehicle of the present invention is a liposome. A liposome is capable of remaining stable in an animal for a sufficient amount of time to deliver a nucleic acid molecule or protein described in the present invention to a preferred site in the animal. A liposome, according to the present invention, comprises a lipid composition that is capable of delivering a nucleic acid molecule or protein to a particular, or selected, site in a patient. A liposome according to the present invention comprises a lipid composition that is capable of fusing with the plasma membrane of the targeted cell to deliver a nucleic acid molecule or protein into a cell. Suitable liposomes for use with the present invention include any liposome. Preferred liposomes of the present invention include those liposomes commonly used in, for example, gene delivery methods known to those of skill in the art. More preferred liposomes comprise liposomes having a polycationic lipid composition and/or liposomes having a cholesterol backbone conjugated to polyethylene glycol. Complexing a liposome with a nucleic acid molecule or protein of the present invention can be achieved using methods standard in the art.

Another type of delivery vehicle, when the cysteine mutein is administered as a nucleic acid encoding the mutein, comprises a viral vector. A viral vector includes an isolated nucleic acid molecule, in which the nucleic acid molecules are packaged in a viral coat that allows entrance of DNA into a cell. A number of viral vectors can be used, including, but not limited to, those based on alphaviruses, poxviruses, adenoviruses, herpesviruses, lentiviruses, adeno-associated viruses and retroviruses.

According to the present invention, an effective administration protocol (i.e., administering a therapeutic composition in an effective manner) comprises suitable dose parameters and modes of administration that result in the desired effect in the patient (e.g., stimulation of proliferation and/or differentiation of neutrophils), preferably so that the patient is protected from the disease (e.g., by disease prevention or by alleviating one or more symptoms of ongoing disease). Effective dose parameters can be determined using methods standard in the art for a particular disease. Such methods include, for example, determination of survival rates, side effects (i.e., toxicity) and progression or regression of disease.

In accordance with the present invention, a suitable single dose size is a dose that results in the desired therapeutic effect in the patient, depending on the cysteine mutein that is administered, or in the amelioration of at least one symptom of a condition in the patient, when administered one or more times over a suitable time period. Doses can vary depending upon the disease being treated. One of skill in the art can readily determine appropriate single dose sizes for a given patient based on the size of a patient and the route of administration.

In one aspect of the invention, a suitable single dose of a therapeutic composition of the present invention is an amount that, when administered by any route of administration, provides a therapeutic effect in the patient as described above, as compared to a patient which has not been administered with the therapeutic composition of the present invention (i.e., a control patient), as compared to the patient prior to administration of the composition, or as compared to a standard established for the particular disease, patient type and composition.

In one aspect of the invention an appropriate single dose of a cysteine mutein of the present invention is at least about 0.01 µg per kg of the animal to which the mutein is administered, and in other aspects, at least about 0.1 µg/kg, at least about 0.2 µg/kg, at least about 0.5µ µg/kg, at least about 1µ µg/kg, at least about 5 µg/kg, at least about 10 µg/kg, at least about 25 µg/kg, at least about 50 µg/kg, at least about 75 µg/kg, at least about 100 µg/kg, at least about 200 µg/kg, at least about 300 µg/kg, at least about 400 µg/kg, at least about 500 µg/kg, at least about 750 µg/kg, at least about 1 mg/kg, or at least about 5 mg/kg. In one embodiment, a preferred single dose of a GM-CSF cysteine mutein of the present invention is at least about 0.1 µg/kg, and more preferably, from about 25 to about 300 µg/kg. In one embodiment, a preferred single dose of an EPO cysteine mutein of the present invention is at least about 0.01 µg/kg, and more preferably, from about 1 to about 300 µg/kg. In one embodiment, a preferred single dose of a G-CSF cysteine mutein of the present invention is at least about 0.1 µg/kg, and more preferably, from about 1 to about 300 µg/kg. In one embodiment, a preferred single dose of an IFN-α cysteine mutein of the present invention is at least about 0.1 µg/kg, and more preferably, from about 1 to about 300 µg/kg.

As discussed above, a therapeutic composition of the present invention is administered to a patient in a manner effective to deliver the composition to a cell, a tissue, and/or systemically to the patient, whereby the desired result is achieved as a result of the administration of the composition. Suitable administration protocols include any in vivo or ex vivo administration protocol. The preferred routes of administration will be apparent to those of skill in the art, depending on the type of condition to be prevented or treated; whether the composition is nucleic acid based or protein based; and/or the target cell/tissue. For proteins or nucleic acid molecules, preferred methods of in vivo administration include, but are not limited to, intravenous administration, intraperitoneal administration, intramuscular administration, intranodal administration, intracoronary administration, intraarterial administration (e.g., into a carotid artery), subcutaneous administration, transdermal delivery, intratracheal administration, subcutaneous administration, intraarticular administration, intraventricular administration, inhalation (e.g., aerosol), intracranial, intraspinal, intraocular, intranasal, oral, bronchial, rectal, topical, vaginal, urethral, pulmonary administration, impregnation of a catheter, and direct injection into a tissue. Routes useful for deliver to mucosal tissues include, bronchial, intradermal, intramuscular, intranasal, other inhalatory, rectal, subcutaneous, topical, transdermal, vaginal and urethral routes. Combinations of routes of delivery can be used and in some instances, may enhance the therapeutic effects of the composition. Particularly preferred routes of delivery include subcutaneous and intravenous delivery.

Ex vivo administration refers to performing part of the regulatory step outside of the patient, such as administering a composition of the present invention to a population of cells removed from a patient under conditions such that the composition contacts and/or enters the cell, and returning the cells to the patient. Ex vivo methods are particularly suitable when the target cell type can easily be removed from and returned to the patient.

Many of the above-described routes of administration, including intravenous, intraperitoneal, intradermal, and intramuscular administrations can be performed using methods standard in the art. Aerosol (inhalation) delivery can also be performed using methods standard in the art (see, for example, Stribling et al., Proc. Natl. Acad. Sci. USA 189: 11277-11281, 1992, which is incorporated herein by reference in its entirety). Oral delivery can be performed by complexing a therapeutic composition of the present invention to a carrier capable of withstanding degradation by digestive enzymes in the gut of an animal. Examples of such carriers, include plastic capsules or tablets, such as those known in the art.

One method of local administration is by direct injection. Direct injection techniques are particularly useful for administering a composition to a cell or tissue that is accessible by surgery, and particularly, on or near the surface of the body. Administration of a composition locally within the area of a target cell refers to injecting the composition centimeters and preferably, millimeters from the target cell or tissue.

Various methods of administration and delivery vehicles disclosed herein have been shown to be effective for delivery of a nucleic acid molecule to a target cell, whereby the nucleic acid molecule transfected the cell and was expressed. In many studies, successful delivery and expression of a heterologous gene was achieved in preferred cell types and/or using preferred delivery vehicles and routes of administration of the present invention. All of the publications discussed below and elsewhere herein with regard to gene delivery and delivery vehicles are incorporated herein by reference in their entirety.

For example, using liposome delivery, U.S. Pat. No. 5,705, 151, issued Jan. 6, 1998, to Dow et al. demonstrated the successful in vivo intravenous delivery of a nucleic acid molecule encoding a superantigen and a nucleic acid molecule encoding a cytokine in a cationic liposome delivery vehicle, whereby the encoded proteins were expressed in tissues of the animal, and particularly in pulmonary tissues. In addition, Liu et al., *Nature Biotechnology* 15:167, 1997, demonstrated that intravenous delivery of cholesterol-containing cationic liposomes containing genes preferentially targets pulmonary tissues and effectively mediates transfer and expression of the genes in vivo. Several publications by Dzau and collaborators demonstrate the successful in vivo delivery and expression of a gene into cells of the heart, including cardiac myocytes and fibroblasts and vascular smooth muscle cells using both naked DNA and Hemagglutinating virus of Japan-liposome delivery, administered by both incubation within the pericardium and infusion into a coronary artery (intracoronary delivery) (See, for example, Aoki et al., 1997, *J. Mol. Cell, Cardiol.* 29:949-959; Kaneda et al., 1997, *Ann N.Y. Acad. Sci.* 811: 299-308; and von der Leyen et al., 1995, *Proc Natl Acad Sci USA* 92:1137-1141).

Delivery of numerous nucleic acid sequences has been accomplished by administration of viral vectors encoding the nucleic acid sequences. Using such vectors, successful delivery and expression has been achieved using ex vivo delivery (See, of many examples, retroviral vector; Blaese et al., 1995, *Science* 270:475-480; Bordignon et al., 1995, *Science* 270: 470-475), nasal administration (CFTR-adenovirus-associated vector), intracoronary administration (adenoviral vector and Hemagglutinating virus of Japan, see above), intravenous administration (adeno-associated viral vector; Koeberl et al., 1997, *Proc Natl Acad Sci USA* 94:1426-1431). A publication by Maurice et al. (1999, *J. Clin. Invest.* 104:21-29) demonstrated that an adenoviral vector encoding a β2-adrenergic receptor, administered by intracoronary delivery, resulted in diffuse multichamber myocardial expression of the gene in vivo, and subsequent significant increases in hemodynamic function and other improved physiological parameters. Levine et al. describe in vitro, ex vivo and in vivo delivery and expression of a gene to human adipocytes and rabbit adipocytes using an adenoviral vector and direct injection of the constructs into adipose tissue (Levine et al., 1998, *J. Nutr. Sci. Vitaminol.* 44:569-572).

In the area of neuronal gene delivery, multiple successful in vivo gene transfers have been reported. Millecamps et al. reported the targeting of adenoviral vectors to neurons using neuron restrictive enhancer elements placed upstream of the promoter for the transgene (phosphoglycerate promoter). Such vectors were administered to mice and rats intramuscularly and intracerebrally, respectively, resulting in successful neuronal-specific transfection and expression of the transgene in vivo (Millecamps et al., 1999, *Nat. Biotechnol.* 17:865-869). As discussed above, Bennett et al. reported the use of adeno-associated viral vector to deliver and express a gene by subretinal injection in the neural retina in vivo for greater than 1 year (Bennett, 1999, ibid.).

Gene delivery to synovial lining cells and articular joints has had similar successes. Oligino and colleagues report the use of a herpes simplex viral vector which is deficient for the immediate early genes, ICP4, 22 and 27, to deliver and express two different receptors in synovial lining cells in vivo (Oligino et al., 1999, *Gene Ther.* 6:1713-1720). The herpes vectors were administered by intraarticular injection. Kuboki et al. used adenoviral vector-mediated gene transfer and intraarticular injection to successfully and specifically express a gene in the temporomandibular joints of guinea pigs in vivo (Kuboki et al., 1999, *Arch. Oral. Biol.* 44:701-709). Apparailly and colleagues systemically administered adenoviral vectors encoding IL-10 to mice and demonstrated successful expression of the gene product and profound therapeutic effects in the treatment of experimentally induced arthritis (Apparailly et al., 1998, *J. Immunol.* 160:5213-5220). In another study, murine leukemia virus-based retroviral vector was used to deliver (by intraarticular injection) and express a human growth hormone gene both ex vivo and in vivo (Ghivizzani et al., 1997, *Gene Ther.* 4:977-982). This study showed that expression by in vivo gene transfer was at least equivalent to that of the ex vivo gene transfer. As discussed above, Sawchuk et al. has reported successful in vivo adenoviral vector delivery of a gene by intraarticular injection, and prolonged expression of the gene in the synovium by pretreatment of the joint with anti-T cell receptor monoclonal antibody (Sawchuk et al., 1996, ibid.). Finally, it is noted that ex vivo gene transfer of human interleukin-1 receptor antagonist using a retrovirus has produced high level intraarticular expression and therapeutic efficacy in treatment of arthritis, and is now entering FDA approved human gene therapy trials (Evans and Robbins, 1996, *Curr. Opin. Rheumatol.* 8:230-234). Therefore, the state of the art in gene therapy has led the FDA to consider human gene therapy an appropriate strategy for the treatment of at least arthritis. Taken together, all of the above studies in gene therapy indicate that delivery and expression of a recombinant nucleic acid molecule according to the present invention is feasible.

Another method of delivery of recombinant molecules is in a non-targeting carrier (e.g., as "naked" DNA molecules, such as is taught, for example in Wolff et al., 1990, *Science* 247, 1465-1468). Such recombinant nucleic acid molecules are typically injected by direct or intramuscular administration. Recombinant nucleic acid molecules to be administered by naked DNA administration include an isolated nucleic acid molecule of the present invention, and preferably includes a recombinant molecule of the present invention that preferably is replication, or otherwise amplification, competent. A naked nucleic acid reagent of the present invention can comprise one or more nucleic acid molecules of the present invention including a dicistronic recombinant molecule. Naked nucleic acid delivery can include intramuscular, subcutaneous, intradermal, transdermal, intranasal and oral routes of administration, with direct injection into the target tissue being most preferred. A preferred single dose of a naked nucleic acid vaccine ranges from about 1 nanogram (ng) to about 100 µg, depending on the route of administration and/or method of delivery, as can be determined by those skilled in the art. Suitable delivery methods include, for example, by injection, as drops, aerosolized and/or topically. In one embodiment, pure DNA constructs cover the surface of gold particles (1 to 3 µm in diameter) and are propelled into skin cells or muscle with a "gene gun."

In the method of the present invention, compositions can be administered to any animal and preferably, to any member of the Vertebrate class, Mammalia, including, without limitation, primates, rodents, livestock and domestic pets. Livestock include mammals to be consumed or that produce useful products (e.g., sheep for wool production). Preferred mammals to protect include humans, dogs, cats, mice, rats, sheep, cattle, horses and pigs, with humans being particularly preferred.

The following examples are provided to demonstrate how the "rules" described herein can be used to create cysteine-added variants of GH, erythropoietin, alpha interferon, beta interferon, G-CSF, GM-CSF and other members of the GH supergene family. The examples also demonstrate the therapeutic uses of cysteine variants of the present invention. The examples are not intended to be limiting, but only exemplary of specific embodiments of the invention.

EXAMPLE 1

Cysteine-Added Variants of GH

This example discloses certain amino acids in GH that are non-essential for biological activity and which, when mutated to cysteine residues, will not alter the normal disulfide binding pattern and overall conformation of the molecule. These amino acids are located at the N-terminal end of the A-B loop (amino acids 34-52 of the mature protein sequence; SEQ ID NO: 1; Martial et al 1979; Goeddel et al 1979), the B-C loop (amino acids 97-105 in the mature protein sequence), and the C-D loop (amino acids 130-153 in the mature protein sequence). Also identified as preferred sites for introducing cysteine residues are the first three or last three amino acids in the A, B, C and D helices and the amino acids proximal to helix A (amino acids 1-5) and distal to helix D (amino acids 184-191). Helix A encompasses amino acids 6-33, helix B encompasses amino acids 75-96, helix C encompasses amino acids 106-129 and helix D encompasses amino acids 154-183. The entire A-B loop encompasses amino acids 34-74.

DNA sequences encoding wild type GH can be amplified using the polymerase chain reaction technique from commercially available single-stranded cDNA prepared from human pituitaries (ClonTech, San Diego, Calif.) or assembled using overlapping oligonucleotides. Specific mutations can be introduced into the GH sequence using a variety of procedures such as phage techniques (Kunkel et al 1987), PCR mutagenesis techniques (Innis et al 1990; White 1993) mutagenesis kits such as those sold by Stratagene ("Quick-Change Mutagenesis" kit, San Diego, Calif.) or Promega (Gene Editor Kit, Madison Wis.).

Cysteine substitutions can be introduced into any of the amino acids comprising the B-C loop, C-D loop and N-terminal end of the A-B loop or into the first three amino acids of the alpha helical regions that adjoin these regions. or in the region proximal to helix A or distal to helix D. Preferred sites for introduction of cysteine residues are: F1, T3, P5, E33, A34, K38, E39, Q40, S43, Q46, N47, P48, Q49, T50, S51, S55, T60, A98, N99, S100, G104, A105, S106, E129, D130, G131, S132, P133, T135, G136, Q137, K140, Q141, T142, S144, K145, D147, T148, N149, S150, H151, N152, D153, S184, E186, G187, S188, and G190. Cysteine residues also can be introduced at the beginning of the mature protein, i.e., proximal to the F1 amino acid, or following the last amino acid in the mature protein, i.e., following F191. If desirable, two or more such mutations can be readily combined in the same protein either by in vitro DNA recombination of cloned mutant genes and/or sequential construction of individual desired mutations.

1. Cloning the Gene for Human Growth Hormone (GH)

The human GH gene was amplified from human pituitary single-stranded cDNA (commercially available from CLONTECH, Inc., Palo Alto, Calif.) using the polymerase chain reaction (PCR) technique and primers BB1 and BB2. The sequence of BB1 is 5'-GGGGGTCGACCATATGTTC-CCAACCATTCCCTTATCCAG-3' (SEQ ID NO: 24). The sequence of BB2 is 5'-GGGGGATCCTCACTAGAAGCCA-CAGCTGCCCTC-3' (SEQ ID NO: 25). Primer BB1 was designed to encode an initiator methionine preceding the first amino acid of mature GH, phenylalanine, and SalI and NdeI sites for cloning purposes. The reverse primer, BB2, contains a BamHI site for cloning purposes. The PCR 100 microliter reactions contained 20 pmoles of each oligonucleotide primer, 1× PCR buffer (Perkin-Elmer buffer containing $MgCl_2$), 200 micromolar concentration of each of the four nucleotides dA, dC, dG and dT, 2 ng of single-stranded cDNA, 2.5 units of Taq polymerase (Perkin-Elmer) and 2.5 units of Pfu polymerase (Stratagene, Inc). The PCR reaction conditions were 96° C. for 3 minutes, 35 cycles of (95° C., 1 minute; 63° C. for 30 seconds; 72° C. for 1 minute), followed by 10 minutes at 72° C. The thermocycler employed was the Amplitron II Thermal Cycler (Thermolyne). The approximate 600 by PCR product was digested with SalI and BamHI, gel purified and cloned into similarly digested plasmid pUC19 (commercially available from New England BioLabs, Beverly, Mass.). The ligation mixture was transformed into E. coli strain DH5alpha and transformants selected on LB plates containing ampicillin. Several colonies were grown overnight in LB media and plasmid DNA isolated using miniplasmid DNA isolation kits purchased from Qiagen, Inc (Valencia, Calif.). Clone LB6 was determined to have the correct DNA sequence.

For expression in E. coli, clone LB6 was digested with NdeI and EcoRI, the approximate 600 by fragment gel-purified, and cloned into plasmid pCYB1 (commercially available from New England BioLabs, Beverly, Mass.) that had been digested with the same enzymes and phosphatased. The ligation mixture was transformed into E. coli DH5alpha and transformants selected on LB ampicillin plates. Plasmid DNA was isolated from several transformants and screened by digestion with NdeI and EcoRI. A correct clone was identified and named pCYB1: wtGH (pBBT120). This plasmid was transformed into E. coli strains JM109 or W3110 (available from New England BioLabs and the American Type Culture Collection).

2. Construction of STII-GH

Wild type GH clone LB6 (pUC19: wild type GH) was used as the template to construct a GH clone containing the E. coli STII signal sequence (Picken et al. 1983). Because of its length, the STII sequence was added in two sequential PCR reactions. The first reaction used forward primer BB12 and reverse primer BB10. BB10 has the sequence:

(SEQ ID NO: 28)
5'CGCGGATCCGATTAGAATCCACAGCTCCCCTC 3'.

BB12 has the sequence:

(SEQ ID NO: 30)
5'ATCTATGTTCGTTTTCTCTATCGCTACCAACGCTTACGCATTCCCAAC

CATTCCCTTATCCAG-3'.

The PCR reactions were as described for amplifying wild type GH except that approximately 4 ng of plasmid LB6 was used as the template rather than single-stranded cDNA and the PCR conditions were 96° C. for 3 minutes, 30 cycles of (95° C. for 1 minute; 63° C. for 30 seconds; 72° C. for 1 minute) followed by 72° C. for 10 minutes. The approximate 630 by PCR product was gel-purified using the Qiaex II Gel Extraction Kit (Qiagen, Inc), diluted 50-fold in water and 2 microliters used as template for the second PCR reaction. The second PCR reaction used reverse primer BB10 and forward primer BB11. BB11 has the sequence:

(SEQ ID NO: 29)
5'CCCCCTCTAGACATATGAAGAAGAACATCGCATTCCTGCTGGCATC

TATGTTCGTTTTCTCTATCG-3'.

Primer BB11 contains XbaI and NdeI sites for cloning purposes. PCR conditions were as described for the first reaction. The approximate 660 by PCR product was digested with XbaI and BamHI, gel-purified and cloned into similarly cut plasmid pCDNA3.1(+) (Invitrogen, Inc. Carlsbad, Calif.). Clone pCDNA3.1(+)::stII-GH(5C) or "5C" was determined to have the correct DNA sequence.

Clone "5C" was cleaved with NdeI and BamHI and cloned into similarly cut pBBT108 (a derivative of pUC19 which lacks a Pst I site, this plasmid is described below). A clone with the correct insert was identified following digestion with these enzymes. This clone, designated pBBT111, was digested with NdeI and SalI, the 660 by fragment containing the stII-GH fusion gene, was gel-purified and cloned into the plasmid expression vector pCYB1 (New England BioLabs) that had been digested with the same enzymes and phosphatased. A recombinant plasmid containing the stII-GH insertion was identified by restriction endonuclease digestions. One such isolate was chosen for further studies and was designated pBBT114. This plasmid was transformed into E. coli strains JM109 or W3110 (available from New England BioLabs and the American Type Culture Collection).

3. Construction of ompA-GH

Wild type GH clone LB6 (pUC19: wild type GH) was used as the template to construct a GH clone containing the E. coli ompA signal sequence (Movva et al 1980). Because of its length, the ompA sequence was added in two sequential PCR reactions. The first reaction used forward primer BB7:

(SEQ ID NO: 31)
5'GCAGTGGCACTGGCTGGTTTCGCTACCGTAGCGCAGGCCTTCCCAA

CCATTCCCTTATCCAG 3', and reverse primer BB10:

(SEQ ID NO: 28)
5' CGCGGATCCGATTAGAATCCACAGCTCCCCTC 3'.

The PCR reactions were as described for amplifying wild type GH except that approximately 4 ng of plasmid LB6 was used as the template rather than single-stranded cDNA and the PCR conditions were 96° C. for 3 minutes, 30 cycles of (95° C. for 1 minute; 63° C. for 30 seconds; 72° C. for 1 minute) followed by 72° C. for 10 minutes. The approximate 630 by PCR product was gel-purified using the Qiaex II Gel Extraction Kit (Qiagen, Inc), diluted 50-fold in water and 2 microliters used as template for the second PCR reaction. The second PCR reaction used reverse primer BB10 and forward Primer BB6:

(SEQ ID NO: 32)
5'CCCCGTCGACACATATGAAGAAGACAGCTATCGCGATTGCAGTGGC
ACTGGCTGGTTTC 3'.

PCR conditions were as described for the first reaction. The approximate 660 by PCR product was gel-purified, digested with Sal I and Bam H1 and cloned into pUC19 (New England BioLabs) which was cut with Sal I and Bam H1 or pCDNA3.1 (+) (Invitrogen) which had been cut by Xho I and Bam H1 (Sal I and Xho I produce compatible single-stranded overhangs). When several clones were sequenced, it was discovered that all pUC19 clones (8/8) contained errors in the region of the ompA sequence. Only one pCDNA3.1(+) clone was sequenced and it contained a sequence ambiguity in the ompA region. In order to generate a correct ompA-GH fusion gene segments of two sequenced clones which contained different errors separated by a convenient restriction site were recombined and cloned into the pUC19-derivative that lacks the Pst I site (see pBBT108 described below). The resulting plasmid, termed pBBT112, carries the ompA-GH fusion gene cloned as an Nde I-Bam H1 fragment into these same sites in pBBT108. This plasmid is designated pBBT112 and is used in PCR-based, site-specific mutagenesis of GH as described below.

4. Construction of Pst- pUC19

To facilitate mutagenesis of the cloned GH gene for construction of selected cysteine substitution and insertion mutations a derivative of the plasmid pUC19 (New England BioLabs) lacking a Pst I site was constructed as follows. pUC19 plasmid DNA was digested with Pst I and subsequently treated at 75 deg. C. with PFU DNA Polymerase (Stratagene) using the vendor-supplied reaction buffer supplemented with 200 uM dNTPs. Under these conditions the polymerase will digest the 3' single-stranded overhang created by Pst I digestion but will not digest into the double-stranded region. The net result will be the deletion of the 4 single-stranded bases which comprise the middle four bases of the Pst I recognition site. The resulting molecule has double-stranded, i.e., "blunt", ends. Following these enzymatic reactions, the linear monomer was gel-purified using the Qiaex II Gel Extraction Kit (Qiagen, Inc). This purified DNA was treated with T4 DNA Ligase (New England BioLabs) according to the vendor protocols, digested with Pst I, and used to transform E coli DH5alpha. Transformants were picked and analyzed by restriction digestion with Pst I and Bam H1. One of the transformants which was not cleaved by Pst I but was cleaved at the nearby Bam H1 site was picked and designated pBBT108.

5. Construction of GH Muteins

GH muteins were generally constructed using site-directed PCR-based mutagenesis as described in PCR Protocols: Current Methods and Applications edited by B. A. White, 1993 Humana Press, Inc., Totowa, N.J. and PCR Protocols: A Guide to Methods and Applications edited by Innis, M. A. et al 1990 Academic Press Inc San Diego, Calif. Typically PCR primer oligonucleotides are designed to incorporate nucleotide changes to the coding sequence of GH that result in substitution of a cysteine residue for an amino acid at a specific position within the protein. Such mutagenic oligonucleotide primers can also be designed to incorporate an additional cysteine residue at the carboxy terminus or amino terminus of the coding sequence of GH. In this latter case one or more additional amino acid residues could also be incorporated at the amino terminal and/or carboxy terminal to the added cysteine residue if that were desirable. Moreover, oligonucleotides can be designed to incorporate cysteine residues as insertion mutations at specific positions within the GH coding sequence if that were desirable. Again, one or more additional amino acids could be inserted along with the cysteine residue and these amino acids could be positioned at the amino terminal and/or carboxy terminal to the cysteine residue.

The cysteine substitution mutation T135C was constructed as follows. The mutagenic reverse oligonucleotide BB28:

(SEQ ID NO: 33)
5'CTGCTTGAAGATCTGCCCACACCGGGGGCTGCCATC3' was designed to change the codon ACT for threonine at amino acid residue 135 to a TGT codon encoding cysteine and to span the nearby Bgl II site. This oligonucleotide was used in PCR along with the forward oligonucleotide BB34 5'GTAGCGCAGGCCTTCCCAACCATT3' (SEQ ID NO: 34) which anneals to the junction region of the ompA-GH fusion gene and is not mutagenic. The PCR was performed in a 50 ul reaction in 1× PCR buffer (Perkin-Elmer buffer containing 1.5 mM $MgCl_2$), 200 micromolar concentration of each of the four nucleotides dA, dC, dG and dT, with each oligonucleotide primer present at 0.5 µM, 5 pg of pBBT112 (described above) as template and 1.25 units of Amplitac DNA Polymerase (Perkin-Elmer) and 0.125 units of PFU DNA Polymerase (Stratagene). Reactions were performed in a Robocycler Gradient 96 thermal cycler (Stratagene). The program used entailed: 95 deg C. for 3 minutes followed by 25 cycles of 95 deg C. for 60 seconds, 45 deg C. or 50 deg C. or 55 deg C. for 75 seconds, 72 deg C. for 60 seconds followed by a hold at 6 deg C. The PCR reactions were analyzed by agarose gel electrophoresis to identify annealing temperatures that gave significant product of the expected size; ~430 bp. The 45-deg C. reaction was "cleaned up" using the QIAquick PCR Purification Kit (Qiagen), digested with Bgl II and Pst I. The resulting 278 by Bgl II-Pst I fragment, which includes the putative T135C mutation, was gel-purified and ligated into pBBT111 the pUC19 derivative carrying the stII-GH fusion gene (described above) which had been digested with Bgl II and Pst I and gel-purified. Transformants from this ligation were initially screened by digestion with Bgl II and Pst I and subsequently one clone was sequenced to confirm the presence of the T135C mutation and the absence of any additional mutations that could potentially be introduced by the PCR reaction or by the synthetic oligonucleotides. The sequenced clone was found to have the correct sequence.

The substitution mutation S 132C was constructed using the protocol described above for T135C with the following differences: mutagenic reverse oligonucleotide BB29 5'CTGCTTGAAGATCTGCCCAGTC-CGGGGGCAGCCATCTTC3' (SEQ ID NO: 35) was used instead of BB28 and the PCR reaction with annealing temperature of 50 deg C. was used for cloning. One of two clones sequenced was found to have the correct sequence.

The substitution mutation T148C was constructed using an analogous protocol but employing a different cloning strategy. The mutagenic forward oligonucleotide BB30 5'GGGCAGATCTTCAAGCAGACCTACAG-CAAGTTCGACTGCAACTCACACAAC 3' (SEQ ID NO: 36) was used in PCR with the non-mutagenic reverse primer BB33 5'CGCGGTACCCGGGATCCGATTAGAATC-CACAGCT3' (SEQ ID NO: 37) which anneals to the most 3' end of the GH coding sequence and spans the Bam H1 site immediately downstream. PCR was performed as described above with the exception that the annealing temperatures used were 46, 51 and 56 deg C. Following PCR and gel analysis as described above the 46 and 51 deg C. reactions were pooled for cloning. These were digested with Bam H1 and Bgl II, gel-purified and cloned into pBBT111 which had been digested with Bam H1 and Bgl II, treated with Calf intestinal Alkaline Phosphatase (Promega) according to the vendor protocols, and gel-purified. Transformants from this ligation were analyzed by digestion with Bam H1 and Bgl II to identify clones in which the 188 by Bam H1-Bgl II mutagenic PCR fragment was cloned in the proper orientation. Because Bam H1 and Bgl II generate compatible ends, this cloning step is not orientation specific. Five of six clones tested were shown to be correctly oriented. One of these was sequenced and was shown to contain the desired T148C mutation. The sequence of the remainder of the 188 by Bam H1-Bgl II mutagenic PCR fragment in this clone was confirmed as correct.

The construction of the substitution mutation S144C was identical to the construction of T148C with the following exceptions. Mutagenic forward oligonucleotide BB31 5' GGGCAGATCTTCAAGCAGACCTACTG-CAAGTTCGAC3' (SEQ ID NO: 38) was used instead of BB30. Two of six clones tested were shown to be correctly oriented. One of these was sequenced and was shown to contain the desired S144C mutation. The sequence of the remainder of the 188 by Bam H1-Bgl II mutagenic PCR fragment in this clone was confirmed as correct.

A mutation was also constructed that added a cysteine residue to the natural carboxy terminus of GH. The construction of this mutation, termed stp192C, was similar to that of T148C, but employed different oligonucleotide primers. The reverse mutagenic oligonucleotide:

(SEQ ID NO: 39)
BB32
5'CGCGGTACCGGATCCTTAGCAGAAGCCACAGCTGCCCTCCAC3' which inserts a TGC codon for cysteine between the codon for the carboxy terminal phe residue of GH and the TAA translational stop codon and spans the nearby Bam H1 site was used along with BB34 5'GTAGCGCAGGCCTTC-CCAACCATT3' (SEQ ID NO: 40) which is described above. Following PCR and gel analysis as described above, the 46 deg C. reaction was used for cloning. Three of six clones tested were shown to be correctly oriented. One of these was sequenced and was shown to contain the desired stp192C mutation. The sequence of the remainder of the 188 by Bam H1-Bgl II mutagenic PCR fragment in this clone was confirmed as correct.

Analogous PCR mutagenesis procedures can be used to generate other cysteine mutations. The choice of sequences for mutagenic oligonucleotides will be dictated by the position where the desired cysteine residue is to be placed and the propinquity of useful restriction endonuclease sites. Generally, it is desirable to place the mutation, i.e., the mismatched segment near the middle of the oligonucleotide to enhance the annealing of the oligonucleotide to the template. Appropriate annealing temperatures for any oligonucleotide can be determined empirically. It is also desirable for the mutagenic oligonucleotide to span a unique restriction site so that the PCR product can be cleaved to generate a fragment that can be readily cloned into a suitable vector, e.g., one that can be used to express the mutein or provides convenient restriction sites for excising the mutated gene and readily cloning it into such an expression vector. Sometimes mutation sites and restriction sites are separated by distances that are greater than that which is desirable for synthesis of synthetic oligonucleotides: it is generally desirable to keep such oligonucleotides under 80 bases in length and lengths of 30-40 bases are more preferable.

In instances where this is not possible, genes targeted for mutagenesis could be re-engineered or re-synthesized to incorporate restriction sites at appropriate positions. Alternatively, variations of PCR mutagenesis protocols employed above, such as the so-called "Megaprimer Method" (Barik, S., pp. 277-286 in Methods in Molecular Biology, Vol. 15: PCR Protocols: Current Methods and Applications edited by B. A. White, 1993, Humana Press, Inc., Totowa, N.J.) or "Gene Splicing by Overlap Extension" (Horton, R. M., pp. 251-261, in Methods in Molecular Biology, Vol. 15: PCR Protocols: Current Methods and Applications, edited by B. A. White, 1993, Humana Press, Inc., Totowa, N.J.) can also be employed to construct such mutations.

6. Expression of GH in pCYB1

To express GH in *E. coli*, pBBT120 (GH gene with no leader sequence cloned into the tac expression vector pCYB1) and pBBT114 (GH gene with stII leader sequence cloned into the tac expression vector pCYB1) were transformed into *E. coli* strains JM109 and W3110. The parental vector pCYB1 was also transformed into JM109 and W3110. These strains were given the following designations:

| | |
|---|---|
| BOB119: | JM109 (pCYB1) |
| BOB130: | W3110 (pCYB1) |
| BOB129: | JM109 (pBBT120) |
| BOB133: | W3110 (pBBT120) |
| BOB121: | JM109 (pBBT114) |
| BOB132: | W3110 (pBBT114) |

For expression, strains were grown overnight at 37° C. in Luria Broth (LB) (Sambrook, et al 1989) containing 100 µg/ml ampicillin. These saturated overnight cultures were diluted to ~0.03 OD at $A_{600}$ in LB containing 100 µg/ml ampicillin and incubated at 37° C. in shake flasks in rotary shaker, typically at 250-300 rpm. ODs were monitored and IPTG was added to a final concentration of 0.5 mM when culture ODs reached ~0.25 -0.5, typically between 0.3 and 0.4. Cultures were sampled typically at 1, 3, 5 and ~16 h post-induction. The "~16 h" time points represented overnight incubation of the cultures and exact times varied from ~15-20 h. Samples of induced and uninduced cultures were pelleted by centrifugation, resuspended in 1× sample buffer (50 mM Tris-HCl (pH 6.8), 2% sodium lauryl sulfate, 10% glycerol, 0.1% bromphenol blue) with the addition of 1% β-mercaptoethanol when desirable. Samples were boiled for ~10 minutes or heated to 95° C. for ~10 minutes. Samples were cooled to room temperature before being loaded onto SDS polyacrylamide gels or were stored at −20° C. if not run immediately. Samples were run on precast 15% polyacrylamide "Ready Gels" (Bio-Rad, Hercules Calif.) using a Ready Gel Cell electrophoresis apparatus (Bio-Rad) according to the vendor protocols. Typically gels were run at 200 volts for ~35-45 minutes. Gels were stained with Coomassie Blue or were analyzed by Western Blot following electro-blotting. Coomassie staining of whole cell lysates from strains BOB 129, BOB 133, BOB 121 and BOB 132 showed a band of ~22 kD that co-migrated with purified recombinant human GH standard purchased from Research Diagnostics Inc (Flanders, N.J.). That band was most prominent in induced cultures following overnight induction. However, a band was also observed at that molecular weight in uninduced cultures of these same strains and could also be observed with and without induction in the BOB 119 and BOB 130 control strains that carried the expression vector pCYB1 lacking the GH gene. To clarify this observation, Western Blot analyses were performed on whole cell lysates of induced cultures of strains BOB119, BOB130, BOB129, BOB133, BOB121, and BOB132. Western blots were performed with polyclonal rabbit anti-human GH antiserum purchased from United States Biological; catalogue #G 9000-11 (Swampscott, Mass.) This primary antibody was used at a 1:5000 dilution and its binding was detected with goat anti-rabbit IgG Fc conjugated to alkaline phosphatase, (product #31341) purchased from Pierce (Rockford, Ill.). This secondary antibody was used at a 1:10,0000 dilution. Alkaline phosphatase activity was detected using the ImmunoPure® Fast Red TR/AS-MX Substrate Kit (Pierce, Rockford Ill.) according to the vendor protocols. The Western Blots clearly demonstrated presence of GH in lysates of induced cultures of BOB129, BOB133, BOB121, and BOB132 at both 3 and 16 h post-induction. In the induced culture of control strains, BOB119 and BOB130, no GH was detected by Western blot at 3 or 16 h post-induction time points.

In these preliminary experiments, the highest yields of GH were obtained from BOB132 W3110(pBBT114) in which the GH gene is fused downstream of the stII secretion signal sequence. This strain was tested further to determine if the GH protein was secreted to the periplasm as would be expected. An induced culture of BOB132 was prepared as described above and subjected to osmotic shock according to the procedure of Koshland and Botstein (Cell 20 (1980) pp. 749-760). This procedure ruptures the outer membrane and releases the contents of the periplasm into the surrounding medium. Subsequent centrifugation separates the periplasmic contents, present in the supernatant from the remainder of the cell-associated components. In this experiment, the bulk of the GH synthesized by BOB132 was found to be localized to the periplasm. This result is consistent with the finding that the bulk of the total GH is also indistinguishable in size from the purified GH standard, which indicated that the stII signal sequence had been removed. This is indicative of secretion. A larger scale (500 ml) culture of BOB132 was also induced, cultured overnight and subjected to osmotic shock according to the procedure described by Hsiung et al, 1986 (Bio/Technology 4, pp. 991-995). Gel analysis again demonstrated that the bulk of the GH produced was soluble, periplasmic, and indistinguishable in size from the GH standard. This material could also be quantitatively bound to, and eluted from, a Q-Sepharose column using conditions very similar to those described for recombinant human GH by Becker and Hsiung, 1986 (FEBS Lett 204 pp 145-150).

7. Cloning the Human GH Receptor

The human GH receptor was cloned by PCR using forward primer BB3 and reverse primer BB4. BB3 has the sequence:

(SEQ ID NO: 26)
5'-CCCCGGATCCGCCACCATGGATCTCTGGCAGCTGCTGTT-3'.

BB4 has the Sequence:

(SEQ ID NO: 27)
5'CCCCGTCGACTCTAGAGCTATTAAATACGTAGCTCTTGGG-3'.

The template was single-stranded cDNA prepared from human liver (commercially available from CLONTECH Laboratories). Primers BB3 and BB4 contain BamHI and SalI restriction sites, respectively, for cloning purposes. The 100 μl PCR reactions contained 2.5 ng of the single-stranded cDNA and 20 picomoles of each primer in 1× PCR buffer (Perkin-Elmer buffer containing $MgCl_2$), 200 micromolar concentration of each of the four nucleotides dA, dC, dG and dT, 2.5 units of Taq polymerase (Perkin-Elmer) and 2.5 units of Pfu polymerase (Stratagene, Inc). The PCR reaction conditions were: 96° C. for 3 minutes, 35 cycles of (95° C., 1 minute; 58° C. for 30 seconds; 72° C. for 2 minutes), followed by 10 minutes at 72° C. The thermocycler employed was the Amplitron II Thermal Cycler (Thermolyne). The approximate 1.9 kb PCR product was digested with BamHI and SalI and ligated with similarly cut plasmid pUC19 (New England BioLabs). However, none of the transformants obtained from this ligation reaction contained the 1.9 kb PCR fragment. Leung et al (Nature 1987 330 pp 537-543) also failed to obtain full-length cDNA clones of the human GH receptor in pUC19. Subsequently the PCR fragment was cloned into a low copy number vector, pACYC184 (New England BioLabs) at the BamHI and SalI sites in this vector. Such clones were obtained at reasonable frequencies but *E coli* strains carrying the cloned PCR fragment grew poorly, forming tiny and heterogeneous looking colonies, in the presence of chloramphenicol, which is used to select for maintenance of pACYC184.

The PCR fragment was simultaneously cloned into pCDNA3.1 (+) (Invitrogen). The approximate 1.9 kb PCR product was digested with BamHI and SalI and ligated into the BamHI and XhoI cloning sites of pCDNA3.1 (+). Only infrequent transformants from this ligation contained the cloned GH receptor cDNA and all of those were found to contain deletions of segments of the receptor coding sequence. One of these clones was sequenced and found to contain a deletion of 135 by within the GH receptor coding sequence: the sequence of the rest of the gene was in agreement with that reported by Leung et at (1987).

8. Cloning the Rabbit GH Receptor

The rabbit GH receptor was cloned by PCR using forward primer BB3 (described above) and reverse primer BB36. BB36 has the sequence (SEQ ID NO: 41)
5'CCCCGTCGACTCTAGAGCCATTAGATACAAAGCTCTTGGG3' and contains XbaI and Sal I restriction sites for cloning purposes. Rabbit liver poly(A)+ mRNA was purchased from CLONTECH, Inc. and used as the substrate in first strand synthesis of single-stranded cDNA to produce template for PCR amplification. First strand synthesis of single-stranded cDNA was accomplished using a 1st Strand cDNA Synthesis Kit for RT-PCR (AMV) kit from Boehringer Mannheim Corp (Indianapolis, Ind.) according to the vendor protocols. Parallel first strand cDNA syntheses were performed using random hexamers or BB36 as the primer. Subsequent PCR reactions with the products of the first strand syntheses as templates, were carried out with primers BB3 and BB36 according to the 1st Strand cDNA Synthesis Kit for RT-PCR (AMV) kit protocol and using 2.5 units of Amplitac DNA Polymerase (Perkin-Elmer) and 0.625 units of Pfu DNA Polymerase (Stratagene). The PCR reaction conditions were 96° C. for 3 minutes, 35 cycles of (95° C., 1 minute; 58° C. for 30 seconds; 72° C. for 2 minutes), followed by 10 minutes at 72° C. The thermocycler employed was the Amplitron II Thermal Cycler (Thermolyne). The expected ~1.9 kb PCR product was observed in PCR reactions using random hexamer-primed or BB36 primed cDNA as template. The random hexamer-primed cDNA was used in subsequent cloning experiments. It was digested with Bam H1 and XbaI and run out over a 1.2% agarose gel. This digest generates two fragments (~365 by and ~1600 bp) because the rabbit GH receptor gene contains an internal Bam H1 site. Both fragments were gel-purified. Initially the ~1600 by Bam H1-XbaI fragment was cloned into pCDNA3.1(+) which had been digested with these same two enzymes. These clones were readily obtained at reasonable frequencies and showed no evidence of deletions as determined by restriction digests and subsequent sequencing. To generate a full length clone, one of the plasmids containing the 1600 by Bam H1-Xba I fragment (pCDNA3.1(+):: rabghr-2A) was digested with Bam H1, treated with Calf Intestinal Alkaline Phosphatase (Promega) according to the vendor protocols, gel-purified and ligated with the gel purified ~365 by Bam H1 fragment that contains the 5' portion of the rabbit GH receptor gene. Transformants from this ligation were picked and analyzed by restriction digestion and PCR to confirm the presence of the ~365 by fragment and to determine its orientation relative to the distal segment of the rabbit GH receptor gene. Three out of four clones analyzed were found to contain the ~365 by fragment cloned in the correct orientation for reconstitution of the rabbit GH receptor gene. The lack of complications in the cloning in E coli of the rabbit gene, in contrast to the human gene, is consistent with the results of Leung et al (1987) who also readily obtained full length cDNA clones for the rabbit GH receptor gene but were unable to clone a full length cDNA of the human gene in E coli. The rabbit GH receptor can be employed in assays with human GH as a ligand as it has been shown that the human GH binds the rabbit receptor with high affinity (Leung et al 1987). Plasmids containing the cloned rabbit GH receptor should be sequenced to identify a rabbit GH receptor cDNA with the correct sequence before use.

9. Construction of a Human/Rabbit Chimeric GH Receptor Gene

As an alternative to the rabbit receptor, a chimeric receptor could be constructed which combines the extracellular domain of the human receptor with the transmembrane and cytoplasmic domains of the rabbit receptor. Such a chimeric receptor could be constructed by recombining the human and rabbit genes at the unique Nco I site that is present in each (Leung et al 1987). Such a recombinant, containing the human gene segment located 5' to, or "upstream" of the Nco I site and the rabbit gene segment 3' to, or "downstream" of the Nco I site would encode a chimeric receptor of precisely the desired type, having the extracellular domain of the human receptor with the transmembrane and cytoplasmic domains of the rabbit receptor. This would allow analysis of the interaction of GH, GH muteins, and PEGylated GH muteins with the natural receptor binding site but could avoid the necessity of cloning the full length human GH receptor in E coli.

The GH muteins can be expressed in a variety of expression systems such as bacteria, yeast or insect cells. Vectors for expressing GH muteins in these systems are available commercially from a number of suppliers such as Novagen, Inc. (pET15b for expression in E. coli), New England Biolabs (pC4B1 for expression in E. coli) Invitrogen (pVL1392, pVL1393, and pMELBAC for expression in insect cells using Baculovirus vectors, Pichia vectors for expression in yeast cells, and pCDNA3 for expression in mammalian cells). GH has been successfully produced in E. coli as a cytoplasmic protein and as a secreted, periplasmic, protein using the E. coli OmpA or STII signal sequences to promote secretion of the protein into the periplasmic space (Chang et al., 1987; Hsiung et al., 1986). It is preferable that the GH muteins are expressed as secreted proteins so that they do not contain an N-terminal methionine residue, which is not present in the natural human protein. For expression in E. coli, DNA sequences encoding GH or GH muteins can be cloned into E. coli expression vectors such as pET15b that uses the strong T7 promoter or pCYB1 that uses the TAC promoter. Adding IPTG (isopropylthiogalactopyranoside, available form Sigma Chemical Company) to the growth media, can induce expression of the protein. Recombinant GH will be secreted into the periplasmic space from which it can be released by, and subsequently purified, following osmotic shock (Becker and Hsiung, 1986). The protein can be purified further using other chromatographic methods such as ion-exchange, hydrophobic interaction, size-exclusion and reversed phase chromatography, all of which are well known to those of skill in the art (e.g., see Becker and Hsiung, 1986). Protein concentrations can be determined using commercially available protein assay kits such as those sold by BioRad Laboratories (Richmond, Calif.). If the GH proteins are insoluble when expressed in E. coli they can be refolded using procedures well known to those skilled in the art (see Cox et al., 1994 and World patent applications WO9422466 and WO9412219).

Alternatively, the proteins can be expressed in insect cells as secreted proteins. The expression plasmid can be modified to contain the GH signal sequence to promote secretion of the protein into the medium. The cDNAs can be cloned into commercially available vectors, e.g., pVL1392 from Invitrogen, Inc., and used to infect insect cells. The GH and GH muteins can be purified from conditioned media using conventional chromatography procedures. Antibodies to rhGH can be used in conjunction with Western blots to localize fractions containing the GH proteins during chromatography. Alternatively, fractions containing GH can be identified using ELISA assays.

The cysteine-added GH variants also can be expressed as intracellular or secreted proteins in eukaryotic cells such as yeast, insect cells or mammalian cells. Vectors for expressing the proteins and methods for performing such experiments are described in catalogues from various commercial supply companies such as Invitrogen, Inc., Stratagene, Inc. and ClonTech, Inc. The GH and GH muteins can be purified using conventional chromatography procedures.

Biological activity of the GH muteins can be measured using a cell line that proliferates in response to GH. Fuh et al. (1992) created a GH-responsive cell line by stably transforming a myeloid leukemia cell line, FDC-P1, with a chimeric receptor comprising the extracellular domain of the rabbit GH receptor fused to the mouse G-CSF receptor. This cell line proliferates in response to GH with a half maximal effective concentration ($EC_{50}$) of 20 picomolar. A similar cell line can be constructed using the published sequences of these receptors and standard molecular biology techniques (Fuh et al., 1992). Alternatively, the extracellular domain of the human GH receptor can be fused to the mouse G-CSF receptor using the published sequences of these receptors and standard molecular biology techniques. Transformed cells expressing the chimeric receptor can be identified by flow cytometry using labeled GH, by the ability of transformed cells to bind radiolabeled GH, or by the ability of transformed cells to proliferate in response to added GH. Purified GH and GH muteins can be tested in cell proliferation assays using cells expressing the chimeric receptor to measure specific activities of the proteins. Cells can be plated in 96-well dishes with various concentrations of GH or GH muteins. After 18 h, cells are treated for 4 hours with ³H-thymidine and harvested for determination of incorporated radioactivity. The $EC_{50}$ can be determined for each mutein. Assays should be performed at least three times for each mutein using triplicate wells for each data point. GH muteins displaying similar optimal levels of stimulation and $EC_{50}$ values comparable to or greater than wild type GH are preferable.

GH muteins that retain in vitro activity can be PEGylated using a cysteine-reactive 8 kDa PEG-maleimide (or PEG-vinylsulfone) commercially available from Shearwater, Inc. Generally, methods for PEGylating the proteins with these reagents will be similar to those described in world patent applications WO 9412219 and WO 9422466 and PCT application US95/06540, with minor modifications. The recombinant proteins must be partially reduced with dithiothreitol (DTT) in order to achieve optimal PEGylation of the free cysteine. Although the free cysteine is not involved in a disulfide bond, it is relatively unreactive to cysteine-reactive PEGs unless this partial reduction step is performed. The amount of DTT required to partially reduce each mutein can be determined empirically, using a range of DTT concentrations. Typically, a 5-10 fold molar excess of DTT for 30 min at room temperature is sufficient. Partial reduction can be detected by a slight shift in the elution profile of the protein from a reversed-phase column. Care must be taken not to over-reduce the protein and expose additional cysteine residues. Over-reduction can be detected by reversed phase-HPLC (the protein will have a retention time similar to the fully reduced and denatured protein) and by the appearance of GH molecules containing two PEGs (detectable by a molecular weight change on SDS-PAGE). Wild type GH can serve as a control since it should not PEGylate under similar conditions. Excess DTT can be removed by size exclusion chromatography using spin columns. The partially reduced protein can be reacted with various concentrations of PEG-maleimide (PEG: protein molar ratios of 1:1, 5:1,10:1 and 50:1) to determine the optimum ratio of the two reagents. PEGylation of the protein can be monitored by a molecular weight shift using sodium dodecyl sulfate polyacrylamide gel electrophoresis (SDS-PAGE). The lowest amount of PEG that gives significant quantities of mono-pegylated product without giving di-pegylated product will be considered optimum (80% conversion to mono-pegylated product is considered good). Generally, mono-PEGylated protein can be purified from non-PEGylated protein and unreacted PEG by size-exclusion or ion exchange chromatography. The purified PEGylated protein can be tested in the cell proliferation assay described above to determine its specific activity.

The above experiments will allow identification of amino acids in the B-C loop, C-D loop or N-terminal end of the A-B loop in GH that can be changed to cysteine residues, PEGylated and retain in vitro biological activity. These muteins can be tested in animal disease models well known in the art.

Experiments can be performed to confirm that the PEG molecule is attached to the protein at the proper site. This can be accomplished by proteolytic digestion of the protein, purification of the PEG peptide (which will have a large molecular weight) by size exclusion, ion exchange or reversed phase chromatography, followed by amino acid sequencing or mass spectroscopy. The PEG-coupled amino acid will appear as a blank in the amino acid sequencing run.

The pharmacokinetic properties of the PEG-GH proteins can be determined as follows, or as described in world patent application WO9422466. Pairs of rats or mice can receive an intravenous bolus injection of the test proteins. Circulating levels of the proteins are measured over the course of 24 h by removing a small sample of blood from the animals at desired time points. Circulating levels of the test proteins can be quantitated using ELISA assays. Additional experiments can be performed using the subcutaneous route to administer the proteins. Similar experiments should be performed with the non-PEGylated protein to serve as a control. These experiments will reveal whether attachment of a PEG reagent to the protein alters its pharmacokinetic properties. Covalent modification of the protein with PEG should increase the protein's circulating half-life relative to the unPEGylated protein. Larger PEG molecules and/or attachment of multiple PEG molecules should lengthen the circulating half-life longer than smaller PEG molecules.

PEG-GH proteins can be tested in rodent models of growth hormone deficiency (Cox et al., 1994) and cachexia (Tomas et al., 1992; Read et al., 1992) to determine optimum dosing schedules and demonstrate efficacy. These studies can explore different size PEG molecules, e.g., 8 and 20 kDa, and dosing schedules to determine the optimum PEG size and dosing schedule. It is expected that the larger PEG molecule will increase the circulating half-life greater than the smaller PEG molecule and will require less frequent dosing. However, large proteins potentially may have reduced volumes of distribution in vivo; thus, it is possible a 20 kDa PEG attached to GH will limit bioavailability, reducing its efficacy. Rodent models will allow determination of whether this is the case. Once the optimum dosing schedules and PEG sizes are determined, the efficacy of PEG-GH to GH can be compared in the animal models. While all PEG-GH proteins having GH activity are included in the invention, the preferred PEG-GH proteins are those that enhance growth equal or superior to GH, but which can be given less frequently. PEG-GH should be more efficacious than GH when both are administered using the less frequent dosing schedules.

One GH deficiency model that can be used is a hypophysectomized rat. GH stimulates body weight gain and bone and cartilage growth in this model (Cox et al., 1994). Hypophysectomized rats can be purchased from Charles River. Rats can be injected with GH, PEG-GH or placebo and weight gain measured daily over a 10-14 day period. At time of sacrifice, tibial epiphysis width can be determined as a measure of bone growth. Experimental methods for performing these studies are described in Cox et al. (1994).

The efficacy of PEG-GH in rodent cachexia models can be tested in a similar manner. Daily administration of dexamethasone, via osmotic pumps or subcutaneous injection, can be used to induce weight loss (Tomas et al., 1992; Read et al., 1992; PCT patent application US95/06540).

EXAMPLE 2

Cysteine-Added Variants of Erythropoietin

This example relates to cysteine-added variants of erythropoietin (EPO). EPO is the hormone primarily responsible for stimulating erythropoiesis or red blood cell formation. EPO acts on immature red blood cell precursors to stimulate their further proliferation and differentiation into mature red blood cells. A commercial pharmaceutical version is available from Amgen, Inc. Human EPO is a 35-39 kDa glycoprotein secreted by the adult kidney. The mature human protein contains 166 amino acids and is heavily glycosylated. The sequence of human EPO (SEQ ID NO: 2) is shown in Lin et al 1985 and Jacobs et al. 1985, which are incorporated herein by reference. The primary sequence of EPO is highly conserved among species (greater than 80% identity; Wen et al., 1994). Sugar groups account for greater than 40% of the protein's mass. Human EPO contains three N-linked glycosylation sites and one O-linked glycosylation site. The N-linked glycosylation sites are conserved in different species whereas the O-linked glycosylation site is not. The extensive glycosylation of EPO has prevented the protein's crystallization, so the X-ray structure of the protein is not known. Human EPO contains four cysteine residues. The disulfide assignments are Cys7 to Cys161 and Cys29 to Cys33. Cys33 is not conserved in mouse EPO, suggesting that the Cys29-Cys33 disulfide bond is not critical to mouse EPO's structure or function. This conclusion also seems to hold for human EPO (Boissel et al., 1993).

The amino acid sequence of EPO is consistent with the protein being a member of the GH supergene family and mutational studies support this view of EPO's structure (Boissel et al., 1993; Wen et al., 1994). A model of the three dimensional structure of EPO, modeled after the GH structure has been proposed (Boissel et al., 1993; Wen et al., 1994). Helix A encompasses amino acids 9-22, Helix B encompasses amino acids 59-76, Helix C encompasses amino acids 90-107 and Helix D encompasses amino acids 132-152. Amino acids in EPO important for receptor binding have been identified through mutagenesis experiments and reside primarily in the N-terminal half of presumptive helix A and the C-terminal half of presumptive helix D (Boissel et al., 1993; Wen et al., 1994; Matthews et al., 1996). Only a single cell surface receptor for EPO has been identified (D'Andrea et al., 1989). It is believed that EPO dimerizes its receptor in much the same way that GH dimerizes its receptor (Matthew's et al., 1996).

Human EPO contains three sites for N-linked glycosylation (asparagine-24, -38 and -83) and one site for O-linked glycosylation (serine-126). The N-linked glycosylation sites are located in the A-B and B-C loops and the O-glycosylation site is located in the C-D loop. The N-linked glycosylation sites are conserved among species whereas the O-linked glycosylation site is absent in rodent EPO (Wen et al., 1993). A non-O-linked glycosylated human variant containing methionine at position 126 has been described (U.S. Pat. No. 4,703,008). The N-linked sugar groups are heavily branched and contain terminal sialic acid residues (Sasaki et al., 1987; Takeuchi et al., 1988). N-38 and N-83 contain the most highly branched oligosaccharides (Sasaki et al., 1988).

The terminal sialic residues on EPO are critical for the protein's in vivo function because removal of these residues by digestion eliminates in vivo activity (Fukada et al., 1989; Spivak and Hogans, 1989). Loss of activity correlates with faster clearance of the asialated protein from the body. The circulating half-life of the asialated protein in rats is less than ten minutes, in contrast to that of the sialated protein, which is approximately 2 hr (Fukada et al., 1989; Spivak and Hogans, 1989). Thus, in vivo activity of EPO directly correlates with its circulating half-life.

The role of N-linked sugars in EPO's biological activities has been better defined by mutating, individually and in combination, the three asparagine residues comprising the N-linked glycosylation sites. EPO muteins in which only a single N-linked glycosylation site was mutated, i.e., N24Q, N38Q and N83Q, were secreted from mammalian cells as efficiently as wild type EPO, indicating that N-linked glycosylation at all three sites is not required for protein secretion (N24Q indicates that the asparagine at position 24 is mutated to glutamine). In contrast, EPO muteins in which two or more N-linked glycosylation sites were mutated were secreted less efficiently than wild type EPO from mammalian cells (Yamaguchi et al., 1991; Delorme et al., 1992). Mutagenesis studies found that each of the single N-linked glycosylation site muteins had in vitro biological activities equal to or greater than wild type EPO. Thus, it was concluded that none of the N-linked glycosylation sites is essential for secretion or in vitro biological activity of EPO. In fact, removal of one of the glycosylation sites seemed to improve biological activity (Yamaguchi et al., 1991).

The in vivo biological activity of N-linked glycosylation muteins was studied by two groups. Yamaguchi et al. (1991) concluded that the N24Q and N83Q muteins had in vivo activities greater than wild type EPO, which correlated with their increased in vitro activities. These authors found that the N38Q mutein had decreased in vivo activity, about 60% of wild type EPO. N38 is the most heavily branched of the three N-linked glycosylation sites (Sasaki et al., 1988). Delorme et al. (1992) reported that mutating any of the N-linked glycosylation sites reduced in vivo biological activity by about 50%. Muteins in which two or more glycosylation sites were mutated had decreased in vivo activities in both studies.

The above studies indicate that some N-linked glycosylation is required for in vitro and in vivo activity of EPO. Individually, however, none of the three glycosylation sites is absolutely essential for activity. The N-linked sugars increase the apparent molecular weight of EPO and prolong its circulating half-life, which correlates with bioactivity. Natural EPO and EPO manufactured in mammalian cells have complex N-linked sugars containing galactose and terminal sialic acid residues. The galactose residues are recognized by specific receptors on hepatocytes and promote rapid clearance of EPO from the body unless the galactose residues are masked by the terminal sialic acid residues.

Mutagenesis studies concluded that O-linked glycosylation is not required for in vitro or in vivo function of EPO (Delorme et al., 1992). This is in keeping with the observation that rodent EPO is not O-glycosylated and with the existence of a naturally occurring human EPO variant in which serine-126 is replaced by methionine, with a corresponding lack of O-linked glycosylation. Mutagenesis of serine-126 revealed that certain amino acid changes at this site (to valine, histidine or glutamic acid) yielded EPO muteins with biological activities similar to wild type EPO, whereas other amino acid changes (to alanine or glycine) resulted in EPO molecules with severely reduced activities (Delorme et al., 1992). The effect of changing serine-126 to cysteine was not studied. The in vivo bioactivity of S126V EPO was found to be similar to wild type EPO (Delorme et al., 1992).

The requirement for complex, N-linked carbohydrates containing terminal sialic acid residues for in vivo activity of EPO has limited commercial manufacture of the protein to mammalian cells. The important functions of the sialated N-linked sugars are to prevent protein aggregation, increase protein stability and prolong the circulating half-life of the protein. The terminal sialic acid residues prolong EPO's circulating half-life by masking the underlying galactose residues, which are recognized by specific receptors on hepatocytes and promote clearance of the asialated protein. EPO can be produced in insect cells and is N-glycosylated and fully active in vitro; its activity in vivo has not been reported (Wojchowski et al., 1987).

This example provides for the design of cysteine-added EPO variants and their use in preparing conjugates using cysteine-reactive PEGs and other cysteine-reactive moieties. Certain amino acids in EPO are non-essential for biological activity and can be mutated to cysteine residues without altering the normal disulfide binding pattern and overall conformation of the molecule. These amino acids are located in the A-B loop (amino acids 23-58 of the mature protein sequence), the B-C loop (amino acids 77-89 of the mature protein sequence), the C-D loop (amino acids 108-131 of the mature protein sequence), proximal to helix A (amino acids 1-8) and distal to helix D (amino acids 153-166 of the mature protein sequence). Also contemplated as preferred sites for adding cysteine residues are at the N-terminus or C-terminus of the protein sequence. Preferred sites for cysteine substitutions are the O-linked glycosylation site (serine-126) and the amino acids comprising the three N-linked glycosylation sites (N24, I25, T26, N38, I39, T40, N83, S84, S85). Glycosylation sites are attractive sites for introducing cysteine substitutions and attaching PEG molecules to EPO because (1) these sites are surface exposed; (2) the natural protein can tolerate bulky sugar groups at these positions; (3) the glycosylation sites are located in the putative loop regions and away from the receptor binding site (Wen et al., 1994); and (4) mutagenesis studies indicate these sites (at least individually) are not essential for in vitro or in vivo activity (Yamaguchi et al., 1991; Delorme et al., 1992). As discussed above, the local conformation of the region encompassing the O-glycosylation site region seems to be important for biological activity. Whether a cysteine substitution at position 126 affects biological activity has not been studied. The cysteine-29 to cysteine-33 disulfide bond is not necessary for biological activity of EPO because changing both residues to tyrosine simultaneously yielded a biologically active EPO protein (Boissel et al., 1993; Wen et al., 1994). A "free" cysteine can be created by changing either cysteine-29 or cysteine-33 to another amino acid. Preferred amino acid changes would be to serine or alanine. The remaining "free" cysteine (cysteine-29 or cysteine-33) would be a preferred site for covalently modifying the protein with cysteine-reactive moieties.

Bill et al. (1995) individually substituted cysteine for N24, N38 and N83 and reported that the muteins had greatly reduced in vitro biological activities (less than 20% of wild type activity). Bill et al.(1995) expressed the EPO variants as fusion proteins (fused to glutathionine-S-transferase) in bacteria. One aspect of the present invention is to provide expression systems in which the N24C, N38C and N83C EPO variants will have in vitro biological activities more similar to wild type EPO.

U.S. Pat. No. 4,703,008 contemplates naturally occurring variants of EPO as well as amino acid substitutions that are present in EPO proteins of mammals. Ovine EPO contains a cysteine residue at position 88 of the polypeptide chain. The inventor is unaware of any other naturally occurring human or animal cysteine variants of EPO in which the cysteine residue occurs in the polypeptide regions disclosed herein as being useful for generating cysteine-added EPO variants. U.S. Pat. No. 4,703,008 specifically teaches away from cysteine-added EPO variants by suggesting that expression of EPO might be improved by deleting cysteine residues or substituting naturally occurring cysteine residues with serine or histidine residues.

The mature protein form of EPO can contain 165 or 166 amino acids because of post-translational removal of the C-terminal arginine. Asp-165 is the C-terminus of the 165 amino acid form and Agr-166 is the C-terminal amino acid of the 166 amino acid form. The cysteine substitution and insertion mutations described herein can comprise either the 165 or 166 amino acid forms of mature EPO.

A cDNA encoding EPO can be cloned using the polymerase chain reaction (PCR) technique from the human HepG2 or Hep3B cell lines, which are known to express EPO when treated with hypoxia or cobalt chloride (Wen et al., 1993) and are available from the American Type Culture Collection (ATCC). Cysteine mutations can be introduced into the cDNA by standard phage, plasmid or PCR mutagenesis procedures as described for GH. As described above, the preferred sites for introduction of cysteine substitution mutations are in the A-B loop, the B-C loop, the C-D loop and the region proximal to helix A and distal to helix D. The most preferred sites in these regions are the N- and O-linked glycosylation sites: S126C; N24C; I25C, T26C; N38C; I39C, T40C; N83C, S 84C and S85C. Other preferred sites for cysteine substitution mutagenesis are in the A-B loop, the B-C loop and the C-D loop, amino acids surrounding the glycosylation sites and the region of the protein proximal to helix A and distal to helix D (Boissel et al., 1993; Wen et al., 1994). Other preferred sites for cysteine substitutions in these regions are: A1, P2, P3, R4, D8, S9, T27, G28, A30, E31, H32, S34, N36, D43, T44, K45, N47, A50, K52, E55, G57, Q58, G77, Q78, A79, Q86, W88, E89, T107, R110, A111, G113, A114, Q115, K116, E117, A118, S120, P121, P122, D123, A124, A125, A127, A128, T132, K154, T157, G158, E159, A160, T163, G164, D165 and R166. Cysteine residues also can be introduced proximal to the first amino acid of the mature protein, i.e., proximal to A1, or distal to the final amino acid in the mature protein, i.e., distal to D165 or R166. Other variants in which cys-29 or cys-33 have been replaced with other amino acids, preferably serine or alanine, also are provided.

Wild type EPO and EPO muteins can be expressed using insect cells to determine whether the cysteine-added muteins are biologically active. DNAs encoding EPO/EPO muteins can be cloned into the Baculovirus expression vector pVL1392 (available from Invitrogen, Inc. and Sigma Corporation (St. Louis, Mo.) and used to infect insect cells. Recombinant Baculoviruses producing EPO can be identified by Western blots of infected insect cell conditioned media using polyclonal anti-human EPO antiserum (available from R&D Systems). The secreted EPO mutein proteins can be purified by conventional chromatographic procedures well known to those of skill in the art. Protein concentrations can be determined using commercially available protein assay kits or ELISA assay kits (available from R&D Systems and Bio-Rad Laboratories).

Purified EPO and EPO muteins can be tested in cell proliferation assays using EPO-responsive cell lines such as UT7-epo (Wen et al., 1994) or TF1 (available from the ATCC) to measure specific activities of the proteins. Cells can be plated in 96-well microtiter plates with various concentrations of EPO. Assays should be performed in triplicate. After 1-3 days in culture, cell proliferation can be measured by $^3$H-thymidine incorporation, as described above for GH. The concentration of protein giving half-maximal stimulation ($EC_{50}$) can be determined for each mutein. Assays should be performed at least three times for each mutein, with triplicate wells for each data point. $EC_{50}$ values can be used to compare the relative potencies of the muteins. Alternatively, cell proliferation in response to added EPO muteins can be analyzed using an MTT dye-exclusion assay (Komatsu et al. 1991). Proteins displaying similar optimal levels of stimulation and $EC_{50}$ values comparable to or greater than wild type EPO are preferable.

The above studies confirm identification of amino acid residues in EPO that can be changed to cysteine residues and retain biological activity. Muteins that retain activity can be PEGylated using a cysteine-reactive 8 kDa PEG-maleimide as described above for GH muteins. Wild type EPO should be used as a control since it should not react with the cysteine-reactive PEG under identical partial reduction conditions. The lowest amount of PEG that gives significant quantities of mono-PEGylated product without giving di-PEGylated product should be considered optimum. Mono-PEGylated protein can be purified from non-PEGylated protein and unreacted PEG by size-exclusion or ion exchange chromatography. The purified PEGylated proteins should be tested in the cell proliferation assay described above to determine their bioactivities.

One or more of the PEGylated EPO muteins that retain in vitro bioactivity, are candidates for testing in animal disease models. PEGylation of the protein at the proper amino acid can be determined as described for GH.

In vivo testing of PEGylated EPO muteins expressed using insect cells may require that they be re-engineered for expression in mammalian cells to ensure proper glycosylation. PEG-EPO candidates produced using insect cells can be tested in the animal models described below to determine if they are active in vivo and whether they are as active as PEG-EPO produced using mammalian cell expression systems. For expression in mammalian cells, the EPO muteins can be subcloned into commercially available eukaryotic expression vectors and used to stably transform Chinese Hamster Ovary (CHO) cells (available from the ATCC). Sublines can be screened for EPO expression using ELISA assays. Sufficient quantities of the insect cell- and mammalian cell-produced EPO muteins can be prepared to compare their biological activities in animal anemia models.

In vivo bioactivities of the EPO muteins can be tested using the artificial polycythemia or starved rodent models (Cotes and Bangham., 1961; Goldwasser and Gross., 1975). In the starved rodent model, rats are deprived of food on day one and treated with test samples on days two and three. On day four, rats receive an injection of radioactive iron-59. Approximately 18 h later, rats are anesthetized and blood samples drawn. The percent conversion of labeled iron into red blood cells is then determined. In the artificial polycythemia model, mice are maintained in a closed tank and exposed for several days to hypobaric air. The animals are then brought to normal air pressure. Red blood cell formation is suppressed for several days. On day four or six after return to normal air pressure, mice are injected with erythropoietin or saline. Mice receive one injection per day for one to two days. One day later the animals receive an intravenous injection of labeled iron-59. The mice are euthanized 20 h later and the amount of labeled iron incorporated into red blood cells determined. EPO stimulates red blood cell formation in both models as measured by a dose-dependent increase in labeled iron incorporated into red blood cells. In both models different dosing regimens and different times of injections can be studied to determine if PEG-EPO is biologically active and/or more potent and produces longer acting effects than natural EPO.

EXAMPLE 3

Alpha Interferon

Alpha interferon is produced by leukocytes and has antiviral, anti-tumor and immunomodulatory effects. There are at least 20 distinct alpha interferon genes that encode proteins that share 70% or greater amino acid identity. Amino acid sequences of the known alpha interferon species are given in Blatt et al. (1996). A "consensus" interferon that incorporates the most common amino acids into a single polypeptide chain has been described (Blatt et al., 1996). A hybrid alpha interferon protein may be produced by splicing different parts of alpha interferon proteins into a single protein (Horisberger and Di Marco, 1995). Some alpha interferons contain N-linked glycosylation sites in the region proximal to helix A and near the B-C loop (Blatt et al. 1966). The alpha 2 interferon protein (SEQ ID NO: 3) contains four cysteine residues that form two disulfide bonds. The cys1-cys98 disulfide bond (cys1-cys99 in some alpha interferon species such as alpha 1; SEQ ID NO: 4) is not essential for activity. The alpha 2-interferon protein does not contain any N-linked glycosylation sites. There are two subtypes of the alpha-2 interferon protein; one subtype has arginine at position 23 whereas the other subtype has lysine at position 23. The crystal structure of alpha interferon has been determined (Radhakrishnan et al., 1996). Alpha interferon has five major alpha helices referred to as helices A-E. Helix A encompasses amino acids 9-21, helix B encompasses amino acids 52-68, helix C encompasses amino acids 78-100, helix D encompasses amino acids 112-132 and helix E encompasses amino acids 137-160.

This example provides cysteine added variants in the region proximal to the A helix (amino acids 1-8), distal to the E helix (amino acids 161-165), in the A-B loop (amino acids 22-51), in the B-C loop (amino acids 69-77), in the C-D loop (amino acids 101-111) and in the D-E loop (amino acids 133-136). This Example also provides cysteine-added variants at the first three or last three amino acids in helices A, B, C, D and E. Preferred sites for the introduction of cysteine residues in these regions of the alpha interferon-2 species are: D2, L3, P4, Q5, T6, S8, Q20, R22, K/R23, S25, F27, S28, K31, D32, R33, D35, G37, F38, Q40, E41, E42, F43, G44, N45, Q46, F47, Q48, K49, A50, N65, S68, T69, K70, D71, S72, S73, A74, A75, D77, E78, T79, Y89, Q90, Q91, N93, D94, E96, A97, Q101, G102, G104, T106, E107, T108, P109, K112, E113, D114, S115, K131, E132, K133, K134, Y135, S136, A139, S152, S154, T155, N156, L157, Q158, E159, S160, L161, R162, S163, K164, E165. Variants in which cysteine residues are introduced proximal to the first amino acid of the mature protein, i.e., proximal to C1, or distal to the final amino acid in the mature protein, i.e., distal to E165 are provided. Other variants in which cys-1 or cys-98 (cys-99 in some alpha interferon species) have been replaced with other amino acids, preferably serine or alanine, also are provided. Other variants in which Cys-1 has been deleted (des Cys-1) also are provided. The cysteine variants may be in the context of any naturally occurring or non-natural alpha interferon sequence, e.g., consensus interferon or interferon protein hybrids. Some naturally occurring alpha interferon species (e.g., alpha interferon-1) contain a naturally occurring "free" cysteine. In such interferon species the naturally occurring free cysteine can be changed to another amino acid, preferably serine or alanine.

This example also provides cysteine variants of other alpha interferon species, including consensus interferon, at equivalent sites in these proteins. The alignment of the alpha interferon-2 species with other known alpha interferon species and consensus interferon is given in Blatt et al. (1996). The crystal structure of alpha interferon-2 has been determined by Rhadhakrishnan et al. (1996). Lydon et al (1985) found that deletion of the first four amino acids from the N-terminus of alpha interferon did not affect biological activity. Valenzuela et al (1985) found that substitution of Phe-47 in alpha interferon-2 with Cys, Tyr or Ser did not alter biological activity of the protein. Cys-1 and Cys-98 have been changed individually to glycine and serine, respectively, without altering biological activity of the protein (DeChiara et al, 1986).

DNA sequences encoding alpha interferon-2 can be amplified from human genomic DNA, since alpha interferon genes do not contain introns (Pestka et al., 1987). The DNA sequence of alpha interferon-2 is given in Goeddel et al. (1980). Alternatively, a cDNA for alpha interferon-2 can be isolated from human lymphoblastoid cell lines that are known to express alpha interferon spontaneously or after exposure to viruses (Goeddell et al., 1980; Pickering et al., 1980). Many of these cell lines are available from the American Type Culture Collection 10801 University Blvd., Manassas, VA 20110-2209). Specific mutations can be introduced into the alpha interferon sequence using plasmid-based site-directed mutagenesis kits (e.g., Quick-Change Mutagenesis Kit, Stratagene, Inc.), phage mutagenesis strategies or employing PCR mutagenesis as described for GH.

Alpha interferon has been successfully produced in *E. coli* as an intracellular protein (Tarnowski et al., 1986; Thatcher and Panayotatos, 1986). Similar procedures can be used to express alpha interferon muteins. Plasmids encoding alpha interferon or alpha interferon muteins can be cloned into an *E. coli* expression vector such as pET15b (Novagene, Inc.) that uses the strong T7 promoter or pCYB1 (New England BioLabs, Beverly, Mass.) that uses the TAC promoter. Expression of the protein can be induced by adding IPTG to the growth media.

Recombinant alpha interferon expressed in *E. coli* is sometimes soluble and sometimes insoluble (Tarnowski et al., 1986; Thatcher and Panayotatos, 1986). Insolubility appears to be related to the degree of overexpression of the protein. Insoluble alpha interferon proteins can be recovered as inclusion bodies and renatured to a fully active conformation following standard oxidative refolding protocols (Thatcher and Panayotatos, 1986; Cox et al., 1994). The alpha interferon proteins can be purified further using other chromatographic methods such as ion-exchange, hydrophobic interaction, size-exclusion and reversed phase resins (Thatcher and Panayotaos, 1986). Protein concentrations can be determined using commercially available protein assay kits (Bio-Rad Laboratories).

If *E. coli* expression of alpha interferon muteins is not successful, one can express the proteins in insect cells as secreted proteins as described for GH. The proteins can be modified to contain the natural alpha interferon signal sequence (Goeddell et al., 1980) or the honeybee mellitin signal sequence (Invitrogen, Inc.) to promote secretion of the proteins. Alpha interferon and alpha interferon muteins can be purified from conditioned media using conventional chromatography procedures. Antibodies to alpha interferon can be used in conjunction with Western blots to localize fractions containing the alpha interferon proteins during chromatography. Alternatively, fractions containing alpha interferon proteins can be identified using ELISAs.

Bioactivities of alpha interferon and alpha interferon muteins can be measured using an in vitro viral plaque reduction assay (Ozes et al., 1992; Lewis, 1995). Human HeLa cells can be plated in 96-well plates and grown to near confluency at 37° C. The cells are then washed and treated for 24 hour with different concentrations of each alpha interferon preparation. Controls should include no alpha interferon and wild type alpha interferon (commercially available from Endogen, Inc., Woburn, Mass.). A virus such as Vesicular stomatitis virus (VSV) or encephalomyocarditis virus (EMCV) is added to the plates and the plates incubated for a further 24-48 hours at 37° C. Additional controls should include samples without virus. When 90% or more of the cells have been killed in the virus-treated, no alpha interferon control wells (determined by visual inspection of the wells), the cell monolayer are stained with crystal violet and absorbance of the wells read using a microplate reader. Alternatively, the cell monolayers can be stained with the dye MTT (Lewis, 1995). Samples should be analyzed in duplicate or triplicate. $EC_{50}$ values (the amount of protein required to inhibit the cytopathic effect of the virus by 50%) can be used to compare the relative potencies of the proteins. Wild type alpha interferon-2 protects cells from the cytopathic effects of VSV and EMCV and has a specific activity of approximately $2 \times 10^8$ units/mg in this assay (Ozes et al., 1992). Alpha interferon muteins displaying $EC_{50}$ values comparable to wild type Alpha Interferon are preferable.

Alpha interferon muteins that retain activity can be PEGylated using procedures similar to those described for GH. Wild type alpha interferon-2 can serve as a control since it should not PEGylate under similar conditions. The lowest amount of PEG that gives significant quantities of mono-pegylated product without giving di-pegylated product should be considered optimum. Mono-PEGylated protein can be purified from non-PEGylated protein and unreacted PEG by size-exclusion or ion exchange chromatography. The purified PEGylated proteins can be tested in the viral plaque reduction bioassay described above to determine their bioactivities. PEGylated alpha interferon proteins with bioactivities comparable to wild type alpha interferon are preferable. Mapping the PEG attachment site and determination of pharmacokinetic data for the PEGylated protein can be performed as described for GH.

In vivo bioactivities of the PEG-alpha interferon muteins can be tested using tumor xenograft models in nude mice and viral infection models (Balkwill, 1986; Fish et al., 1986). Since PEG-alpha interferon bioactivity may be species-specific, one should confirm activity of the PEGylated protein using appropriate animal cell lines in in vitro virus plaque reduction assays, similar to those described above. Next, one should explore the effects of different dosing regimens and different times of injections to determine if PEG-alpha interferon is more potent and produces longer lasting effects than non-PEGylated alpha interferon.

The novel alpha interferon-derived molecules of this example can be formulated and tested for activity essentially as set forth in Examples 1 and 2, substituting, however, the appropriate assays and other considerations known in the art related to the specific proteins of this example.

EXAMPLE 4

Beta Interferon

Beta interferon is produced by fibroblasts and exhibits antiviral, antitumor and immunomodulatory effects. The single-copy beta interferon gene encodes a preprotein that is cleaved to yield a mature protein of 166 amino acids (Taniguchi et al. 1980; SEQ ID NO: 5). The protein contains three cysteines, one of which, cysteine-17, is "free", i.e., it does not participate in a disulfide bond. The protein contains one N-linked glycosylation site. The crystal structure of the protein has been determined (Karpusas et al. 1997). Beta interferon has five major alpha helices referred to as helices A-E. Helix A encompasses amino acids 2-22, helix B encompasses amino acids 51-71, helix C encompasses amino acids 80-107, helix D encompasses amino acids 118-136 and helix E encompasses amino acids 139-162.

This example provides cysteine-added variants at any of the three amino acids that comprise the N-linked glycosylation sites, i.e., N80C, E81C or T82C. This example also provides cysteine-added variants in the region proximal to the A helix (amino acid 1), distal to the E helix (amino acids 163-166), in the A-B loop (amino acids 23-50), in the B-C loop (amino acids 72-79), in the C-D loop (amino acids 108-117) and in the D-E loop (amino acids 137-138). This Example also provides cysteine-added variants at the first three or last three amino acids in helices A, B, C, D and E. Preferred sites for introduction of cysteine residues in these regions are: M1, S2, Y3, N4, L5, Q23, N25, G26, R27, E29, Y30, K33, D34, R35, N37, D39, E42, E43, K45, Q46, L47, Q48, Q49, Q51, K52, E53, A68, F70, R71, Q72, D73, S74, S75, S76, T77, G78, E107, K108, E109, D110, F111, T112, R113, G114, K115, L116, A135, K136, E137, K138, S139, I157, N158, R159, L160, T161, G162, Y163, L164, R165 and N166. Variants in which cysteine residues are introduced proximal to the first amino acid of the mature protein, i.e., proximal to M1, or distal to the final amino acid in the mature protein, i.e., distal to N166 also are provided.

These variants are produced in the context of the natural protein sequence or a variant protein in which the naturally occurring "free" cysteine residue (cysteine-17) has been changed to another amino acid, preferably serine or alanine.

The novel beta interferon-derived molecules of this example can be formulated and tested for activity essentially as set forth in Examples 1 and 2, substituting, however, the appropriate assays and other considerations known in the art related to the specific proteins of this example.

EXAMPLE 5

Granulocyte Colony-Stimulating Factor (G-CSF)

G-CSF is a pleuripotent cytokine that stimulates the proliferation, differentiation and function of granulocytes. The protein is produced by activated monocytes and macrophages. The amino acid sequence of G-CSF (SEQ ID NO: 6) is given in Souza et al. (1986), Nagata et al. (1986a, b) and U.S. Pat. No. 4,810,643 all incorporated herein by reference. The human protein is synthesized as a preprotein of 204 or 207 amino acids that is cleaved to yield mature proteins of 174 or 177 amino acids. The larger form has lower specific activity than the smaller form. The protein contains five cysteines, four of which are involved in disulfide bonds. Cysteine-17 is not involved in a disulfide bond. Substitution of cysteine-17 with serine yields a mutant G-CSF protein that is fully active (U.S. Pat. No. 4,810,643). The protein is O-glycosylated at threonine-133 of the mature protein. G-CSF contains four major alpha helices referred to as helices A-D. Helix A encompasses amino acids 11-39, helix B encompasses amino acids 71-91, helix C encompasses amino acids 100-123 and helix D encompasses amino acids 143-172.

This example provides a cysteine-added variant at threonine-133. This example provides other cysteine-added variants in the region proximal to helix A (amino acids 1-10), distal to helix D (amino acids 173-174), in the A-B loop (amino acids 40-70), B-C loop (amino acids 92-99) and C-D loop (amino acids 124-142). This Example also provides cysteine-added variants at the first three or last three amino acids in helices A, B, C and D. Preferred sites for introduction of cysteine substitutions in these regions are: T1, P2, L3, G4, P5, A6, S7, S8, L9, P10, Q11, S12, T38, K40, S53, G55, W58, A59, P60, S62, S63, P65, S66, Q67, A68, Q70, A72, Q90, A91, E93, G94, S96, E98, G100, G125, M126, A127, A129, Q131, T133, Q134, G135, A136, A139, A141, S142, A143, Q145, Q173 and P174. Variants in which cysteine residues are introduced proximal to the first amino acid of the mature protein, i.e., proximal to T1, or distal to the final amino acid in the mature protein, i.e., distal to P174 are provided. These variants are provided in the context of the natural protein sequence or a variant protein in which the naturally occurring "free" cysteine residue (cysteine-17) has been changed to another amino acid, preferably serine or alanine.

A cDNA encoding human G-CSF can be purchased from R&D Systems (Minneapolis, Minn.) or amplified using PCR from mRNA isolated from human carcinoma cell lines such as 5637 and U87-MG known to express G-CSF constitutively (Park et al., 1989; Nagata, 1994). These cell lines are available from the American Type Culture collection (Rockville, Md.). Specific mutations can be introduced into the G-CSF sequence using plasmid-based site-directed mutagenesis kits (e.g., Quick-Change Mutagenesis Kit, Stratagene, Inc.), phage mutagenesis methods or employing PCR mutagenesis as described for GH.

G-CSF has been successfully produced in $E.\ coli$ as an intracellular protein (Souza et al., 1986). One can employ similar procedures to express G-CSF and G-CSF muteins. Plasmids encoding G-CSF or G-CSF muteins can be cloned into an $E.\ coli$ expression vector such as pET15b (available from Novagen, Inc., Madison, Wis.) that uses the strong T7 promoter or pCYB1 (available from New England BioLabs, Beverly, Mass.) that uses the strong TAC promoter. Expression of the protein can be induced by adding IPTG to the growth media. Recombinant G-CSF expressed in $E.\ coli$ is insoluble and can be recovered as inclusion bodies. The protein can be renatured to a fully active conformation following standard oxidative refolding protocols (Souza et al., 1986; Lu et al., 1992; Cox et al., 1994). Similar procedures can be used to refold cysteine muteins. The proteins can be purified further using other chromatographic methods such as ion exchange, hydrophobic interaction, size-exclusion and reversed phase resins (Souza et al., 1986; Kuga et al., 1989; Lu et al., 1992). Protein concentrations can be determined using commercially available protein assay kits (Bio-Rad Laboratories).

If $E.\ coli$ expression of G-CSF or G-CSF muteins is not successful, one can express G-CSF and G-CSF muteins in insect cells as secreted proteins as described for GH. The proteins can be modified to contain the natural G-CSF signal sequence (Souza et al., 1986; Nagata et al., 1986a; Nagata et al, 1986b) or the honeybee mellitin signal sequence (Invitrogen, Inc., Carlsbad, Calif.) to promote secretion of the proteins. G-CSF and G-CSF muteins can be purified from conditioned media using conventional chromatography procedures. Antibodies to G-CSF can be used in conjunction with Western blots to localize fractions containing the G-CSF proteins during chromatography. Alternatively, fractions containing G-CSF proteins can be identified using ELISAs.

G-CSF muteins also can be expressed in mammalian cells as described for erythropoietin in Example 2.

Bioactivities of G-CSF and the G-CSF muteins can be measured using an in vitro cell proliferation assay. The mouse NFS-60 cell line and the human AML-193 cell line can be used to measure G-CSF bioactivity (Tsuchiya et al., 1986; Lange et al., 1987; Shirafuji et al., 1989). Both cell lines proliferate in response to human G-CSF. The AML-193 cell line is preferable since it is of human origin, which eliminates the possibility of a false conclusion resulting from species differences. The NFS60 cell lines proliferates in response to G-CSF with a half-maximal effective concentration ($EC_{50}$) of 10-20 picomolar. Purified G-CSF and G-CSF muteins can be tested in cell proliferation assays using these cell lines to determine specific activities of the proteins, using published methods (Tsuchiya et al., 1986; Lange et al., 1987; Shirafuji et al., 1989). Cells can be plated in 96-well tissue culture dishes with different concentrations of G-CSF or G-CSF muteins. After 1-3 days at 37° C. in a humidified tissue culture incubator, proliferation can be measured by $^3$H-thymidine incorporation as described for GH. Assays should be performed at least three times for each mutein using triplicate wells for each data point. $EC_{50}$ values can be used to compare the relative potencies of the muteins. G-CSF muteins displaying similar optimal levels of stimulation and $EC_{50}$ values comparable to wild type G-CSF are preferable.

G-CSF muteins that retain activity can be PEGylated using procedures similar to those described for GH. Wild type G-CSF and ser-17 G-CSF can serve as controls since they should not PEGylate under similar conditions. The lowest amount of PEG that gives significant quantities of mono-PEGylated product without giving di-PEGylated product should be considered optimum. Mono-PEGylated protein can be purified from non-PEGylated protein and unreacted PEG by size-exclusion or ion exchange chromatography. The purified PEGylated proteins can be tested in the cell proliferation assay described above to determine their bioactivities.

The PEG site in the protein can be mapped using procedures similar to those described for GH. Pharmacokinetic data for the PEGylated proteins can be obtained using procedures similar to those described for GH.

Initial studies to demonstrate in vivo efficacy of PEG-G-CSF can be done in normal Sprague-Dawley rats, which can be purchased from Charles River. Groups of rats should receive single subcutaneous or intravenous injections of various doses of G-CSF, PEG-G-CSF or placebo. Animals should be sacrificed at daily intervals for up to a week for determination of neutrophil and total white blood cell counts in peripheral blood. Other blood cell types (platelets and red blood cells) can be measured to demonstrate cell specificity.

The efficacy of PEG-G-CSF can be tested in a rat neutropenia model. Neutropenia can be induced by treatment with cyclophosphamide, which is a commonly used chemotherapeutic agent that is myelosuppressive. G-CSF accelerates recovery of normal neutrophil levels in cyclophosphamide-treated animals (Kubota et al., 1990). Rats receive an injection of cyclophosphamide on day 0 to induce neutropenia. The animals are then be divided into different groups, which will receive subcutaneous injections of G-CSF, PEG-G-CSF or placebo. Neutrophil and total white blood cell counts in peripheral blood should be measured daily until they return to normal levels. Initially one should confirm that G-CSF accelerates recovery from neutropenia when injected daily. Next, one should explore the effects of different dosing regimens and different times of injections to determine if PEG-G-CSF is more potent and produces longer lasting effects than non-PEGylated G-CSF.

The novel GCSF-derived molecules of this example can be formulated and tested for activity essentially as set forth in Examples 1 and 2, substituting, however, the appropriate assays and other considerations known in the art related to the specific proteins of this example.

EXAMPLE 6

Thrombopoietin (TPO)

Thrombopoietin stimulates the development of megakaryocyte precursors of platelets. The amino acid sequence of TPO (SEQ ID NO: 7) is given in Bartley et al. (1994), Foster et al. (1994), de Sauvage et al. (1994), each incorporated herein by reference.

The protein is synthesized as a 353 amino acid precursor protein that is cleaved to yield a mature protein of 332 amino acids. The N-terminal 154 amino acids have homology with EPO and other members of the GH supergene family. The C-terminal 199 amino acids do not share homology with any other known proteins. The C-terminal region contains six N-linked glycosylation sites and multiple O-linked glycosylation sites (Hoffman et al., 1996). O-linked glycosylation sites also are found in the region proximal to the A helix, in the A-B loop, and at the C-terminus of Helix C (Hoffman et al., 1996). A truncated TPO protein containing only residues 1-195 of the mature protein is fully active in vitro (Bartley et al., 1994).

This example provides cysteine-added variants at any of the amino acids that comprise the N-linked glycosylation sites and the O-linked glycosylation sites. This example also provides cysteine-added variants in the region proximal to the A helix (amino acids 1-7), distal to the D helix (amino acids 148-332), in the A-B loop (amino acids 34-58), in the B-C loop (amino acids 78-86), and in the C-D loop (amino acids 111-122). This Example also provides cysteine-added variants at the first three or last three amino acids in helices A, B, C and D. Helix a encompasses amino acids 8-33, helix B encompasses amino acids 59-77, helix C encompasses amino acids 87-110 and helix D encompasses amino acids 123-147.

Preferred sites for introduction of cysteine residues are: S1, P2, A3, P4, P5, A6, T37, A43, D45, S47, G49, E50, K52, T53, Q54, E56, E57, T58, A76, A77, R78, G79, Q80, G82, T84, S87, S88, G109, T110, Q111, P113, P114, Q115, G116, R117, T118, T119, A120, H121, K122, G146, G147, S148, T149, A155, T158, T159, A160, S163, T165, S166, T170, N176, R177, T178, S179, G180, E183, T184, N185, F186, T187, A188, S189, A190, T192, T193, G194, S195, N213, Q214, T215, S216, S218, N234, G235, T236, S244, T247, S254, S255, T257, S258, T260, S262, S272, S274, T276, T280, T291, T294, S307, T310, T312, T314, S315, N319, T320, S321, T323, S325, Q326, N327, L328, S329, Q330, E331 and G332. Variants in which cysteine residues are introduced proximal to the first amino acid of the mature protein, i.e., proximal to S1, or distal to the final amino acid in the mature protein, i.e., distal to G332 are provided. The cysteine-added variants are provided in the context of the natural human protein or a variant protein that is truncated between amino acids 147 and the C-terminus of the natural protein, G332. Variants in which cysteine residues are added distal to the final amino acid of a TPO protein that is truncated between amino acids 147 and 332 also are provided.

The novel TPO-derived molecules of this example can be formulated and tested for activity essentially as set forth in Examples 1 and 2, substituting, however, the appropriate assays and other considerations known in the art related to the specific proteins of this example.

EXAMPLE 7

Granulocyte-Macrophage Colony Stimulating Factor (GM-CSF)

GM-CSF stimulates the proliferation and differentiation of various hematopoietic cells, including neutrophil, monocyte, eosinophil, erythroid, and megakaryocyte cell lineages. The amino acid sequence of human GM-CSF (SEQ ID NO: 8) is given in Cantrell et al. (1985) and Lee et al (1985) both incorporated herein by reference.

GM-CSF is produced as a 144 amino acid preprotein that is cleaved to yield a mature 127 amino acid protein. The mature protein has two sites for N-linked glycosylation. One site is located at the C-terminal end of Helix A; the second site is in the A-B loop. GM-CSF has four major alpha helices referred to as helices A-D. Helix A encompasses amino acids 13-27, helix B encompasses amino acids 55-65, helix C encompasses amino acids 74-86 and helix D encompasses amino acids 103-116.

This example provides cysteine-added variants at any of the amino acids that comprise the N-linked glycosylation sites, i.e., N27C, L28C, S29C, N37C, E38C and T39C. This example also provides cysteine-added variants in the region proximal to the A helix (amino acids 1-12), distal to the D helix (amino acids 117-127), in the A-B loop (amino acids 28-54), in the B-C loop (amino acids 66-73), and in the C-D loop (amino acids 87-102). This Example also provides cysteine-added variants at the first three or last three amino acids in helices A, B, C and D. Preferred sites for introduction of cysteine substitutions in these regions are: A1, P2, A3, R4, S5, P6, S7, P8, S9, T10, Q11, R30, D31, T32, A33, A34, E35, E41, S44, E45, D48, Q50, E51, T53, Q64, G65, R67, G68, S69, L70, T71, K72, K74, G75, T91, E93, T94, S95, A97, T98, T102, I117, D120, E123, V125, Q126 and E127. Variants in which cysteine residues are introduced proximal to the first amino acid of the mature protein, i.e., proximal to A1, or distal to the final amino acid in the mature protein, i.e., distal to E127 are provided.

The novel GM-CSF-derived molecules of this example can be formulated and tested for activity essentially as set forth in Examples 1 and 2, substituting, however, the appropriate assays and other considerations known in the art related to the specific proteins of this example.

EXAMPLE 8

IL-2

IL-2 is a T cell growth factor that is synthesized by activated T cells. The protein stimulates clonal expansion of activated T cells. Human IL-2 is synthesized as a 153 amino acid precursor that is cleaved to yield a 133 amino acid mature protein (Tadatsugu et al., 1983; Devos et al., 1983; SEQ ID NO: 9).

The amino acid sequence of IL-2 is set forth in (Tadatsugu et al. 1983; Devos et al. 1983). The mature protein contains three cysteine residues, two of which form a disulfide bond. Cysteine-125 of the mature protein is not involved in a disulfide bond. Replacement of cysteine-125 with serine yields an IL-2 mutein with full biological activity (Wang et al., 1984). The protein is O-glycosylated at threonine-3 of the mature protein chain. IL-2 has four major alpha helices referred to as helices A-D. Helix a encompasses amino acids 1-11, helix B encompasses amino acids 54-73, helix C encompasses amino acids 83-97 and helix d encompasses amino acids 115-133.

This example provides cysteine-added variants in the last four positions of the D helix, in the region distal to the D helix (amino acids 130-133), in the A-B loop (amino acids 28-53), in the B-C loop (amino acids 74-82), and in the C-D loop (amino acids 98-114). These variants are provided in the context of the natural protein sequence or a variant protein in which the naturally occurring "free" cysteine residue (cysteine-125) has been changed to another amino acid, preferably serine or alanine. Variants in which cysteine residues are introduced proximal to the first amino acid, i.e., A1, or distal to the final amino acid, i.e., T133, of the mature protein, also are provided.

The novel IL-2-derived molecules of this example can be formulated and tested for activity essentially as set forth in Examples 1 and 2, substituting, however, the appropriate assays and other considerations known in the art related to the specific proteins of this example.

EXAMPLE 9

IL-3

IL-3 is produced by activated T cells and stimulates the proliferation and differentiation of pleuripotent hematopoietic stem cells. The amino acid sequence of human IL-3 (SEQ ID NO: 10) is given in Yang et al. (1986); Dorssers et al. (1987) and Otsuka et al. (1988) all incorporated herein by reference. The protein contains two cysteine residues and two N-linked glycosylation sites. Two alleles have been described, resulting in isoforms having serine or proline at amino acid position 8 or the mature protein.

This example provides cysteine-added variants at any of the amino acids that comprise the N-linked glycosylation sites. This example also provides cysteine-added variants in the region proximal to the A helix, distal to the D helix, in the A-B loop, in the B-C loop, and in the C-D loop. Variants in which cysteine residues are introduced proximal to the first amino acid or distal to the final amino acid in the mature protein, also are provided.

The novel IL-3-derived molecules of this example can be formulated and tested for activity essentially as set forth in Examples 1 and 2, substituting, however, the appropriate assays and other considerations known in the art related to the specific proteins of this example.

EXAMPLE 10

IL-4

IL-4 is a pleiotropic cytokine that stimulates the proliferation and differentiation of monocytes and T and B cells. IL-4 has been implicated in the process that leads to B cells secreting IgE, which is believed to play a role in asthma and atopy. The bioactivity of IL-4 is species specific. IL-4 is synthesized as a 153 amino acid precursor protein that is cleaved to yield a mature protein of 129 amino acids. The amino acid sequence of human IL-4 (SEQ ID NO:11) is given in Yokota et al. (1986) which is incorporated herein by reference. The protein contains six cysteine residues and two N-linked glycosylation sites. The glycosylation sites are located in the A-B and C-D loops.

This example provides cysteine-added variants at any of the amino acids that comprise the N-linked glycosylation sites. This example also provides cysteine-added variants in the region proximal to the A helix, distal to the D helix, in the A-B loop, in the B-C loop, and in the C-D loop. Variants in which cysteine residues are introduced proximal to the first amino acid, H1, or distal to the final amino acid, S129, of the mature protein are provided.

The novel IL-4-derived molecules of this example can be formulated and tested for activity essentially as set forth in Examples 1 and 2, substituting, however, the appropriate assays and other considerations known in the art related to the specific proteins of this example.

EXAMPLE 11

IL-5

IL-5 is a differentiation and activation factor for eosinophils. The amino acid sequence of human IL-5 (SEQ ID NO: 12) is given in Yokota et al. (1987) which is incorporated herein by reference. The mature protein contains 115 amino acids and exists in solution as a disulfide-linked homodimer. The protein contains both O-linked and N-linked glycosylation sites.

This example provides cysteine-added variants in the region proximal to the A helix, distal to the D helix, in the A-B loop, in the B-C loop, and in the C-D loop. Variants in which cysteine residues are added proximal to the first amino acid or distal to the final amino acid in the mature protein are provided.

The novel IL-5-derived molecules of this example can be formulated and tested for activity essentially as set forth in Examples 1 and 2, substituting, however, the appropriate assays and other considerations known in the art related to the specific proteins of this example.

EXAMPLE 12

IL-6

IL-6 stimulates the proliferation and differentiation of many cell types. The amino acid sequence of human IL-6 (SEQ ID NO: 13) is given in Hirano et al. (1986) which is incorporated herein by reference. IL-6 is synthesized as a 212 amino acid preprotein that is cleaved to generate a 184 amino acid mature protein. The mature protein contains two sites for N-linked glycosylation and one site for O-glycosylation, at T137, T138, T142 or T143.

This example provides cysteine-added variants at any of the amino acids that comprise the N-linked glycosylation sites and at the O-linked glycosylation site. Also provided are cysteine-added variants in the region proximal to the A helix, distal to the D helix, in the A-B loop, in the B-C loop, and in the C-D loop. Variants in which cysteine residues are added proximal to the first amino acid or distal to the final amino acid of the mature protein also are provided.

The novel IL-6-derived molecules of this example can be formulated and tested for activity essentially as set forth in Examples 1 and 2, substituting, however, the appropriate assays and other considerations known in the art related to the specific proteins of this example.

EXAMPLE 13

IL-7

IL-7 stimulates proliferation of immature B cells and acts on mature T cells. The amino acid sequence of human IL-7 (SEQ ID NO: 14) is given in Goodwin et al. (1989) which is incorporated herein by reference. The protein is synthesized as a 177 amino acid preprotein that is cleaved to yield a 152 amino acid mature protein that contains three sites for N-linked glycosylation.

This example provides cysteine-added variants at any of the amino acids that comprise the N-linked glycosylation sites. This example also provides cysteine-added variants in the region proximal to the A helix, distal to the D helix, in the A-B loop, in the B-C loop, and in the C-D loop.

The novel IL-7-derived molecules of this example can be formulated and tested for activity essentially as set forth in Examples 1 and 2, substituting, however, the appropriate assays and other considerations known in the art related to the specific proteins of this example. Variants in which cysteine residues are added proximal to the first amino acid or distal to the final amino acid of the mature protein also are provided.

EXAMPLE 14

IL-9

IL-9 is a pleiotropic cytokine that acts on many cell types in the lymphoid, myeloid and mast cell lineages. IL-9 stimulates the proliferation of activated T cells and cytotoxic T lymphocytes, stimulates proliferation of mast cell precursors and synergizes with erythropoietin in stimulating immature red blood cell precursors. The amino acid sequence of human IL-9 (SEQ ID NO: 15) is given in Yang et al. (1989) which is incorporated herein by reference. IL-9 is synthesized as a precursor protein of 144 amino acids that is cleaved to yield a mature protein of 126 amino acids. The protein contains four potential N-linked glycosylation sites.

This example provides cysteine-added variants at any of the three amino acids that comprise the N-linked glycosylation sites. This example also provides cysteine-added variants in the region proximal to the A helix, distal to the D helix, in the A-B loop, in the B-C loop, and in the C-D loop. Variants in which cysteine residues are added proximal to the first amino acid or distal to the final amino acid of the mature protein also are provided.

The novel IL-9-derived molecules of this example can be formulated and tested for activity essentially as set forth in Examples 1 and 2, substituting, however, the appropriate assays and other considerations known in the art related to the specific proteins of this example.

EXAMPLE 15

IL-10

The amino acid sequence of human IL-10 (SEQ ID NO: 16) is given in Vieira et al. (1991) which is incorporated herein by reference. IL-10 is synthesized as a 178 amino acid precursor protein that is cleaved to yield a mature protein of 160 amino acids. IL-10 can function to activate or suppress the immune system. The protein shares structural homology with the interferons, i.e., it contains five amphipathic helices. The protein contains one N-linked glycosylation site.

This example provides cysteine-added variants at any of the three amino acids comprising the N-linked glycosylation site. This example also provides cysteine-added variants in the region proximal to the A helix, distal to the E helix, in the A-B loop, in the B-C loop, in the C-D loop and in the D-E loop. Variants in which cysteine residues are added proximal to the first amino acid or distal to the final amino acid of the mature protein also are provided.

The novel IL-10-derived molecules of this example can be formulated and tested for activity essentially as set forth in Examples 1 and 2, substituting, however, the appropriate assays and other considerations known in the art related to the specific proteins of this example.

EXAMPLE 16

IL-11

IL-11 is a pleiotropic cytokine that stimulates hematopoiesis, lymphopoeisis and acute phase responses. IL-11 shares many biological effects with IL-6. The amino acid sequence of human IL-11 (SEQ ID NO: 17) is given in Kawashima et al. (1991) and Paul et al. (1990) both incorporated herein by reference. IL-11 is synthesized as a precursor protein of 199 amino acids that is cleaved to yield a mature protein of 178 amino acids. There are no N-linked glycosylation sites in the protein. IL-11 has four major alpha helices referred to as helices A-D. Relative to the amino acid sequence shown in SEQ ID NO: 17, helix A encompasses amino acids 37-56, helix B encompasses amino acids 92-112, helix C encompasses amino acids 125-147 and helix D encompasses amino acids 173-196. Amino acids 1-21 of SEQ ID NO: 17 encompasses the IL-11 signal sequence.

This example provides cysteine-added variants in the region proximal to the A helix (amino acids 22-36 of SEQ ID NO: 17), distal to the D helix (amino acids 197-199 of SEQ ID NO: 17), in the A-B loop (amino acids 57-91 of SEQ ID NO:

17), in the B-C loop (amino acids 113-124 of SEQ ID NO: 17), and in the C-D loop (amino acids 148-172 of SEQ ID NO: 17). This Example also provides cysteine-added variants at the first three or last three amino acids in helices A, B, C and D. Variants in which cysteine residues are added proximal to the first amino acid of the mature protein (amino acid 22 of SEQ ID NO: 17) or distal to the final amino acid of the mature protein (amino acid 199 of SEQ ID NO: 17) also are provided.

The novel IL-11-derived molecules of this example can be formulated and tested for activity essentially as set forth in Examples 1 and 2, substituting, however, the appropriate assays and other considerations known in the art related to the specific proteins of this example.

EXAMPLE 17

IL-12 p35

IL-12 stimulates proliferation and differentiation of NK cells and cytotoxic T lymphocytes. IL-12 exists as a heterodimer of a p35 subunit and a p40 subunit. The p35 subunit is a member of the GH supergene family. The amino acid sequence of the p35 subunit (SEQ ID NO: 18) is given in Gubler et al. (1991) and Wolf et al. (1991) both incorporated herein by reference. p35 is synthesized as a precursor protein of 197 amino acids and is cleaved to yield a mature protein of 175 amino acids. The protein contains 7 cysteine residues and three potential N-linked glycosylation sites.

This example provides cysteine-added variants at any of the three amino acids that comprise the three N-linked glycosylation sites. This example also provides cysteine-added variants in the region proximal to the A helix, distal to the D helix, in the A-B loop, in the B-C loop, and in the C-D loop. These variants are provided in the context of the natural protein sequence or a variant protein in which the naturally occurring "free" cysteine residue has been changed to another amino acid, preferably serine or alanine. Variants in which cysteine residues are added proximal to the first amino acid or distal to the final amino acid of the mature protein also are provided.

The novel IL-12 p35-derived molecules of this example can be formulated and tested for activity essentially as set forth in Examples 1 and 2, substituting, however, the appropriate assays and other considerations known in the art related to the specific proteins of this example.

EXAMPLE 18

IL-13

IL-13 shares many biological properties with IL-4. The amino acid sequence of human IL-13 (SEQ ID NO: 19) is given in McKenzie et al. (1993) and Minty et al. (1993) both incorporated herein by reference. The protein is synthesized as a 132 amino acid precursor protein that is cleaved to yield a mature protein of 112 amino acids. The mature protein contains 5 cysteine residues and multiple N-linked glycosylation sites. A variant in which glutamine at position 78 is deleted due to alternative mRNA splicing has been described (McKenzie et al 1993)

This example provides cysteine-added variants at any of the three amino acids comprising the N-linked glycosylation sites. This example also provides cysteine-added variants in the region proximal to the A helix, distal to the D helix, in the A-B loop, in the B-C loop, and in the C-D loop. These variants are provided in the context of the natural protein sequence or a variant sequence in which the pre-existing "free" cysteine has been changed to another amino acid, preferably to alanine or serine. Variants in which cysteine residues are added proximal to the first amino acid or distal to the final amino acid of the mature protein also are provided.

The novel IL-13-derived molecules of this example can be formulated and tested for activity essentially as set forth in Examples 1 and 2, substituting, however, the appropriate assays and other considerations known in the art related to the specific proteins of this example.

EXAMPLE 19

IL-15

IL-15 stimulates the proliferation and differentiation of T cells, NK cells, LAK cells and Tumor Infiltrating Lymphocytes. IL-15 may be useful for treating cancer and viral infections. The sequence of IL-15 (SEQ ID NO: 20) is given in Anderson et al. (1995) which is incorporated herein by reference. IL-15 contains two N-linked glycosylation sites, which are located in the C-D loop and C-terminal end of the D helix. IL-15 encodes a 162 amino acid preprotein that is cleaved to generate a mature 114 amino acid protein. IL-15 contains four major alpha helices referred to as helices A-D. Helix A encompasses amino acids 1-15, helix B encompasses amino acids 38-57, helix C encompasses amino acids 65-78 and helix D encompasses amino acids 97-114.

This example provides cysteine-added variants at any of the three amino acids comprising the N-linked glycosylation sites in the C-D loop or C-terminal end of the D helix. This example also provides cysteine-added variants proximal to helix A, in the A-B loop (amino acids 16-37), the B-C loop (amino acids 58-64), the C-D loop (amino acids 79-96) or distal to helix D. This Example also provides cysteine-added variants at the first three or last three amino acids in helices A, B, C and D. Variants in which cysteine residues are added proximal to the first amino acid or distal to the final amino acid of the mature protein also are provided.

The novel IL-15-derived molecules of this example can be formulated and tested for activity essentially as set forth in Examples 1 and 2, substituting, however, the appropriate assays and other considerations known in the art related to the specific proteins of this example.

EXAMPLE 20

Macrophage Colony Stimulating Factor (M-CSF)

M-CSF regulates the growth, differentiation and function of monocytes. The protein is a disulfide-linked homodimer. Multiple molecular weight species of M-CSF, which arise from differential mRNA splicing, have been described. The amino acid sequence of human M-CSF and its various processed forms are given in Kawasaki et al (1985), Wong et al. (1987) and Cerretti et al (1988) which are incorporated herein by reference. Cysteine-added variants can be produced following the general teachings of this application and in accordance with the examples set forth herein.

The novel MCSF-derived molecules of this example can be formulated and tested for activity essentially as set forth in Examples 1 and 2, substituting, however, the appropriate assays and other considerations known in the art related to the specific proteins of this example.

EXAMPLE 21

Oncostatin M

Oncostatin M is a multifunctional cytokine that affects the growth and differentiation of many cell types. The amino acid sequence of human oncostatin M (SEQ ID NO: 21) is given in Malik et al. (1989) which is incorporated herein by reference. Oncostatin M is produced by activated monocytes and T lymphocytes. Oncostatin M is synthesized as a 252 amino acid preprotein that is cleaved sequentially to yield a 227 amino acid protein and then a 196 amino acid protein (Linsley et al., 1990). The mature protein contains O-linked glycosylation sites and two N-linked glycosylation sites. The protein is O-glycosylated at T160, T162 and S165. The mature protein contains five cysteine residues.

This example provides cysteine-added variants at either of the three amino acids comprising the N-linked glycosylation sites or at the amino acids that comprise the O-linked glycosylation sites. This example also provides cysteine-added variants proximal to helix A, in the A-B loop, in the B-C loop, in the C-D loop or distal to helix D. These variants are provided in the context of the natural protein sequence or a variant sequence in which the pre-existing "free" cysteine has been changed to another amino acid, preferably to alanine or serine. Variants in which cysteine residues are added proximal to the first amino acid or distal to the final amino acid of the mature protein also are provided.

The novel Oncostatin M-derived molecules of this example can be formulated and tested for activity essentially as set forth in Examples 1 and 2, substituting, however, the appropriate assays and other considerations known in the art related to the specific proteins of this example.

EXAMPLE 22

Ciliary Neurotrophic Factor (CNTF)

The amino acid sequence of human CNTF (SEQ ID NO: 22) is given in Lam et al. (1991) which is incorporated herein by reference. CNTF is a 200 amino acid protein that contains no glycosylation sites or signal sequence for secretion. The protein contains one cysteine residue. CNTF functions as a survival factor for nerve cells.

This example provides cysteine-added variants proximal to helix A, in the A-B loop, the B-C loop, the C-D loop or distal to helix D. These variants are provided in the context of the natural protein sequence or a variant sequence in which the pre-existing "free" cysteine has been changed to another amino acid, preferably to alanine or serine. Variants in which cysteine residues are added proximal to the first amino acid or distal to the final amino acid of the mature protein also are provided.

The novel CNTF-derived molecules of this example can be formulated and tested for activity essentially as set forth in Examples 1 and 2, substituting, however, the appropriate assays and other considerations known in the art related to the specific proteins of this example.

EXAMPLE 23

Leukemia Inhibitory Factor (LIF)

The amino acid sequence of LIF (SEQ ID NO: 23) is given in Moreau et al. (1988) and Gough et al. (1988) both incorporated herein by reference. The human gene encodes a 202 amino acid precursor that is cleaved to yield a mature protein of 180 amino acids. The protein contains six cysteine residues, all of which participate in disulfide bonds. The protein contains multiple O- and N-linked glycosylation sites. The crystal structure of the protein was determined by Robinson et al. (1994). The protein affects the growth and differentiation of many cell types.

This example provides cysteine-added variants at any of the three amino acids comprising the N-linked glycosylation sites or the O-linked glycosylation site. Also provided are cysteine-added variants proximal to helix A, in the A-B loop, the B-C loop, the C-D loop or distal to helix D. Variants in which cysteine residues are added proximal to the first amino acid or distal to the final amino acid of the mature protein also are provided.

The novel LIF-derived molecules of this example can be formulated and tested for activity essentially as set forth in Examples 1 and 2, substituting, however, the appropriate assays and other considerations known in the art related to the specific proteins of this example.

EXAMPLE 24

Expression and Purification of Wild Type Murine GM-CSF and Cysteine Muteins of Murine GM-CSF A. Expression and Purification of Wild Type Murine GM-CSF (muGM-CSF)

Cloning of a cDNA encoding wild type murine GM-CSF (WT muGM-CSF) is described in PCT/US01/16088, incorporated herein by reference in its entirety. Wild type muGM-CSF was expressed and purified using the following protocol. A fresh saturated overnight culture of E. coli strain W3110 transformed with pBBT257::stII-muGM-CSF, which encodes wild type muGM-CSF and is described in PCT/US01/16088, was inoculated at ~0.05 OD @ $A_{600}$ in LB containing 10 µg/ml tetracycline. The 400 ml culture was grown in a 2 L baffled shake flask at 28° C. in a gyrotory shaker water bath at ~250 rpm. When the culture reached a density of ~0.6 OD, IPTG was added to a final concentration of 0.5 mM. The induced culture was then incubated overnight for ~16 h. The cells were pelleted by centrifugation and frozen at −80° C. The cell pellet was thawed and treated with 5 mL of B-PER™ bacterial protein extraction reagent according to the manufacturer's (Pierce Chemical Company) protocols. The insoluble portion, and the bulk of the muGM-CSF protein, was recovered by centrifugation and resuspended in B-PER. This mixture was treated with lysozyme (200 µg/mL) for 10 min to further disrupt the bacterial cell walls, and $MgCl_2$ (10 mM final) and protease-free DNAse (2 µg/ml) were added. Insoluble mGM-CSF was collected by centrifugation and washed, by resuspension in water and recentrifugation, to remove most of the solubilized cell debris. For refolding, the resulting pellet containing insoluble muGM-CSF was dissolved in 10 ml of 8 M urea, 25 mM cysteine in 20 mM Tris Base. This mixture was stirred for 30 min at room temperature then diluted into 100 ml of 20 mM Tris, 40 µM copper sulfate, 15% glycerol, pH 8.0. This refold mixture was held at 4° C. for 2 days and then centrifuged and loaded onto a 5 ml Q-Sepharose HiTrap column (Amersham Pharmacia) equilibrated in 20 mM Tris, pH 8.0 (Buffer A). The bound proteins were eluted with a linear salt gradient from 0-35% Buffer B (1M NaCl, 20 mM Tris, pH 8). Column fractions were analyzed by non-reducing SDS-PAGE. muGM-CSF eluted at approximately 190 mM NaCl. Fractions containing primarily muGM-CSF were pooled.

The Q-Sepharose pool was adjusted to 30% ammonium sulfate by slow addition of solid ammonium sulfate. The mixture was warmed to room temperature before being loaded onto a 1 mL Phenyl HP HiTrap column (Amersham Pharmacia) previously equilibrated with 30% ammonium sulfate in 20 mM sodium phosphate, pH 7.5. The muGM-CSF was recovered from the column by elution with a reverse salt gradient (30% ammonium sulfate to 0% ammonium sulfate in 20 mM sodium phosphate, pH 7.5). The Phenyl HP column elution profile for GM-CSF showed a single major peak, eluting at a conductivity of approximately 1.28 mS/cm. Column fractions across the peak were analyzed by non-reducing SDS-PAGE. Fractions containing muGM-CSF and no visible contaminants were pooled. Protein concentrations were determined using a MicroBCA kit (Pierce Chemical Company).

B. Expression and Purification of T3C Murine GM-CSF

Construction of the muGM-CSF T3C cysteine mutein (substitution of cysteine for threonine at position 3 of muGM-CSF) is described in PCT/US01/16088. E. coli strain 3110 transformed with pBBT257::stII-muGM-CSF(T3C), which encodes the muGM-CSF T3C mutein and is described in PCT/US01/16088, was grown, induced and harvested using the protocols described in Example 24A for wild type muGM-CSF. The mutein was refolded and purified using the protocol described for wild type muGM-CSF. The mutein eluted from the Q-Sepharose column at approximately 220 mM NaCl and from the Phenyl HP column at a conductivity around 2 mS/CM. The mutein was recovered predominantly as a monomer, with an apparent molecular weight of approximately 14 kDa by non-reducing SDS-PAGE. Protein concentrations were determined using a MicroBCA kit (Pierce Chemical Company).

EXAMPLE 25

PEGylation of the muGM-CSF T3C Mutein

One milligram of muGM-CSF T3C protein prepared as described in Example 24B was diluted 3-fold with 100 mM Tris, pH 8, to a final concentration of 0.1 mg/ml protein. A 20-fold molar excess of 20 kDa maleimide-Polyethylene Glycol (20 kDa-mPEG-maleimide, Shearwater Corporation) was added followed by a 15× fold excess of TCEP (Pierce Chemical Company). The mixture was allowed to sit at room temperature for 4 hours before being diluted 5-fold with 20 mM Tris pH 8. The PEGylation reaction was next loaded on to a 1 ml Q-Sepharose HiTrap column (Amersham Pharmacia) equilibrated in 20 mM Tris, pH 8.0 (Buffer A). The bound proteins were eluted with a linear salt gradient from 0-35% Buffer B (1M NaCl, 20 mM Tris, pH 8). Column fractions were analyzed by non-reducing SDS-PAGE. The T3C protein modified with the 20 kDa maleimide-PEG eluted at approximately 90 mM NaCl. Fractions containing purified 20 kDa PEG-T3C protein were pooled. The T3C protein modified with a 10 kDa mPEG-maleimide (Shearwater Corporation) and a 40 kDa mPEG2 maleimide (Shearwater Corporation) were prepared using this same protocol.

EXAMPLE 26

Effects of Wild Type muGM-CSF and PEG-T3C GM-CSF Proteins on Hematopoiesis

The purpose of this study was to determine if the PEG-T3C GM-CSF proteins are effective at stimulating hematopoiesis in a mammal. The study was performed in rats because rats are predictive of the situation in other mammals, including humans. Similar types of experiments can be performed with other PEGylated GM-CSF cysteine muteins such as those described in Example 7 and in PCT/US01/16088 to demonstrate that these proteins are effective at stimulating hematopoiesis. The PEGylated GM-CSF cysteine muteins will be effective from the low μg/kg to the mg/kg range with the preferred level being between 25-300 μg/kg. Male Sprague Dawley rats weighing approximately 350 grams were given a single intravenous dose of wild type muGM-CSF, or the T3C mutein modified with 10 kDa-, 20 kDa and 40 kDa-maleimide PEGs. All rats were dosed at 100 μg/kg. The protein solutions were prepared at 100 μg/ml in phosphate buffered saline. Blood samples (0.4 ml) were collected at pre-dose, 0.25 h, 1.5h, 4h, 10 hr, 24h, 48h, 72 hr, 96h, 120h and 144h post-injection in an EDTA-coated tube. Blood samples were centrifuged and the plasma stored at −80° C. At pre-dose, 4, 10, 24, 48, 72, 96, 120 and 144 h post-injection approximately 0.2 ml of whole EDTA blood was removed prior to centrifugation and placed in an EDTA microtainer tube for submission to a commercial firm for a complete blood cell (CBC) analysis. Results of the CBC analyses are shown in Tables 1-5. The data show that the PEG-T3C GM-CSF proteins are effective at stimulating hematopoiesis in a mammal. In particular the proteins are effective at increasing blood levels of white blood cells, granulocytes (neutrophils and eosinophils), monocytes and lymphocytes.

TABLE 1

Effects of wild type muGM-CSF and 10 kDa-, 20 kDa- and 40 kDa-PEG T3C muGM-CSF on white blood cell counts

| | 10 kDa-PEG T3C (thousand cells/μl) | | | 20 kDa-PEG T3C (thousand cells/μl) | | | 40 kDa-PEG T3C (thousand cells/μl) | | | Wild type muGM-CSF (thousand cells/μl) | | |
|---|---|---|---|---|---|---|---|---|---|---|---|---|
| Time (h) | Rat 1 | Rat 2 | Rat 3 | Rat 4 | Rat 5 | Rat 6 | Rat 7 | Rat 8 | Rat 9 | Rat 10 | Rat 11 | Rat 12 |
| 0 | 9.2 | 9.0 | 8 | 7.8 | 7.7 | 4.3 | 3.5 | 3.7 | 6.6 | 3.1 | 6 | 2.4 |
| 4 | 19 | 11 | 11 | 13.8 | 8.8 | 14 | 12 | 7.4 | 11 | 11.3 | 17 | 10.7 |
| 10 | 12.5 | 12.7 | 11.8 | 14.6 | 12.3 | 14.1 | 15.9 | 9 | 12.5 | 10.5 | 17.5 | 10.2 |
| 24 | 8.2 | 9.2 | 8.1 | 15.2 | 11.4 | 9.5 | 16 | 8.7 | 15 | 6 | 8.7 | 5.8 |
| 48 | 8.9 | 9.6 | 8.4 | 10.9 | 11.5 | 8.9 | 27.9 | 13.3 | 17.1 | 5.7 | 9.1 | 6.4 |
| 72 | 9.2 | 10.9 | 8.3 | 8.7 | 9.6 | 8.8 | 17.8 | 11.2 | 17.7 | 5 | 13.1 | 7.3 |
| 96 | 12 | 11.6 | 9.2 | 13.1 | 14 | 14.1 | 22.6 | 14.4 | 20.1 | 8.4 | 11.9 | 11.2 |
| 120 | 9.2 | 8.9 | 7.2 | 10.4 | 11.5 | 11.8 | 16 | 14 | 13.8 | 9 | 10.3 | 14.9 |
| 144 | 5.3 | 6 | 3.3 | 4.5 | 2.2 | 4.8 | 4.8 | 8.2 | 4.7 | 6 | 6.6 | 7.1 |

TABLE 2

Effects of wild type muGM-CSF and 10 kDa-, 20 kDa- and 40 kDa-PEG T3C muGM-CSF on blood neutrophil counts

| Time (h) | 10 kDa-PEG T3C (cells/μl) | | | 20 kDa-PEG T3C (cells/μl) | | | 40 kDa-PEG T3C (cells/μl) | | | Wild type muGM-CSF (cells/μl) | | |
|---|---|---|---|---|---|---|---|---|---|---|---|---|
| | Rat 1 | Rat 2 | Rat 3 | Rat 4 | Rat 5 | Rat 6 | Rat 7 | Rat 8 | Rat 9 | Rat 10 | Rat 11 | Rat 12 |
| 0 | 1104 | 1350 | 1360 | 624 | 770 | 344 | 350 | 407 | 660 | 186 | 600 | 96 |
| 4 | 13300 | 5280 | 6050 | 9522 | 4644 | 9240 | 6240 | 5254 | 5610 | 6102 | 13600 | 8346 |
| 10 | 5625 | 5969 | 5546 | 10658 | 7134 | 9447 | 9815 | 6300 | 8250 | 4305 | 7875 | 5918 |
| 24 | 2378 | 1564 | 2106 | 7752 | 5928 | 3895 | 9280 | 6177 | 10650 | 1620 | 1914 | 2088 |
| 48 | 1157 | 1344 | 1680 | 3052 | 3450 | 1869 | 13392 | 7315 | 9234 | 1026 | 1820 | 1984 |
| 72 | 552 | 981 | 1079 | 1044 | 960 | 528 | 2492 | 4032 | 5487 | 450 | 1965 | 2628 |
| 96 | 1320 | 1508 | 1380 | 2882 | 2660 | 2679 | 5650 | 5904 | 5829 | 1428 | 2142 | 4368 |
| 120 | 828 | 1246 | 1008 | 1768 | 1265 | 1652 | 2400 | 5880 | 2622 | 1980 | 1339 | 8344 |
| 144 | 530 | 1020 | 132 | 1260 | 704 | 1008 | 960 | 3444 | 987 | 1260 | 1188 | 4118 |

TABLE 3

Effects of wild type muGM-CSF and 10 kDa-, 20 kDa- and 40 kDa-PEG T3C muGM-CSF on blood monocyte counts

| Time (h) | 10 kDa-PEG T3C (cells/μl) | | | 20 kDa-PEG T3C (cells/μl) | | | 40 kDa-PEG T3C (cells/μl) | | | Wild type muGM-CSF (cells/μl) | | |
|---|---|---|---|---|---|---|---|---|---|---|---|---|
| | Rat 1 | Rat 2 | Rat 3 | Rat 4 | Rat 5 | Rat 6 | Rat 7 | Rat 8 | Rat 9 | Rat 10 | Rat 11 | Rat 12 |
| 0 | 460 | 360 | 400 | 390 | 154 | 86 | 35 | 37 | 66 | 31 | 120 | 0 |
| 4 | 950 | 330 | 440 | 276 | 352 | 280 | 120 | 148 | 220 | 339 | 340 | 214 |
| 10 | 250 | 508 | 354 | 292 | 492 | 282 | 151 | 90 | 125 | 210 | 350 | 102 |
| 24 | 246 | 184 | 162 | 152 | 228 | 190 | 160 | 87 | 150 | 180 | 174 | 58 |
| 48 | 356 | 384 | 336 | 436 | 460 | 356 | 558 | 399 | 342 | 171 | 273 | 192 |
| 72 | 92 | 218 | 166 | 87 | 96 | 88 | 178 | 224 | 354 | 50 | 262 | 146 |
| 96 | 240 | 232 | 276 | 393 | 280 | 282 | 678 | 432 | 804 | 168 | 238 | 448 |
| 120 | 82 | 178 | 144 | 208 | 345 | 354 | 800 | 700 | 276 | 360 | 206 | 447 |
| 144 | 106 | 240 | 33 | 45 | 44 | 48 | 96 | 164 | 94 | 60 | 66 | 142 |

TABLE 4

Effects of wild type muGM-CSF and 10 kDa-, 20 kDa- and 40 kDa-PEG T3C muGM-CSF on blood eosinophil counts

| Time (h) | 10 kDa-PEG T3C (cells/μl) | | | 20 kDa-PEG T3C (cells/μl) | | | 40 kDa-PEG T3C (cells/μl) | | | Wild type muGM-CSF (cells/μl) | | |
|---|---|---|---|---|---|---|---|---|---|---|---|---|
| | Rat 1 | Rat 2 | Rat 3 | Rat 4 | Rat 5 | Rat 6 | Rat 7 | Rat 8 | Rat 9 | Rat 10 | Rat 11 | Rat 12 |
| 0 | 92 | 90 | 80 | 156 | 77 | 45 | 35 | 37 | 66 | 31 | 60 | 24 |
| 4 | 0 | 110 | 110 | 138 | 88 | 280 | 120 | 0 | 110 | 113 | 0 | 0 |
| 10 | 250 | 254 | 236 | 292 | 123 | 141 | 151 | 90 | 125 | 210 | 175 | 102 |
| 24 | 492 | 184 | 405 | 760 | 342 | 285 | 480 | 174 | 150 | 240 | 87 | 58 |
| 48 | 178 | 96 | 252 | 545 | 345 | 267 | 837 | 266 | 342 | 171 | 91 | 64 |
| 72 | 92 | 109 | 249 | 261 | 192 | 88 | 356 | 112 | 354 | 300 | 131 | 73 |
| 96 | 240 | 116 | 184 | 262 | 140 | 141 | 226 | 288 | 201 | 168 | 119 | 225 |
| 120 | 184 | 178 | 216 | 208 | 230 | 236 | 320 | 280 | 138 | 180 | 103 | 149 |
| 144 | 0 | 120 | 0 | 90 | 44 | 96 | 96 | 164 | 47 | 120 | 66 | 142 |

TABLE 5

Effects of wild type muGM-CSF and 10 kDa-, 20 kDa- and 40 kDa-PEG T3C muGM-CSF on blood lymphocyte counts

| Time (h) | 10 kDa-PEG T3C (cells/μl) | | | 20 kDa-PEG T3C (cells/μl) | | | 40 kDa-PEG T3C (cells/μl) | | | Wild type muGM-CSF (cells/μl) | | |
|---|---|---|---|---|---|---|---|---|---|---|---|---|
| | Rat 1 | Rat 2 | Rat 3 | Rat 4 | Rat 5 | Rat 6 | Rat 7 | Rat 8 | Rat 9 | Rat 10 | Rat 11 | Rat 12 |
| 0 | 7544 | 7200 | 6160 | 6630 | 6699 | 3827 | 3080 | 3219 | 5808 | 2852 | 5220 | 2280 |
| 4 | 4750 | 5280 | 4400 | 3864 | 3696 | 4200 | 5520 | 1998 | 5060 | 4746 | 3060 | 2140 |
| 10 | 6375 | 5969 | 5664 | 3358 | 4551 | 4230 | 4983 | 2520 | 4000 | 5775 | 9100 | 4080 |
| 24 | 5084 | 7268 | 5427 | 6536 | 4902 | 5130 | 6080 | 2262 | 4050 | 3960 | 6525 | 3596 |
| 48 | 7209 | 7776 | 6132 | 6867 | 7245 | 6408 | 13113 | 5320 | 7182 | 4332 | 6916 | 4160 |

TABLE 5-continued

Effects of wild type muGM-CSF and 10 kDa-, 20 kDa- and 40 kDa-PEG T3C muGM-CSF on blood lymphocyte counts

| Time (h) | 10 kDa-PEG T3C (cells/µl) | | | 20 kDa-PEG T3C (cells/µl) | | | 40 kDa-PEG T3C (cells/µl) | | | Wild type muGM-CSF (cells/µl) | | |
|---|---|---|---|---|---|---|---|---|---|---|---|---|
| | Rat 1 | Rat 2 | Rat 3 | Rat 4 | Rat 5 | Rat 6 | Rat 7 | Rat 8 | Rat 9 | Rat 10 | Rat 11 | Rat 12 |
| 72 | 8464 | 9592 | 6806 | 7306 | 8352 | 8096 | 14774 | 6832 | 11505 | 4200 | 10742 | 4453 |
| 96 | 10200 | 9976 | 7360 | 9563 | 10920 | 10998 | 16046 | 7776 | 13266 | 6636 | 9401 | 6160 |
| 120 | 8096 | 7298 | 5832 | 8216 | 9660 | 9558 | 12480 | 7140 | 10764 | 6480 | 8652 | 5960 |
| 144 | 4664 | 4620 | 3135 | 3105 | 1408 | 3648 | 3648 | 4428 | 3572 | 4560 | 5280 | 2698 |

EXAMPLE 27

Accelerating Recovery from Neutropenia with PEGylated GM-CSF Cysteine Mutein

The purpose of this study was to determine whether the PEGylated GM-CSF cysteine muteins could accelerate recovery from chemotherapy-induced neutropenia in a mammal. The study was performed in rats because rats are predictive of neutropenia in other mammals, including humans. Similar types of experiments can be performed with other PEGylated GM-CSF cysteine muteins such as those described in Example 7 and in PCT/US01/16088 to demonstrate that these proteins are effective at accelerating recovery from neutropenia. The PEGylated GM-CSF muteins will be effective from the low µg/kg (e.g., at least about 0.1 µg/kg) to the mg/kg range (e.g., at least about 0.1 mg/kg) with the preferred level being between 25-300 µg/kg.

Male Sprague Dawley rats (5 animals per group) weighing approximately 180 g were given an intraperitoneal dose of cyclophosphamide (CPA; 100 mg/kg) on Day 0. Wild type muGM-CSF, 20 kDa-PEG-T3C muGM-CSF or 40 kDa-PEG-T3C muGM-CSF prepared as described in Example 25 were then injected subcutaneously into rats at a dose of 100 µg/kg on Days 1-5. Protein samples were prepared in phosphate buffered saline. As controls, different groups of rats were injected with wild type muGM-CSF (Example 24) or vehicle (phosphate buffered saline). There was one group of rats that received no chemotherapy. A blood sample was collected at pre-dose (Day 0) and on Days 1-11 and 13 from all groups to perform a complete blood cell count (CBC) analysis. 400 µl of whole EDTA blood was removed and placed in an eppendorf tube for submission to an external lab for CBC analysis.

Results of the CBC analysis for white blood cells and neutrophils are shown in Tables 6 and 7. CPA-treatment caused a drastic drop in neutrophil and white blood cell counts by Day 1. It was found that the 20 kDa-PEG-T3C and 40 kDa-PEG-T3C muGM-CSF accelerated the recovery of neutropenia compared to the CPA-only treated group and the wild type muGM-CSF treated group. Neutrophil counts returned to normal levels (day 0 values) between Days 5 and 6 for the PEG-T3C muGM-CSF proteins versus between Day 9 and 10 for the CPA-only treated animals and the wild type muGM-CSF treated animals. White blood cell counts returned to normal levels between Days 6 and 8 for the PEG-T3C muGM-CSF proteins, whereas white blood cell counts in the CPA-treated animals and the wild type muGM-CSF treated animals had not returned to normal levels (day 0 values) even by day 13 when the experiment was terminated. Similar types of experiments could be performed using different dosing schedules, e.g., a single injection on day 1, every other day injections or every third day injections, or weekly injections to determine an optimum dosing schedule for the PEG-GM-CSF cysteine muteins.

TABLE 6

Effects of multiple doses of muGM-CSF, 20 kDa-PEG-T3C and 40 kDa-PEG-T3C on white blood cell (WBC) counts in neutropenic rats
White Blood Cells (1000/µL)*

| Time (Day) | Control (Vehicle) | CPA-alone | muGM-CSF | 20 kDa-PEG-T3C | 40 kDa-PEG-T3C |
|---|---|---|---|---|---|
| 0 | 9.8 +/− 0.5 | 9.4 +/− 0.5 | 9.8 +/− 0.5 | 9.8 +/− 0.8 | 10.4 +/− 0.3 |
| 1 | 9.1 +/− 0.2 | 3.4 +/− 0.5 | 3.3 +/− 0.2 | 3.1 +/− 0.2 | 3.3 +/− 0.3 |
| 2 | 13.6 +/− 0.5 | 2.2 +/− 0.2 | 1.6 +/− 0.2 | 1.4 +/− 0.1 | 2.3 +/− 0.3 |
| 3 | 11.2 +/− 0.5 | 1.6 +/− 0.6 | 1.2 =/− 0.3 | 4.3 +/− 0.5 | 3.7 +/− 0.4 |
| 4 | 13.6 +/− 0.5 | 2.3 +/− 0.2 | 1.6 +/− 0.2 | 1.4 +/− 0.1 | 2.3 +/− 0.3 |
| 5 | 11.2 +/− 1.0 | 1.0 +/− 0.1 | 1.0 +/− 0.1 | 0.9 +/− 0.1 | 1.3 +/− 0.4 |
| 6 | 10.4 +/− 0.4 | 1.4 +/− 0.3 | 1.4 +/− 0.1 | 4.3 +/− 0.6 | 4.0 +/− 1.1 |
| 7 | 11.6 +/− 0.6 | 2.2 +/− 0.3 | 3.4 +/− 0.3 | 11.1 +/− 1.1 | 8.7 +/− 1.4 |
| 8 | 11.8 +/− 0.5 | 3.0 +/− 0.2 | 3.8 +/− 0.3 | 10.6 +/− 0.7 | 11.4 +/− 1.4 |
| 9 | 14.6 +/− 0.4 | 3.6 +/− 0.2 | 4.9 +/− 0.4 | 10.1 +/− 1.0 | 12.3 +/− 2.1 |
| 10 | 11.3 +/− 0.8 | 4.8 +/− 0.5 | 6.5 +/− 0.3 | 7.2 +/− 0.6 | 9.6 +/− 1.9 |
| 11 | 11.1 +/− 0.9 | 5.0 +/− 0.3 | 6.5 +/− 0.2 | 5.7 +/− 0.4 | 6.2 +/− 0.9 |
| 13 | 13.2 +/− 0.4 | 6.6 +/− 0.5 | 6.2 +/− 0.3 | 5.0 +/− 0.8 | 5.1 +/− 0.2 |

*WBC counts are means ± SE from 5 rats/group

TABLE 7

Effects of multiple doses of muGM-CSF, 20 kDa-PEG-T3C and 40 kDa-PEG-T3C on absolute neutrophil counts in neutropenic rats Absolute Neutrophil Count (cells/μL)*

| Time (Day) | Control (Vehicle) | CPA-alone | muGM-CSF | 20 kDa-PEG-T3C | 40 kDa-PEG-T3C |
|---|---|---|---|---|---|
| 0 | 1333 +/− 90 | 1352 +/− 153 | 1328 +/− 111 | 1330 +/− 177 | 1335 +/− 103 |
| 1 | 1778 +/− 121 | 902 +/− 191 | 700 +/− 38 | 735 +/− 78 | 790 +/− 68 |
| 2 | 1659 +/− 280 | 602 +/− 82 | 154 +/− 14 | 566 +/− 64 | 1181 +/− 217 |
| 3 | 1688 +/− 233 | 428 +/− 193 | 277 +/− 91 | 3060 +/− 333 | 2620 +/− 238 |
| 4 | 1659 +/− 280 | 625 +/− 101 | 154 +/− 14 | 566 +/− 64 | 1181 +/− 217 |
| 5 | 1108 +/− 187 | 130 +/− 66 | 152 +/− 41 | 236 +/− 57 | 370 +/− 155 |
| 6 | 1355 +/− 222 | 103 +/− 35 | 189 +/− 49 | 2041 +/− 369 | 2215 +/− 844 |
| 7 | 1445 +/− 196 | 227 +/− 53 | 593 +/− 136 | 6366 +/− 759 | 4338 +/− 999 |
| 8 | 1786 +/− 240 | 338 +/− 35 | 631 +/− 220 | 4870 +/− 321 | 5171 +/− 836 |
| 9 | 2371 +/− 221 | 676 +/− 161 | 1156 +/− 197 | 3277 +/− 436 | 3636 +/− 1346 |
| 10 | 2178 +/− 279 | 1617 +/− 228 | 2573 +/− 135 | 2508 +/− 332 | 2636 +/− 887 |
| 11 | 1964 +/− 164 | 2337 +/− 183 | 2952 +/− 360 | 2296 +/− 304 | 2161 +/− 313 |
| 13 | 1830 +/− 159 | 2244 +/− 166 | 1843 +/− 172 | 1502 +/− 222 | 1433 +/− 72 |

*Neutrophil counts are means ± SE for 5 rats/group

EXAMPLE 28

Expression, Purification and PEGylation of EPO Cysteine Muteins

A detailed background of protein expression, purification, PEGylation and analysis, as well as useful sites for introducing free cysteine residues into EPO are described in Example 2 and PCT/US01/16088, which is incorporated herein by reference in its entirety. Example 2 and PCT/US01/16088 describe cysteine muteins of human EPO that can be modified with cysteine-reactive PEG reagents and retain activity in in vitro bioactivity assays. The purpose of the studies outlined below was to determine whether the PEGylated EPO cysteine muteins stimulated red blood cell formation (as measured by an increase in blood hematocrit levels) in normal animals. Similar types of experiments can be performed with other PEGylated EPO cysteine muteins such as those described in Example 2 and PCT/US01/16088 to demonstrate that these proteins are effective at increasing red blood cell formation (hematocrit levels) in mice. The studies were performed in mice because mice are predictive of erythropoiesis in other mammals, including humans.

An EPO cysteine mutein, *167C, was created by adding a cysteine residue following the last amino acid, R166, in the EPO coding sequence. Construction of the *167C EPO cysteine mutein is described in PCT/US00/00931. EPO cysteine mutein *167C was expressed in CHO cells and secreted into the culture medium as follows. The DNA encoding the EPO mutein was preceded by the natural EPO secretory signal sequence and followed by a seven amino acid linker sequence SGGSGGS and a Flag peptide sequence (Kodak), DYKD-DDDK. This EPO gene was cloned into the expression vector pcDNA 3.1 (Invitrogen) by standard recombinant DNA techniques. The resulting plasmid is termed pBBT410. A stably transformed CHO cell line expressing the EPO mutein was constructed as follows. The CHO DXB11 DHFR deficient cell line was obtained from Dr. Lawrence Chasin (Columbia University). The cells were co-transfected with plasmid pdhfr 3.2 (American Type Culture Collection, Rockville, Md.; catalogue #37166) and plasmid pBBT410, which is described in PCT/US00/19336, using lipofectamine reagent and Opti-MEM media (Invitrogen Corporation). After 3 days of growth in non-selective media (Alpha MEM media containing 10% dialyzed fetal calf serum, 1 μM sodium hypoxanthine, 16 μM thymidine), the cells were split 1:10 and 1:20 into selective media (Alpha MEM media containing 10% dialyzed fetal calf serum, 300 μg/ml geneticin (Invitrogen Corporation). After about 2 weeks, stable clones were picked with the aid of cloning rings. Clones were screened for those that express EPO protein by Western blot analysis of the conditioned media using anti-EPO antisera (R&D Systems, Inc.) and by ELISA using Quantikine human EPO ELISA kits obtained from R&D Systems, Inc. One positive clone was selected for production of protein. Large amounts of the *167C EPO cysteine mutein were obtained by seeding twenty T150 flasks with clone and allowing the cells to grow to confluency in selective media. Once the cells reached confluency, conditioned medium was collected on days 3, 6 and 9. The medium was clarified by centrifugation and frozen at −80° C.

The *167C EPO cysteine mutein was purified from the conditioned media as follows. Approximately 700 ml of conditioned media was filtered through a 0.2 um filter. A 1M solution of cystine was then added to the conditioned media to a final concentration of 2.5 mM. The use of cystine to assist purification of EPO cysteine muteins is described in PCT/US00/00931. In some of the purification runs, NaCl was added to a final concentration of 150 mM. Anti-flag M2 affinity resin (Sigma Aldrich Company, catalogue #A2220) was washed with Buffer B (0.1M Glycine pH 3.0, 0.05% Tween 20, 20% Glycerol) and then with Buffer A (50 mM Tris pH 7.5, 150 mM NaCl, 0.05% Tween 20, 20% Glycerol). In some experiments the glycerol concentration in Buffers A and B was lowered from 20% to 10%. The washed resin was batch loaded with the filtered conditioned media on a roller bottle apparatus at 4° C., overnight. The affinity resin was collected in a column and washed with Buffer A until the A280 reached baseline. Bound proteins were eluted with Buffer B. Fractions were collected and immediately neutralized to approximately pH 8. The unbound material from the first affinity column was rebatched with the anti-flag resin and the affinity column purification procedure repeated. Fractions containing *167C-EPO-flag protein from each column run were pooled, diluted 5-10-fold with Buffer C (20 mM Bis-Tris pH 7.0, 0.01% Tween 20, 10% Glycerol) and loaded on a 1 ml HiTrap Q-Sepharose column (Amersham Pharmacia). Bound proteins were eluted with Buffer D (20 mM Bis-Tris pH 7.0, 0.01% Tween 20, 10% Glycerol, 1M NaCl). In some purification runs Buffers C and D contained 10 mM Tris pH 7.5 rather than 20 mM Bis-Tris pH 7.0 and Buffer D contained 0.5M NaCl rather than 1M NaCl. Fractions containing the *167C-EPO-flag protein were pooled and loaded (in 500 ul loads) onto a Superdex 200 10/30 column (Amersham Pharmacia) pre-equilibrated with 50 mM sodium phosphate pH 7.5, 150 mM NaCl, 15% glycerol. Fractions containing the *167C-EPO flag protein were pooled and the protein concentration determined using a Bradford Dye Binding assay kit (Bio-Rad Laboratories) that uses bovine serum albumin as the standard. Approximately 1.4 mg of *167C-EPO flag protein was recovered from the 700 ml of conditioned media.

The *167C-EPO-flag protein can be captured on a Blue-Sepharose column prior to purification of the protein using the Anti-flag M2 affinity resin. In these experiments, cystine is added to the conditioned media to a final concentration of 5 mM cystine and the pH is adjusted to pH 5 with glacial acetic acid. The media is then filtered through a 0.2 μm filter and loaded onto a 5 ml HiTrap Blue-Sepharose column (Amersham Pharmacia) that has been pre-equilibrated with Buffer E (20 mM sodium acetate pH 5.0, 100 mM NaCl, 5 mM $CaCl_2$). The column is then washed with four column volumes of Buffer F (20 mM Tris pH 6.5, 5 mM $CaCl_2$) and the bound proteins eluted with Buffer G (100 mM Tris pH 9.2, 1.5 M NaCl, 5 mM $CaCl_2$, 0.01% Tween 20). Fractions containing the *167C-EPO-flag protein are pooled and can be further purified using the Anti-flag affinity, Q-Sepharose and Superdex 200 columns as described above.

The following procedure was used to modify about 1 mg of *167C-EPO-flag protein with maleimide-PEGs. Maleimide-PEGs of various sizes (2-40 kDa) are available from Shearwater, Inc. (Huntsville, Ala.). Other types of cysteine-reactive PEGs, such as vinylsulfone PEGs, can be substituted for maleimide PEGs, if desired. The *167C-EPO-flag protein was incubated for 2 hours at room temperature in a pH 8.0 solution containing a 20-fold molar excess of TCEP [(Tris(2-carboxyethyl)phosphine)-HCl] (Pierce Chemical Company), a 20-fold molar excess of 20 kDa-maleimide PEG (20 kDa-mPEG, Shearwater, Inc.) or 40 kDa-maleimide-PEG (40 kDa-mPEG2, Shearwater, Inc.), and 0.01% Tween 20. An additional 10-fold molar excess of TCEP and 10-fold molar excess of maleimide-PEG were then added to the reaction and the mixture incubated for another 1 hour at room temperature. The PEGylation reaction was then diluted 10-fold with Buffer H (20 mM Bis-Tris pH 7.0, 0.01% Tween 20, 10% glycerol) and loaded onto a 1 ml HiTrap Q-Sepharose column (Amersham Pharmacia) that had been pre-equilibrated with Buffer H. Bound proteins were eluted with a 50% step of Buffer H containing 1M NaCl. In some experiments Buffer H contained 20 mM Tris pH 7.5 rather than 20 mM Bis-Tris pH 7.0. Fractions containing the PEG-*167C-flag protein were pooled and loaded (approximately 500 μl per column run) onto a Superdex 200 10/30 column pre-equilibrated with 50 mM sodium phosphate pH 7.5, 150 mM NaCl, 10% glycerol. Fractions containing the mono-PEGylated *167C-EPO-flag protein were pooled, diluted 10-fold with Buffer C (20 mM Bis-Tris pH 7.0, 0.01% Tween 20, 10% glycerol) and loaded onto a 1 ml HiTrap Q-Sepharose column (Amersham Pharmacia) pre-equilibrated with Buffer C. Bound proteins were eluted with a 50% step of Buffer D (20 mM Bis-Tris pH 7.0, 0.01% Tween 20, 10% glycerol, 1M NaCl). Fractions containing the mono-PEGylated *167C-EPO-flag protein were pooled and protein concentration determined using a Bradford dye binding assay kit (Bio-Rad Laboratories), using bovine serum albumin as the standard. Approximately 560 μg of 20 kDa-mono-PEGylated *167C-EPO-flag protein was recovered from 1 mg of starting protein. Approximately 700 ug of 40 kDa-mono-PEGylated *167C-EPO-flag protein was recovered from 1.5 mg of starting protein.

EXAMPLE 29

Use of PEG-*167C-Epo to Increase Hematocrit Levels in Mice

In this study, it was shown that times per week (TIW) administration of 40 kDa-monoPEGylated *167C-EPO-flag is effective at increasing red blood cell formation (hematocrit levels) in mice. Forty mice (strain CD-1) were used in the study. After arrival, the animals were allowed to acclimatize to their environment for 10 days. The animals were then divided in 5 groups, 8 mice/group. Group 1 mice did not receive any injections. Group 2 mice were injected subcutaneously TIW for three weeks with Dulbecco's PBS, 10 ml/kg, containing 250 μg/ml of murine albumin ("vehicle"). The remaining three groups were treated TIW for three weeks with various doses of 40 kDa PEG-*167C-EPO-Flag suspended in vehicle. Groups 3, 4, and 5 received TIW injections 2.5 μg/kg, 5 μg/kg, and 20 μg/kg per injection of 40 kDa PEG-*167C-EPO-Flag, respectively. Retroorbital blood samples were taken from all groups twice/week, starting on day 0 (where day 1 was the first day of injections) and hematocrits measured. Animals received injections of test samples on days 1, 4, 6, 8, 11, 13, 15, 18 and 20. Blood samples were drawn for hematocrit measurements on days 0, 5, 8, 12, 15, 19 and 22. For each group, the average hematocrit and standard error of the mean (S.E.M.) was calculated over time (Table 8). The data show that all doses of the 40 kDa-PEG-*167C-EPO protein were effective at increasing hematocrit levels in the mice using the TIW dosing frequency.

TABLE 8

40K-PEG-*167C EPO Increases Hematocrit Levels In Mice

| | Hematocrit (%) ± SEM | | | | |
|---|---|---|---|---|---|
| Day | Group 1 No injections | Group 2 Vehicle | Group 3 PEG-*167C 2.5 μg/kg | Group 4 PEG-*167C 5 μg/kg | Group 5 PEG-*167C 20 μg/kg |
| 0 | 45.6 ± 1.0 | 45.6 ± 0.7 | 45.9 ± 0.3 | 45.9 ± 0.3 | 45.9 ± 0.1 |
| 5 | 44.2 ± 0.2 | 45.6 ± 1.2 | 47.3 ± 1.1 | 49.8 ± 0.7 | 54.7 ± 1.1 |
| 8 | 43.9 ± 0.3 | 44.2 ± 0.7 | 49.9 ± 1.1 | 54.5 ± 0.9 | 63.0 ± 1.1 |
| 12 | 46.5 ± 0.5 | 46.1 ± 0.9 | 52.7 ± 1.0 | 59.2 ± 1.6 | 68.4 ± 2.0 |
| 15 | 45.9 ± 0.4 | 44.6 ± 0.8 | 53.5 ± 1.3 | 60.7 ± 2.4 | 73.4 ± 1.4 |
| 19 | 46.2 ± 0.6 | 44.1 ± 0.7 | 52.8 ± 0.9 | 62.8 ± 2.4 | 72.9 ± 0.9 |
| 22 | 44.8 ± 0.9 | 46.0 ± 1.1 | 53.2 ± 1.6 | 66.0 ± 2.8 | 72.9 ± 3.1 |

EXAMPLE 30

20 kDa-PEG-*167C-Epo and 40 kDa-PEG-*167C-Epo Increase Hematocrit Levels in Mice when Administered Once per Week In this study, it was demonstrated that once per week (QW) administration of 20 kDa PEG-*167C-EPO-flag and 40 kDa-PEG-*167C-EPO-flag was effective at increasing red blood cell formation (hematocrit levels) in mice. Forty mice (strain CD-1) were used in the study. After arrival, the animals were allowed to acclimatize to their environment for 10 days. The animals were then divided in 5 groups, 8 mice/group. Group 1 was injected subcutaneously QW for three weeks with Dulbecco's PBS, 10 ml/kg, containing 250 μg/ml of murine albumin ("vehicle"). The remaining four groups were treated QW for three weeks with various doses of 20 kDa PEG-*167C-EPO-flag or 40 kDa PEG-*167C-EPO-flag suspended in vehicle. Groups 2, 3, and 4 received once per week injections of 23.5 µg/kg, 47 µg/kg, and 94 µg/kg of 40 kDa PEG-*167C-EPO-flag, respectively. Group 5 received once per week injections of 31 µg/kg of 20 kDa PEG-*167C-EPO-flag. Retroorbital blood samples were taken from all groups twice/week, starting on day 0 (where day 1 was the first day of injections), and hematocrits measured. Mice received injections of test samples on days 1, 8, and 15. Mice were bled and their hematocrits measured on days 0, 5, 8, 12, 15, 19 and 22. For each group, the average hematocrit and standard error of the mean was calculated and is shown in Table 9. The data show that all doses of the 20 kDa-PEG-*167C-EPO and 40 kDA-PEG-*167C-EPO were effective at increasing hematocrit levels in the mice using the once per week dosing frequency. Similar experiments can be performed using less frequent dosing schedules such as once every 2-3 weeks. Similar experiments can be performed with other EPO cysteine muteins, and EPO cysteine muteins that do not contain the Flag peptide or peptide linker.

TABLE 9

20 kDa-PEG-*167C-Epo and 40 kDa-PEG-*167C-Epo increase hematocrit levels in mice when administered once per week

| | | Hematocrit (%) ± s.e.m. | | | |
|---|---|---|---|---|---|
| Day | Group 1 Vehicle | Group 2 40K-PEG-*167C-EPO 23.5 µg/kg | Group 3 40K-PEG-*167C-EPO 47 µg/kg | Group 4 40K-PEG-*167C-EPO 94 µg/kg | Group 5 20K-PEG-*167C-EPO 31 µg/kg |
| 1 | 43.12 ± 1.43 | 43.88 ± 0.45 | 44.13 ± 0.34 | 44.05 ± 0.16 | 44.09 ± 0.07 |
| 5 | 42.92 ± 0.62 | 53.66 ± 0.57 | 50.26 ± 0.97 | 53.29 ± 1.84 | 55.16 ± 0.76 |
| 8 | 45.50 ± 0.65 | 56.59 ± 0.74 | 57.07 ± 1.12 | 62.06 ± 2.07 | 60.30 ± 1.44 |
| 12 | 45.74 ± 0.93 | 59.11 ± 0.94 | 59.18 ± 1.57 | 68.48 ± 1.37 | 63.00 ± 0.97 |
| 15 | 45.78 ± 0.98 | 59.17 ± 1.38 | 62.26 ± 1.85 | 69.86 ± 1.76 | 62.93 ± 1.78 |
| 19 | 46.75 ± 1.02 | 57.36 ± 1.54 | 65.45 ± 2.36 | 68.06 ± 2.67 | 64.06 ± 2.51 |
| 22 | 46.08 ± 0.80 | 52.73 ± 3.08 | 62.87 ± 2.65 | 62.99 ± 3.40 | 62.46 ± 2.25 |

EXAMPLE 31

Preparation, Expression, Purification of PEGylated G-CSF Cysteine Muteins

A detailed background of protein expression, purification, PEGylation and analysis, as well as useful sites for introducing free cysteine residues into G-CSF are described in Example 5 and PCT/US01/16088, which is incorporated herein by reference in its entirety. Example 5 and PCT/US01/16088 describe cysteine muteins of human G-CSF that can be modified with cysteine-reactive PEG reagents and retain activity in in vitro bioactivity assays.

The purpose of the studies outlined below was to determine whether the PEGylated G-CSF cysteine muteins could accelerate recovery from chemotherapy-induced neutropenia in a mammal. The studies were performed in rats because rats are predictive of neutropenia in other mammals, including humans. Similar types of experiments can be performed with other PEGylated G-CSF cysteine muteins such as those described in Example 5 and PCT/US01/16088 to demonstrate that these proteins are effective at accelerating recovery from neutropenia.

The G-CSF L3C and A141C cysteine muteins are described in Example 5. Construction, expression and purification of G-CSF-L3C (C17S/L3C) and G-CSF-A141C (C17S/A141C) were performed as described in PCT/US01/16088 except the protein refolding was performed overnight rather than for 2 days. The PEGylation of G-CSF-L3C (C17S/L3C) was done as previously outlined in PCT/US01/16088. The protein was modified with 20 kDa-mPEG (Cat. #2D2M0P01) and 40 kDa-branched mPEG (Cat. #2D3X0T01) obtained from Shearwater, Inc. Concentration of the purified protein was measured using a Bradford dye binding assay using bovine serum albumin as the standard. The purified protein was stored frozen at –80° C. until use.

EXAMPLE 32

Treatment of Neutropenia with Multiple Doses of PEGylated G-CSF Cysteine Muteins In experiments to evaluate the ability of multiple doses of G-CSF PEGylated cysteine muteins to accelerate recovery from chemotherapy-induced neutropenia, male Sprague Dawley rats (5 animals per group) weighing approximately 180 g were given an intraperitoneal dose of cyclophosphamide CPA (100 mg/kg) on Day 0. 20 kDa-PEGylated (C17S/L3C) was then injected subcutaneous into rats at a dose of 100 µg/kg on Days 1-5. Protein samples were prepared in phosphate buffered saline. As controls, different groups of rats were injected with commercial G-CSF (Neupogen, Amgen, Inc.) or vehicle (phosphate buffered saline). There was one group of rats that received no chemotherapy. A blood sample was collected at pre-dose (Day 0) and on Days 1-10 and 12 from all groups to perform a complete blood cell count (CBC) analysis. 400 µl of whole EDTA blood was removed and placed in an eppendorf tube for submission to an external lab for CBC analysis.

Results of the CBC analysis for white blood cells and neutrophils are shown in Tables 10 and 11. CPA-treatment caused a drastic drop in neutrophil and white blood cell counts by Day 1. It was shown that the 20 kDa-PEG-G-CSF cysteine mutein accelerated the recovery of neutropenia compared to the CPA-only treated group (neutrophil and white blood cell counts approached normal levels between Days 4 and 5 versus Day 8 for CPA treated animals). Although Neupogen stimulated time-dependent increases in neutrophil counts and white blood cell counts, the PEGylated G-CSF cysteine mutein was far superior to Neupogen, stimulating greater and longer lasting increases in these parameters. In addition, recovery began up to a day earlier with the 20 kDa-PEGylated G-CSF (C17S/L3C) cysteine mutein.

TABLE 10

Effects of multiple doses of Neupogen or 20 kDa-PEG-GCSF (C17S/L3C) on white blood cell (WBC) counts in neutropenic rats White Blood Cells (1000/μL)*

| Time (Day) | Control (Vehicle) | CPA-alone | G-CSF | 20 kDa-PEG-G-CSF (C17S/L3C) |
|---|---|---|---|---|
| 0 | 10.1 ± 0.6 | 9.6 ± 1.7 | 9.4 ± 0.5 | 11.4 ± 0.8 |
| 1 | 10.2 ± 0.5 | 2.7 ± 0.3 | 2.3 ± 0.1 | 2.8 ± 0.2 |
| 2 | 12.6 ± 1.1 | 2.2 ± 0.3 | 4.3 ± 0.3 | 4.3 ± 0.9 |
| 3 | 11.2 ± 1.2 | 2.2 ± 0.1 | 1.2 ± 0.1 | 1.6 ± 0.2 |
| 4 | 11 ± 1.3 | 1.4 ± 0.1 | 1.5 ± 0.1 | 1.9 ± 0.2 |
| 5 | 10.6 ± 1.5 | 1.7 ± 0.2 | 3.7 ± 0.6 | 8.2 ± 1.0 |
| 6 | 11 ± 0 | 3.6 ± 0.7 | 10.8 ± 4.9 | 24.5 ± 2.3 |
| 7 | 11.8 ± 0.6 | 3.6 ± 0.1 | 5.0 ± 0.5 | 28.1 ± 2.6 |
| 8 | 12 ± 0.4 | 4.8 ± 0.5 | 5.9 ± 0.8 | 24.4 ± 3.0 |
| 9 | 13.2 ± 0.4 | 8.9 ± 1.2 | 7.6 ± 0.9 | 17.8 ± 2.2 |
| 10 | 10.2 ± 0.6 | 8.4 ± 1.1 | 7.0 ± 0.6 | 11.3 ± 1.4 |
| 12 | 10.3 ± 0.7 | 9.8 ± 1.2 | 4.3 ± 0.4 | 6.5 ± 1.1 |

*WBC counts are means ± SE from 5 rats/group

TABLE 11

Effects of multiple doses of Neupogen and 20 kDa-PEG-GCSF (C17S/L3C) on neutrophil counts in neutropenic rats
Absolute Neutrophil Count (cells/μL)*

| Time (Day) | Control (Vehicle) | CPA-alone | G-CSF | 20 kDa-PEG-G-CSF (C17S/L3C) |
|---|---|---|---|---|
| 0 | 1374 ± 135 | 1350 ± 281 | 1388 ± 143 | 1397 ± 72 |
| 1 | 1236 ± 123 | 484 ± 39 | 488 ± 65 | 773 ± 219 |
| 2 | 1796 ± 156 | 837 ± 163 | 2151 ± 182 | 2277 ± 843 |
| 3 | 1390 ± 35 | 531 ± 113 | 203 ± 65 | 680 ± 77 |
| 4 | 1328 ± 274 | 263 ± 36 | 434 ± 138 | 475 ± 95 |
| 5 | 1285 ± 139 | 237 ± 69 | 1644 ± 350 | 4872 ± 840 |
| 6 | 1760 ± 110 | 327 ± 9 | 6975 ± 3789 | 18621 ± 2144 |
| 7 | 1837 ± 197 | 303 ± 93 | 1971 ± 262 | 20973 ± 2478 |
| 8 | 1573 ± 194 | 1558 ± 461 | 2171 ± 410 | 15157 ± 2288 |
| 9 | 1804 ± 257 | 4214 ± 929 | 3911 ± 573 | 9159 ± 1094 |
| 10 | 1923 ± 281 | 4634 ± 1022 | 3911 ± 398 | 6223 ± 1364 |
| 12 | 1430 ± 161 | 49.31 ± 1188 | 1567 ± 251 | 2960 ± 863 |

*Neutrophil counts are means ± SE for 5 rats/group

EXAMPLE 33

Treatment of Neutropenia with a Single Dose of PEGylated G-CSF Cysteine Muteins In experiments to evaluate the ability of a single dose of PEGylated G-CSF cysteine mutein (C17S/L3C) to accelerate recovery from chemotherapy-induced neutropenia, male Sprague Dawley rats (5 animals per group) weighing approximately 180 g were given an intraperitoneal dose of CPA (100 mg/kg) on Day 0. 20 kDa- or 40 kDa-PEGylated G-CSF cysteine muteins was then injected subcutaneous into rats as a single dose of 100 μg/kg on Day 1. Protein samples were prepared in phosphate buffered saline. As controls, different groups of rats were injected with commercial G-CSF (Neupogen, Amgen, Inc.) or vehicle (phosphate buffered saline). There was one group of rats that received no chemotherapy. A blood sample was collected at pre-dose (Day 0) and on Days 1-10 and 12 from all groups to perform a complete blood cell count (CBC) analysis. 400 μl of whole EDTA blood was removed and placed in an eppendorf tube for submission to an external lab for CBC analysis.

Results of the CBC analysis for white blood cells and neutrophils are shown in Tables 12 and 13. CPA-treatment caused a significant decrease in neutrophil and white blood cell counts by Day 1. The 20 kDa- or 40 kDa-PEGylated G-CSF cysteine muteins accelerated the recovery of neutropenia compared to the CPA-only treated group (neutrophil and white blood cell counts reached normal levels between Days 4 and 5 versus Day 9 for the CPA-only control). Neupogen provided little benefit when given as a single dose, whereas the 20 kDa- or 40 kDa-PEGylated G-CSF cysteine mutein stimulated significant increases in both neutrophils and white blood cells compared to CPA-only treated animals. Animals receiving 20 kDa- or 40 kDa-PEGylated G-CSF cysteine mutein showed accelerated recovery of neutrophils and white blood cells as compared to animals receiving only CPA.

A similar experiment was performed with the G-CSF (C17S/A141C) cysteine mutein modified with 20 kDa- and 40 kDa-maleimide PEGs. Male Sprague Dawley rats (5 animals per group) weighing approximately 180 g were given an intraperitoneal dose of CPA (100 mg/kg) on Day 0. 20 kDa- or 40 kDa-PEGylated G-CSF cysteine mutein was then injected subcutaneous into rats as a single dose of 100 μg/kg on Day 1. Protein samples were prepared in phosphate buffered saline. As a control one group of rats was injected with vehicle (phosphate buffered saline). There was one additional group of rats that received no chemotherapy. A blood sample was collected at pre-dose (Day 0) and on Days 1-10 and 12 from all groups to perform a complete blood cell count (CBC) analysis. 400 μl of whole EDTA blood was removed and placed in an eppendorf tube for submission to an external lab for CBC analysis. Results are shown in Tables 14 and 15. Both the 20 kDa- and 40 kDa-PEGylated G-CSF (C17S/A141C) cysteine mutein accelerated recovery of neutrophils and total white blood cells in neutropenic rats compared to CPA-only treated rats.

TABLE 12

Effects of a single dose of Neupogen or 20 kDa- or 40 kDa-PEG-GCSF (C17S/L3C) on white blood cell counts in neutropenic rats White Blood Cells (1000/μL)*

| Time (Day) | No CPA Control (Vehicle) | CPA-alone | G-CSF | 20 kDa-PEG-G-CSF (C17S/L3C) | 40 kDa-PEG-G-CSF (C17S/L3C) |
|---|---|---|---|---|---|
| 0 | 9.9 ± 0.5 | 9.4 ± 1.1 | 10.5 ± 0.5 | 10.6 ± 0.6 | 10.8 ± 0.8 |
| 1 | 11.3 ± 0.7 | 2.2 ± 0.3 | 3.0 ± 0.1 | 3.1 ± 0.2 | 2.8 ± 0.3 |
| 2 | 10.9 ± 0.7 | 1.9 ± 0.1 | 4.9 ± 0.3 | 5.9 ± 0.6 | 6.1 ± 0.7 |
| 3 | 10.1 ± 0.4 | 1.5 ± 0.2 | 1.6 ± 0.1 | 2.0 ± 0.1 | 1.8 ± 0.2 |
| 4 | 10.8 ± 1.1 | 1.0 ± 0.1 | 1.5 ± 0.1 | 2.7 ± 0.4 | 1.9 ± 0.2 |
| 5 | 12.0 ± 0.7 | 1.8 ± 0.3 | 2.2 ± 0.1 | 5.5 ± 0.4 | 6.5 ± 0.4 |
| 6 | 13.4 ± 0.8 | 3.3 ± 0.5 | 5.0 ± 0.4 | 6.8 ± 0.4 | 8.3 ± 0.5 |
| 7 | 11.9 ± 0.5 | 2.6 ± 0.3 | 3.5 ± 0.1 | 4.8 ± 0.4 | 4.9 ± 0.4 |
| 8 | 12.9 ± 0.7 | 3.9 ± 0.5 | 5.8 ± 0.3 | 6.1 ± 0.7 | 5.4 ± 1.0 |
| 9 | 13.8 ± 0.4 | 7.0 ± 1.0 | 8.7 ± 0.3 | 8.9 ± 1.1 | 9.3 ± 0.9 |
| 10 | 11.2 ± 0.4 | 6.1 ± 0.6 | 6.8 ± 0.2 | 6.2 ± 0.2 | 6.7 ± 0.5 |
| 12 | 10.5 ± 1.1 | 5.1 ± 0.5 | 5.1 ± 0.5 | 5.8 ± 0.3 | 5.1 ± 0.9 |

*WBC counts are means ± SE from 5 rats/group

TABLE 13

Effects of a single dose of Neupogen or 20 kDa- or 40 kDa-PEG-GCSF (C17S/L3C) on neutrophil counts in neutropenic rats
Absolute Neutrophil Counts (cells/μL)*

| Time (Day) | No CPA Control (Vehicle) | CPA-alone | G-CSF | 20 kDa-PEG-G-CSF (C17S/L3C) | 40 kDa-PEG-G-CSF (C17S/L3C) |
|---|---|---|---|---|---|
| 0 | 1144 ± 185 | 1134 ± 178 | 1166 ± 99 | 1139 ± 88 | 1148 ± 100 |
| 1 | 1442 ± 191 | 449 ± 70 | 783 ± 166 | 830 ± 205 | 758 ± 196 |
| 2 | 1760 ± 224 | 457 ± 40 | 2538 ± 260 | 3316 ± 474 | 3647 ± 547 |
| 3 | 1076 ± 127 | 350 ± 55 | 145 ± 32 | 488 ± 79 | 455 ± 51 |
| 4 | 1499 ± 238 | 105 ± 25 | 212 ± 38 | 917 ± 363 | 439 ± 77 |
| 5 | 1565 ± 116 | 236 ± 67 | 344 ± 54 | 2356 ± 308 | 3551 ± 395 |
| 6 | 1761 ± 195 | 473 ± 137 | 1255 ± 153 | 3106 ± 232 | 4476 ± 314 |
| 7 | 1792 ± 241 | 435 ± 66 | 891 ± 108 | 1635 ± 233 | 2207 ± 380 |
| 8 | 2214 ± 388 | 1054 ± 291 | 2345 ± 197 | 2276 ± 422 | 2358 ± 460 |
| 9 | 1995 ± 284 | 3057 ± 725 | 4169 ± 183 | 4010 ± 799 | 3723 ± 330 |
| 10 | 1571 ± 118 | 2520 ± 392 | 2761 ± 144 | 2242 ± 180 | 2820 ± 314 |
| 12 | 1833 ± 309 | 2109 ± 337 | 1648 ± 182 | 1845 ± 174 | 1886 ± 306 |

*Neutrophil counts are means ± SE for 5 rats/group

TABLE 14

Effects of a single dose of Neupogen or 20 kDa- or 40 kDa-PEG-GCSF (C17S/A141C) on white blood cell counts in neutropenic rats
White Blood Cells (1000/μL)*

| Time (Day) | No CPA Control (Vehicle) | CPA-alone | G-CSF | 20 kDa-PEG-G-CSF (C17S/A141C) | 40 kDa-PEG-G-CSF (C17S/A141C) |
|---|---|---|---|---|---|
| 0 | 12 ± 0.9 | 11.3 ± 0.8 | 12.9 ± 0.6 | 12.5 ± 0.6 | 12 ± 0.7 |
| 1 | 12.2 ± 2.1 | 4 ± 0.4 | 3.9 ± 0.3 | 3.7 ± 0.3 | 3.7 ± 0.5 |
| 2 | 13.9 ± 0.9 | 2.4 ± 0.3 | 6.2 ± 0.3 | 9 ± 0.4 | 7.3 ± 0.3 |
| 3 | 12 ± 0.5 | 1.7 ± 0.2 | 1.5 ± 0.1 | 3.3 ± 0.3 | 2.8 ± 0.1 |
| 4 | 9.4 ± 0.7 | 1.0 ± 0.1 | 1.0 ± 0.1 | 1.9 ± 0.3 | 1.4 ± 0.2 |
| 5 | 9.8 ± 1.2 | 1.1 ± 0.2 | 1.3 ± 0.2 | 3.7 ± 0.4 | 5.5 ± 0.8 |
| 6 | 12.6 ± 1.1 | 3 ± 0.6 | 4.8 ± 0.4 | 8.9 ± 1.9 | 9.5 ± 0.5 |
| 7 | 10.6 ± 0.7 | 2.8 ± 0.2 | 2.4 ± 0.4 | 6.5 ± 1.1 | 7 ± 0.8 |
| 8 | 12.5 ± 0.8 | 3.8 ± 0.2 | 4.3 ± 0.3 | 7.6 ± 1.1 | 6.7 ± 1.2 |
| 9 | 13.7 ± 0.6 | 6.6 ± 0.5 | 7.5 ± 0.4 | 10.4 ± 0.9 | 10 ± 1 |
| 10 | 12.1 ± 0.7 | 6.3 ± 0.5 | 6.6 ± 0.5 | 6.9 ± 0.9 | 6.4 ± 0.5 |
| 12 | 8.6 ± 1.2 | 4.7 ± 0.4 | 4.0 ± 0.4 | 6.0 ± 0.6 | 5.9 ± 0.7 |

*WBC counts are means ± SE from 5 rats/group

TABLE 15

Effects of a single dose of Neupogen or 20 kDa- or 40 kDa-PEG-GCSF (C17S/A141C) on neutrophil counts in neutropenic rats
Absolute Neutrophil Counts (cells/μL)*

| Time (Day) | No CPA Control (Vehicle) | CPA-alone | G-CSF | 20 kDa-PEG-G-CSF (C17SA141C) | 40 kDa-PEG-G-CSF (C17S/A141C) |
|---|---|---|---|---|---|
| 0 | 2406 ± 527 | 2312 ± 368 | 2306 ± 330 | 2251 ± 217 | 2254 ± 203 |
| 1 | 1987 ± 356 | 1007 ± 200 | 644 ± 62 | 687 ± 94 | 762 ± 289 |
| 2 | 2138 ± 304 | 642 ± 123 | 3606 ± 142 | 5977 ± 288 | 4675 ± 241 |
| 3 | 1992 ± 190 | 499 ± 89 | 243 ± 26 | 1312 ± 102 | 1027 ± 95 |
| 4 | 1181 ± 163 | 125 ± 9 | 137 ± 16 | 334 ± 93 | 265 ± 61 |
| 5 | 1310 ± 229 | 135 ± 27 | 187 ± 37 | 1302 ± 181 | 3006 ± 568 |
| 6 | 4188 ± 1679 | 540 ± 186 | 1239 ± 239 | 4621 ± 1369 | 5388 ± 507 |
| 7 | 1506 ± 80 | 409 ± 98 | 422 ± 88 | 3242 ± 915 | 3717 ± 523 |
| 8 | 1721 ± 147 | 794 ± 127 | 1158 ± 112 | 3827 ± 801 | 2668 ± 556 |
| 9 | 2505 ± 229 | 2962 ± 375 | 3618 ± 334 | 5712 ± 674 | 4225 ± 189 |
| 10 | 2135 ± 634 | 2745 ± 169 | 3228 ± 609 | 3262 ± 453 | 3242 ± 353 |
| 12 | 1391 ± 250 | 1533 ± 108 | 1281 ± 174 | 1842 ± 283 | 1937 ± 179 |

*Neutrophil counts are means ± SE for 5 rats/group

EXAMPLE 34

Use of Alpha Interferon Cysteine Muteins to Inhibit Growth of Human Cancer Cells IFN-α2 cysteine muteins and methods for expressing, purifying and PEGylating the proteins are described in Example 3 and in PCT/US00/00931 and PCT/US01/16088. The M111C mutein was expressed and refolded as described in PCT/US00/00931 and PCT/US01/16088. M111 is located in the C-D loop of alpha interferon-2. The protein was purified by a combination of S-Sepharose, copper chelating (immobized metal affinity chromatography) and Phenyl-Sepharose (hydrophobic interaction chromatography) column chromatography, methods for which are described in PCT/US00/00931 and PCT/US01/16088. The protein was modified with a 20 kDa-maleimide PEG (Shearwater Corporation) using dithiothreitol (DTT) as the reducing agent. The protein was partially reduced by incubation with a 25-fold molar excess of DTT for 20 minutes at room temperature. The solution was dialyzed against 20 mM MES, pH5. The PEGylation step was performed using a 10-fold molar excess of 20 kDa-maleimide PEG, 100 mM Tris, 0.5M EDTA, 2.6 micromolar IFN-α (M111C) at pH 7.5, at room temperature for 1 hour. The reaction was stopped by diluting the sample 1:4 with 20 mM MES, pH 5 and adjusting the pH to ≦4. PEGylated M111C protein was separated from unPEGylated protein by S-Sepharose chromatography. Similar methods were used to prepare the M111C protein modified with a 40 kDa-branched maleimide PEG (Shearwater Corporation).

A study was done to evaluate the potential of the PEGylated IFN-α2 (M111C) cysteine mutein to inhibit growth of human tumor cells in a tumor xenograft model. The human tumor cell line used was the ovarian carcinoma cell line NIH-OVCAR-3, which was obtained from the American Type Culture Collection (Rockville, Md.). Cells were grown in vitro in MEM media containing 10% fetal bovine serum, glutamine and penicillin. Female athymic nude (nu/nu) mice, 5 to 6 weeks of age and weighing approximately 23 grams at study initiation, were obtained from Charles River (Wilmington, Mass.). The NIH-OVCAR-3 cells were harvested by trypsinization, washed and resuspended at a concentration of $25 \times 10^6$ cells per ml in a 50:50 mixture of Phosphate Buffered Saline (PBS)/Matrigel. Matrigel was purchased from BD Biosciences (Bedford, Mass.). Animals (10-11 animals/group) were injected subcutaneously in the axillary area with 0.2 ml of the PBS/Matrigel mixture containing 5 millions cells on day 0. Subcutaneous dosing (0.2 ml/animal) of the test compounds began on day 1 and continued through day 69 using a 3 times per week dosing schedule (Monday, Wednesday, Friday). Mice were weighed on day 0, prior to the injection of cells, and on the days of tumor measurements. Animals were randomized according to body weight on day 0. Tumors were measured using calipers at 3-4 day intervals for 10 weeks post injection. Tumor volume was determined using a formula of ((Width×Width)×Length)/2). The length and width of the tumors were measured with a Fowler Ultra-Cal III caliper. These measurements were taken perpendicular to each other. The unit of measurement was in millimeters. This volume ($mm^3$) is considered a valid estimate of weight (in mg). Dosing of the test compounds began on day 1 and continued for 10 weeks. The dosing route was subcutaneous. The dose volume remained constant at 0.2 ml/animal. One group of 10 animals received vehicle solution (phosphate buffered saline containing 0.1 mg/ml of mouse albumin). A second group of 11 animals received 5 micrograms/injection/mouse of IFN-α2 (Roferon, Roche) in vehicle solution. A third group of 11 animals received 5 micrograms/injection/mouse of 20 kDa-PEG-IFN-α (M111C) in vehicle solution. Table 16 shows the mean tumor volumes for the test groups over time. All of the test groups showed an initial decline in tumor volume through about day 20, which appears to be due to absorption of the PBS/matrigel mixture. From about day 20 until the end of the study, tumors increased in volume in animals receiving the vehicle solution. Tumor volumes in animals receiving 20 kDa-PEG-IFN-α (M111C) were significantly smaller than tumor volumes in animals receiving vehicle solution at all times from about day 16 to day 70. Mean tumor weight at necropsy (day 70) also was significantly reduced in animals receiving 20 kDa-PEG-IFN-α (M111C) compared to animals receiving vehicle. The data demonstrate that 20 kDa-PEG-IFN-α (M111C) is very effective at inhibiting growth of human tumors in animals. Similar experiments can be performed testing lower or higher doses of the PEGylated cysteine mutein, different dosing regimens, e.g., once per week or once every other week, or different routs of administration, e.g., intravenous or intraperitoneal.

TABLE 16

20K-PEG IFN-α (M111C) Inhibits growth of human Tumor Xenografts in Nude Mice

| | Mean Tumor Volume ± SEM (cubic millimeters) | | |
|---|---|---|---|
| Day of study | Vehicle | WT IFN-α | 20K-PEG IFN-α (M111C) |
| 1 | 175.93 ± 11.98 | 208.21 ± 14.98 | 204.45 ± 10.85 |
| 2 | 186.58 ± 8.28 | 166.08 ± 12.55 | 159.38 ± 10.09 |
| 6 | 102.22 ± 6.61 | 87.99 ± 8.82 | 76.28 ± 4.70 |
| 9 | 74.36 ± 4.65 | 64.33 ± 7.59 | 56.73 ± 3.47 |
| 13 | 70.73 ± 4.81 | 59.81 ± 10.50 | 45.43 ± 3.89 |
| 16 | 74.98 ± 5.11 | 51.76 ± 4.33 | 36.13 ± 3.03 |
| 20 | 79.44 ± 3.34 | 50.52 ± 4.17 | 26.75 ± 4.25 |
| 23 | 85.55 ± 5.12 | 61.65 ± 5.78 | 36.29 ± 4.98 |
| 27 | 100.18 ± 4.52 | 64.93 ± 6.35 | 27.20 ± 3.98 |
| 30 | 110.05 ± 6.58 | 56.17 ± 5.20 | 23.48 ± 4.15 |
| 34 | 115.81 ± 9.30 | 48.56 ± 5.19 | 18.46 ± 5.40 |
| 37 | 142.18 ± 11.26 | 47.71 ± 5.40 | 15.29 ± 3.60 |
| 41 | 190.06 ± 16.06 | 80.82 ± 11.29 | 24.09 ± 5.95 |
| 44 | 211.06 ± 16.94 | 99.86 ± 12.74 | 26.01 ± 7.62 |
| 48 | 252.63 ± 25.13 | 110.22 ± 12.33 | 47.14 ± 10.56 |
| 51 | 288.32 ± 41.95 | 138.89 ± 15.74 | 36.49 ± 7.53 |
| 55 | 388.16 ± 54.09 | 154.49 ± 18.20 | 39.92 ± 8.14 |
| 58 | 392.12 ± 65.46 | 162.00 ± 18.64 | 34.73 ± 9.26 |
| 62 | 438.91 ± 93.31 | 192.96 ± 25.85 | 28.89 ± 8.80 |
| 65 | 442.13 ± 85.65 | 212.40 ± 30.03 | 23.30 ± 8.36 |
| 70 | 561.30 ± 138.49 | 200.51 ± 24.87 | 12.69 ± 6.65 |

All of the documents cited herein are incorporated herein by reference.

The protein analogues disclosed herein can be used for the known therapeutic uses of the native proteins in essentially the same forms and doses all well known in the art.

While the exemplary preferred embodiments of the present invention are described herein with particularity, those having ordinary skill in the art will recognize changes, modifications, additions, and applications other than those specifically described herein, and may adapt the preferred embodiments and methods without departing from the spirit of this invention.

REFERENCES

Abdel-Meguid, S. S., Shieh, h.-S., Smith W. W., Dayringer, H. E., Violand, B. N. and Bentle, L. A. (1987) Proc. Natl. Acad. Sci. USA 84: 6434-6437.

Abuchowski, A., Kazo, G. M., Verhoest, C. R., van Es, T., Kafkewitz, D., Nucci, M. L., Viau, A. T. and Davis, F. F. (1984) Cancer Biochem. Biophys. 7: 175-186.

Aggarwal, B. B. (1998) Human Cytokines. Handbook for Basic and Clinical Research. Volume III. Blackwell Science, Malden, Mass.

Aggarwal, B. B. and Gutterman, J. U. (1992) Human Cytokines. Handbook for Basic and Clinical Research. Volume I. Blackwell Scientific Publications, Cambridge, Mass.

Aggarwal, B. B. and Gutterman, J. U. (1996) Human Cytokines. Handbook for Basic and Clinical Research. Volume II. Blackwell Science, Cambridge, Mass.

Anderson, D. M., Johnson, L., Glaccum, M. B., Copeland, N. G., Gilbert, D. J., Jenkins, N. A., Valentine, V., Kirstein, M. N., Shapiro, D. N., Morris, S. W., Grabstein, K. and cosman, D. (1995) Genomics 25: 701-706.

Armitage, J. O. (1998) Blood 92: 4491-4508.

Balkwill, F. R. (1986) Methods Enzymology 119: 649-657.

Bartley, T. D., Bogenberger, J. et al., (1994) Cell 77: 1117-1124.

Bazan, F. (1991) Immunology Today 11: 350-354.

Bazan, J. F. (1992) Science 257: 410-411.

Becker, G. W. and Hsiung, H. M. (1986) FEBS Letters 204: 145-150.

Bill, R. M., Winter, P. C., McHale, C. M., Hodges, V. M., Elder, G. E., Caley, J., Flitsch, S. L., Bicknell, R. Lappin, T. R. J. (1995) Biochem. Biophys. Acta 1261: 35-43.

Bischof, R. J., Zafiropoulos, D., Hamilton, J. A. and Campbell, I. K. (2000) Clin. Exp. Immunology 119: 361-367.

Bittorf, T., Jaster, R., Brock, J. (1993) FEBS Letters 336: 133-136.

Blatt, L. M., Davis, J. M., Klein, S. B. and Taylor, M. W. (1996) Journal of Interferon and cytokine Research 16: 489-499.

Blumberg, H., Conklin, D., Xu, W., Grossmann A. et al. (2001) Cell 104: 9-19.

Boissel, J.-P., Lee, W.-R., Presnell, S. R., Cohen, F. E. and Bunn, H. F. (1993) J. Biol. Chem. 268: 15983-15993.

Butler, C. A. (1996) Lehman Brothers Technical Report "A Paradigm for Success".

Campbell, I. K., Bendele, A., smith, D. A. and Hamilton, J. A. (1997) Annals of the Rheumatic Diseases 56: 364-368.

Campbell, I. K., Rich, M. J., Bischof, R. J., Dunn, A. R., Grail, D. and Hamilton, J. A. (1998) The Journal of Immunology 161: 3639-3644.

Cantrell, M. A., Anderson, D., Cerretti, D. P., Price, V., McKereghan, K., Tushinski, R. J., Mochizuki, D. Y., Larsen, A., Grabstein, K., Gillis, S. and Cosman, D. Proc. Natl. Acad. Sci. USA 82: 6250-6254.

Canturk, N. Z., Vural, B., Esen, N., Canturk, Z., Oktay, G., Kirkali, G. and Solakoglu, S. (1999) Endocr Res. 25: 105-116.

Cebon, J. S. and Lieschke, G. J. (1994) Oncology 51: 177-188.

Cerretti, D. P. et al. (1988) Molecular Immunology 25: 761.

Chang, C. N., Rey, B., Bochner, B., Heyneker, H. and Gray, G. (1987) Gene: 189-196.

Chen, T. J., Kuo, C. B., Tsai, K. F., Liu, J. W., Chen, D. Y. and Walker, A. M. (1998) Endocrinology 139: 609-616.

Cook, A. D., Braine, E. L., campbell, I. K., Rich, M. J. and Hamilton, A. J. (2001) Arthritis Res. 3: 293-298.

Cotes, P. M. and Bangham, D. R. (1961) Nature 191: 1065-1067

Cox, G. N., McDermott, M. J., Merkel, E., Stroh, C. A., Ko, S. C., Squires, D. H., Gleason, T. M. and Russell, D. (1994) Endocrinology 135: 1913-1920.

Cunningham, B. C. and Wells, J. A. (1989) Science 244: 1081-1085.

Cunningham, B. C., Jhurani, P., Ng, P. and Wells, J. A. (1989) Science 243: 1330-1336.

Cunningham, B. C., Ultsch, M., de Vos, A. M., Mulkerrin, M. G., Clauser, K. R. and Wells, J. A. (1991) Science 254: 821-825.

D'Andrea, A. D., Lodish, H. F. and Wong, G. G. (1989) Cell 57: 277-285.

Davis, S., Aldrich, T. H., Stahl, N., Pan, L., Taga, T., Kishimoto, T., Ip, N. Y. and Yancopoulus, G. D. (1993) Science 260: 1805-1808.

DeChiara, T. M., Erlitz, F. and Tarnowski,k, S. J. (1986) Methods Enzymology, 119: 403-15.

de la Llosa, P., Chene, N. and Martal, J. (1985) FEBS Letts. 191: 211-215

Delorme, E., Lorenzini, T., Giffin, J., Martin, F., Jacobsen, F., Boone, T., Elliot, S. (1992) Biochemistry 31: 9871-9876.

de Sauvage, F. J., Hass, P. E., Spencer, S. D. et al. (1994) Nature 369: 533-538.

de Vos, A. M., Ultsch, M. and Kossiakoff, A. A. (1992) Science 255: 306-312.

Devos, R., Plaetinck, G., Cheroutre, H., Simons, G., Degrave, W., Tavernier, J., Remaut, E. and Fiers, W. (1983) Nucleic Acids Research 11: 4307.

Diederichs, K., Boone, T. and Karplus, A. (1991) Science 154: 1779-1782.

Dorssers, L., Burger, H., Bot, F., Delwel, R., Van Kessel, A. H. M. G., Lowenberg, B. and Wagemaker, G. (1987) 55: 115-124.

Dube, S., Fisher, J. W., Powell, J. S. (1988) J. Biol. Chem. 263: 17526-17521.

Fish, E. N., Banerjee, K., Levine, H. L. and Stebbing, N. (1986) Antimicrob. Agents Chemother. 30: 52-56.

Foster, D. C., Sprecher, C. A., Grant, F. J., Kramer, J. M. et al. (1994) Proc. Natl. Acad. Sci USA 91: 13023-13027.

Fukuda, M. N., Sasaki, H., Fukuda, M. (1989) Blood 73: 84-89.

Gaudernack, G. and Gjertsen, M. K. (1999) Eur. J. Cancer 35 (Supplement 3): S33-35.

Goeddel, D. V., Heyneker, H. L., Hozumi, T. et al., (1979) Nature 281: 544-548.

Goeddel, D. V., Yelverton, E., Ullrich, A., Heynecker, H. L., Miozzari, G., Holmes, W., Seeburg, P. H., Dull, T., Mat, L., Stebbing, N., Crea, R., Maeda, S., McCandliss, R., Sloma, A., Tabor, J. M., Gross, M., Familletti, P. C. and Pestka, S. (1980) Nature 287: 411-416.

Goldwasser, E. and Gross, M. (1975) Methods Enzymology 37: 109-121.

Goodson, R. J. and Katre, N. V. (1990) Biotechnology 8: 343-346.

Goodwin, R. G., Lupton, S., Schmierer, A., Hjerrild, K. J., Jerzy, R., Clevenger, W., Gillis, S., Cosman, D. and Namen, A. E. (1989) Proc. Natl. Acad. Sci. USA 86: 302-306.

Gough, N. M. et al., (1988) Proc. Natl. Acad. Sci USA 85: 2623-2627.

Gubler, U., Chua, A. O., Schoenhaut, D. S., Dwyer, C. M., McComas, W., Motyka, R., Nabavi, N., Wolitzky, A. G., Quinn, P. M., Familletti, P. C. and Gately, M. K. (1991) Proc. Natl Acad. Sci. USA 88: 4143-4147.

Hershfield, M. S., Buckley, R. H., Greenberg, M. L. et al., (1987) N. Engl. J. Medicine 316: 589-596.

Hill, C. P., Osslund, T. D. and Eisenberg, D. (1993) Proc. Natl. Acad. Sci. USA 90:5167-5171.

Hoeller, C., Jansen, B., Heere-Ress, E., Pustelnik, T., Mossbacher, U., Schlagbauer-Wadl, H., Wolff, K and Pehamberger, H. (2001) J. Invest. Dermatol. 117: 371-374.

Hoffman, R. C., Andersen, H., Walker, K., Krakover, J. D., Patel, S., Stamm, M. R. and Osborn, S. G. (1996) Biochemistry 35: 14849-14861.

Hsiung, H. M., Mayne, N. G. and Becker, G. W. (1986) Biotechnology 4: 991-995.

Hercus, T. R., Bagley, C. J., Cambareri, B., Dottore, M., Woodcock, J. M., Vadas, M. A., Shannon, M. F., and Lopez, A. F. (1994) Proc. Natl. Acad. Sci. USA 91: 5838-5842.

Hirano, T., Yasukawa, K., Harada, H., Taga, T., Watanabe, Y., Matsuda, T., Kashiwamura, S.-I., Nakajima, K., Koyama, K., Iwamatsu, A., Tsunasawa, S., Sakiyama, F., Matsui, H., Takahara, Y., Taniguchi, T. and Kishimoto, T. (1986) Nature 324: 73-76.

Horisberger, M. A. and Di Marco, S. (1995) Pharmac. Ther. 66: 507-534.

Innis, M. A., Gelfand, D. H., Sninsky, J. J. and White, T. J. (1990) PCR Protocols: A Guide to Methods and Applications. Academic Press, San Diego, Calif.

Jacobs, K., Shoemaker, C., Rudersdorf, R. et al., (1985) Nature 313: 806-810.

Jones, T. C. (1999) Eur. J. Cancer 35 (Supplement 3): S8-10.

Joseph, G., Neustadt, D. H., Hamm, J., Kellihan, M. and Hadley, T. (1991) American Journal of Hematology 37: 55-56.

Jyung, R. W., Wu, L., Pierce, G. L. and Mustoe, T. A. (1994) Surgery 115: 325-334.

Kaczmarski, R. S., Pozniak, A., Lakhani, A., Harvey, E. and mufti, G. J. (1993) British Journal of Haematology (1993) 84: 338-340.

Karpusas, M., Nolte, M., Benton, C. B., Meier, W., Lipscomb, W. N. and Goelz, S. (1997) Proc. Natl. Acad. Sci. USA 94: 11813-11818.

Katre, N. V. (1990) J. Immunology 144: 209-213.

Katre, N. V., Knauf, M. J. and Laird, W. J. (1987) Proc. Natl. Acad. Sci. USA 84: 1487-1491.

Kawasaki, E. S. et al., (1985) Science 230: 291.

Kawashima, I., Ohsumi, J., Mita-Honjo, K., Shimoda-Takano, Ishikawa, H., Sakakibara, S., Miyadai, K. and Takiguchi, Y. (1991) FEBS Letts. 283: 199-202.

Kingsley, D. M. (1994) Genes Dev. 8: 133-146.

Komatsu, N., Nakauchi, H., Miwa, A., Ishihara, T., Eguguchi, M. et al., (1991) Cancer Research 51, 341-348.

Kruse, N., Tony, H.-P. and Sebald, W. (1992) EMBO J. 11: 3237-3244.

Lam, A., Fuller, F., Miller, J., Kloss, J., Manthorpe, M., Varon, S. and Cordell, B. (1991) Gene 102: 271-276.

Kubota, N., Orita, T., Hattori, K., Oh-eda, M., Ochi, N. and Yamazaki, T. (1990) J. Biochem. 107: 486-492.

Kuga, T., Komatsu, Y., Yamasaki, M., De4kine, S., Miyaji, H., Nishi, T., Sato, M., Yokoo, Y., Asano, M., Okabe, M., Morimoto, M. and Itoh, S. (1989) Bioch. Biophys. Res. Comm. 159: 103-111.

Kunkel, T. A., Roberts, J. D. and Zakour, R. A. (1987) Methods in Enzymology 154: 367-382.

Lange, B., Valtieri, M., Santoli, D., Caracciolo, D., Mavilio, F., Gemperlein, I., Griffin, C., Emanuel, B., Finan, J., Nowell, P. and Rovera, G. (1987) Blood 70: 192-199.

Lee, F., Yokota, T., Otsuka, T., Gemmell, L., Larson, N., Luh, J., Arai, K.-I. and Rennick, D. (1985) Proc. Natl. Acad. Sci. USA 82: 4360-4364.

Lewis, J. A. (1995) Chapter 9: Antiviral activity of cytokines. pp. 129-141.

Li, C. H. (1982) Mol. Cell. Biochem. 46: 31-41.

Lin, F.-K. (1996) U.S. Pat. No. 5,547,933.

Lin, F.-K., Suggs, S., Lin, C.-H., et al., Proc. Natl. Acad. Sci. USA (1985) 82: 7580-7584.

Linsley, P. S., Kallestad, J., Ochs, V. and Neubauer, M. (1990) 10: 1882-1890.

Livnah, O., Stura, E. A., Johnson, D. L. et al., (1996) Science 273: 464-471.

Lu, H. S., Clogston, C. L., Narhi, L. O., Merewether, L. A., Pearl, W. R. and Boone, T. C. (1992) J. Biol. Chem. 267: 8770-8777.

Lydon, N. B., Favre, C., Bore, S., Neyret, O., Benureau, S., Levine, A. M., Seelig, G. F., Nagabhushan, T. L. and Trotta, P. P. (1985) Biochemistry 24: 4131-41.

MacGillivray, M. H., Baptista, J. and Johnson, A. (1996) J. Clin. Endocrinol. Metab. 81: 1806-1809.

McQualter, J. L., Darwiche, R., Ewing, C., Onuki, M., Kay, T. W., Hamilton, J. A., Reid, H. H., and Bernard, C. C. A. (2001) J. Exp. Med. 194: 873-881.

Malik, N., Kallestad, J. C., Gunderson, N. L., Austin, S. D., Neubauer, M. G., Ochs, V., Marquardt, H., Zarling, J. M., Shoyab, M., Wei, C.-M., Linsley, P. S. and Rose, T. M. (1989) Molecular and Cellular Biology 9: 2847-2853.

Martial, J., Chene, N. and de la Llosa, P. (1985) FEBS. Letts. 180: 295-299.

Martial, J. A., Hallewell, R. A., Baxter, J. D. and Goodman, H. M. (1979) Science 205: 602-606.

Matthews, D. J., Topping, R. S., Cass, R. T. and Giebel, L. B. (1996) Proc. Natl. Acad. Sci. USA 93: 9471-9476.

McKay, D. B. (1992) Science 257: 412.

McKenzie, A. N. J., Culpepper, J. A., Malefyt, R. de W., Briere, F., Punnonen, J., Aversa, G., Sato, A., Dang, W., Cocks, B. G., Menon, S., de Vries, J. E., Banchereau, J., and Zurawski, G. (1993) Proc. Natl. Acad. Sci. USA 90: 3735-3739.

Meyers, F. J., Paradise, C., Scudder, S. A., Goodman, G. and Konrad, M. (1991) Clin. Pharmacol. Ther. 49: 307-313.

Milburn, M. V., Hassell, A. M., Lambert, M. H., Jordan, S. R., Proudfoot, A. E., Graber, P. and Wells, T. N. C. (1993) Nature 363: 172-176.

Mills, J. B., Kostyo, J. L., Reagan, C. R., Wagner, S. A., Moseley, M. H. and Wilhelm, A. E. (1980) Endocrinology 107: 391-399.

Minty, A., Chalon, P., Derocq, J.-M., Dumont, X., Guilemot, J.-C., Kaghad, M., Labit, C., Leplatois, P., Liauzun, P., Miloux, B., Minty, C., Casellas, P., Loison. G., Lupker, J., Shire, D., Ferrara, P. and Caput, D. (1993) Nature 362: 248-250.

Moreau, J.-F., Donaldson, D. D., Bennett, F., Witek-Giannotti, J., Clark, S. C. and Wong, G. G. (1988) Nature 336: 690-692.

Mott, H. R. and Campbell, I. D. (1995) Current Opinion in Structural Biology 5: 114-121.

Martial, J. A., Hallewell, R. A., Baxter, J. D. and Goodman, H. M. (1979) Science 205: 602-606.

Nagata, S. (1994) in Cytokines and Their Receptors, N. A. Nicola ed., Oxford University Press, Oxford, pp. 158-160.

Nagata, S., Tsuchiya, M., Asano, S., Kziro, Y., Yamazaki, T., Yamamoto, O., Hirata, Y., Kubota, N., Oh-eda, M., Nomura, H. and Ono, M. (1986a) Nature 319: 415-418.

Nagata, S., Tsuchiya, M., Asano, S., Yamamoto, O., Hirata, Y., Kubota, N., Oh-eda, M., Nomura, H. and Yamazaki, T. (1986b) EMBO J. 5: 575-581.

O'Reilly, D. R., Miller, L. K., Luckow, V. A. (1992) Caculovirus Expression Vectors, W.H. Freeman Co. publishers, New York.

Otsuka, T., Miyajima, A., Brown, N., Otsu, K., Abrams, J., Saeland, S., Caux, C., De Waal-Malefyt, De Vries, J., Meyerson, P., Yokota, K., Gemmell, Rennick, D., Lee, F., Arai, N., Arai, K.-I. and Yokota, T. (1988) J. Immunology 140: 2288-2295.

Owers-Narhi, L., Arakawa, T., Aoki, K. H., Elmore, R., Rohde, M. F., Boone, T., Strickland, T. W. (1991) J. Biol. Chem. 266: 23022-23026.

Ozes, O. S., Reiter, Z., Klein, S., Blatt, L. M. and Taylor, M. W. (1992) J. Interferon Research 12: 55-59.

Paonessa, G., Graziani, R., de Serio, A., Savino, R., Ciapponi, L., Lahm, A., Ssalvati, A. L., Toniatti, C. and Ciliberto, G. (1995) EMBO J. 14: 1942-1951.

Park, L. S., Waldron, P. E., Friend, D., Sassenfeld, H. M., Price, V., Anderson, D., Cosman, D., Andrews, R. G., Bernstein, I. D. and Urdal, D. L. (1989) Blood 74: 56-65.

Paul, S. R., Bennett, F., Calvetti, J. A., Kelleher, K., Wood, C. R., O'Hara, R. M., Leary, A. C., Sibley, B., Clark, S. C., William, D. A. and Yang, Y.-C. (1990) Proc. Natl. Acad. Sci. USA 87: 7512-7516.

Pestka, S., Langer, J. A., Zoon, K. C. and Samuel, C. E. (1987) Ann. Rev. Biochem. 56: 727-777.

Pickering, L. A., Kronenberg, L. H. and Stewart, W. E., II (1980) Proc. Natl. Acad. Scio. USA 77: 5938-5942.

Powers, R., Garrett, D. S., March, C. J., Frieden, E. A., Gronenborn, A. M. and Clore, G. M. (1992) Science 256: 1673-1677.

Radhakrishnan, R., Walter, L. J., Hruka, A., Reichert, P., Trotta, P. P., Nagabhushan, T. L. and Walter, M. R. (1996) Structure 4: 1453-1463.

Read, L. C., Tomas, F. M., Howarth, G. S., Martin, A. A., Edson, K. J., Gillespie, C. M., Owens, P. C. and Ballard, F. J. (1992) J. Endocrinology 133: 421-431.

Redfield, C., Smith L. J., Boyd, J., Lawrence, G. M. P., Edwards, R. G., Smith, R. A. G., and Dobson, C. M. (1991) Biochemistry 30: 11029-11035.

Robinson, R. C., Grey, L. M., Stauton, D., Vankelecom, H., Vernallis, A. B., Moreau, J.-F., Rucker, R., Bresler, H. S., Heffelfinger, M., Kim, J. A., Martin, E. W. and Triozzi, P. L. (1999) Journal of Immunotherapy 22: 80-84.

Stuart, D. I., Heath, J. K. and Jones, E. Y. (1994) Cell 77: 1101-1116.

Sasaki, H., Bothner, B., Dell, A. and Fukuda, M. (1987) J. Biol. Chem. 262: 12059-12076.

Sasaki, H. Ochi, N., Dell, A. and Fukuda, M. (1988) Biochemistry 27: 8616-8626.

Shaw, G., Veldman, G. and Wooters, J. L. (1992) U.S. Pat. No. 5,166,322.

Shirafuji, N., Asano, S., Matsuda, S., Watari, K., Takaku, F. and Nagata, S. (1989) Exp Hematol. 17: 116-119.

Silvennoinen, O. and Ihle, J. N. (1996) Signaling by the Hematopoietic Cytokine Receptors, R.G. Landes, Company, Austin, Tex.

Small, E. J., Reese, D. M., Um, B., Whisenant, S., Dixon, S. C. and Figg, W. D. (1999) Clin. Cancer Res. 5: 1738-1744.

Souza, L. M., Boone, T. C., Gabrilove, J., Lai, P. H., Zsebo, K. M., Murdock, D. C., Chazin, V. R., Bruszewski, J., Lu, H., Chen, K. K., Barendt, J., Platzer, E., Moore, M. A. S., Mertelsmann, R. and Welte, K. (1986) Science 232: 61-65.

Spitler, L. E., Grossbard, M. L., Ernstoff, M. S., Silver, G., Jacobs, M., Hayes, F. A. and Soong, S. J. (2000) 18: 1603-1605.

Spivak, J. L., Hogans, B. B. (1989) Blood 73: 90-99.

Takeuchi, M., Takasaki, S., Miyazaki, H., Takashi, D., Hoshi, S., Kochibe, N. and Kotaba, A. (1988) J. Biol. Chem. 263: 3657-3663.

Tanaka, H., Satake-Ishikawa, R., Ishikawa, M., Matsuki, S. and Asano, K. (1991) Cancer Research 51: 3710-3714.

Taniguchi, T., Matsui, H., Fujita, T., Takaoka, C., Kashima, N., Yoshimoto, R. and Hamuro, J. (1983) Nature 302: 305-310.

Taniguchi, T., Ohno, S., Fujii-Kuriyama, Y. and Muramatsu, M. (1980) Gene 10: 11-15.

Tarnowski, S. J., Roy, S. K., Liptak, R. A., Lee, D. K. and Ning, R. Y. (1986) Methods Enzymology 119:153-165.

Tavernier, J., Tuypens, T., Verhee, A., Plaetinck, G., Devos, R., Van Der Heyden, J., Guisez, Y. and Oefner, C. (1995) Proc. Natl. Acad. Sci. USA 92: 5194-5198.

Teh, L.-C. and Chapman, G. E. (1988) Biochem. Biophys. Res. Comm. 150: 391-398.

Thatcher, D. R. and Panayotatos, N. (1986) Methods Enzymology 119: 166-177.

Tomas, F. M., Knowles, S. E., Owens, P. C., Chandler, C. S., Francis, G. L., Read, L. C. and Ballard, F. J. (1992) Biochem. J. 282: 91-97.

Tsuchiya, M., Asano, S., Kaziro, Y and Nagata, S. (1986) Proc. Natl. Acad. Sci. USA 83: 7633-7637.

Tsuda, E., Kawanishi, G., Ueda, M., Masuda, S. and Sasaki, R. (1990) Eur. J. Biochem. 188: 405-411.

Vaughan, m. M., Moore, J., Riches, P. G., Johnston, S. R., A'Hern, R. P., Hill, M. E., Eisen, T., Ayliffe, M. J., Thomas, J. M. and Gore, M. E. (2000) Ann. Oncol. 11: 1183-1189.

Vieira, P., de Waal-Malefyt, R., Dang, M. N., Johnson, K. E., Kastelein, R., Fiorentino, D. F., de Vries, J. E., Roncarolo, M.-G., Mosmann, T. R. and Moore, K. W. (1991) Proc. Natl. Acad. Sci. USA 88: 1172-1176.

Wang, A., Lu, S.-D., and Mark, D. F. (1984) Science 224: 1431-1433.

Walter, M. R., Cook, W. J., Ealick, S. E., Nagabhusan, T. L., Trotta, P. T. and Bugg, C. E. (1992) J. Mol. Biol. 224: 1075-1085.

Warren, T. L. and Weiner, G. J. (2000) Curr. Opin. Hematology 7: 168-173.

Wen, D., Boissel, J.-P. R., Tracy, T. E., Gruninger, R. H., Mulcahy, L. S., Czelusniak, J., Goodman, M. and Bunn, H. F. (1993) Blood: 1507-1516.

Wen, D., Boissel, J. P., Showers, M., Ruch, B. C. and Bunn, H. F. (1994) J. Biol. Chem. 269: 22839-22846.

White, B. A., (1993), Methods in Molecular Biology, volume 15: PCR Protocols: Current Methods and Applications. Humana Press, Totowa, N.J.

Wojchowski, D. M., Orkin, S. H., Sytkowshi, A. J. (1987) Biochim. Biophys. Acta 910: 224-232.

Wolf, S. F., Temple, P. A., Kobayashi, M., Young, D., Dicig, M., Lowe, L., Dzialo, R., Fitz, L., Ferenz, C., Hewick, R. M., Kelleher, K., Herrmann, S. H., Clark, S. C., Azzoni, L., Chan, S. H., Trinchieri, G. and Perussia, B. (1991) J. Immunology 146: 3074-3081.

Wong, G. G. et al., (1987) Science 235: 1504.

Wrighton, N. C., Farrell, F. X., Chang, R. et al., (1996) Science 273: 458-463.

Yamaguchi, K., Akai, K., Kawanishi, G. Ueda, M., Masuda, S., Sasaki, R. (1991). J. Biol. Chem. 266: 20434-20439.

Yang, H. Y. and Hamilton, J. A. (2001) Arthritis and Rheumatism 44: 111-119.

Yang, Y.-C., Ciarletta, A. B., Temple, P. A., Chung, M. P., Kovacic, S., Witek-Giannotti, J. S., Leary, A. C., Kriz, R., Donahue, R. E., Wong, G. G. and Clark, S. C. (1986) Cell 47: 3-10.

Yang, Y.-C., Ricciadi, S., Ciarletta, A., Calvetti, J., Kelleher, K. and Clark, S. C. (1989) Blood 74: 1880-1884.

Yokota, T., Otsuka, T., Mosmann, T., Banchereau, J., DeFrance, T., Blanchard, D., De Vries, J. E., Lee F. and Arai, K.-I. (1986) Proc. Natl. Acad. Sci. USA 83: 5894-5898.

Yokota, T., Coffman, R. L., Hagiwara, H., Rennick, D. M., Takebe, Y., Yokota, K., Gemmell, L., Shrader, B., Yang, G., Meyerson, P., Luh, J., Hoy, P., Pene, J., Briere, F., Spits, H., Banchereau, J., DeVries, J., Lee, F., Arai, N. and Arai, K.-I. (1987) Proc. Natl. Acad. Sci. USA 84: 7388-7392.

Zurawski, S. M., Imler, J. L., and Zurawski, G. (1990) EMBO J. 9: 3899-3905.

Zurawski, S. M. and Zurawski, G. (1992) EMBO J. 11: 3905-3910.

---

What is claimed is:

1. A method to protect an animal from a disease or condition that can be treated by granulocyte colony-stimulating factor (G-CSF), comprising administering to an animal having said disease or condition a composition comprising a cysteine variant of G-CSF of SEQ ID NO: 6, wherein said G-CSF cysteine variant comprises a cysteine residue substituted for one amino acid selected from the group consisting of P2, S7, W58, A68, E93, A129, Q131, T133, Q134, A136, A139, and A141 or wherein a cysteine residue is added preceding the first amino acid of the mature protein or following the last amino acid of the mature protein, and wherein said variant has biological activity in vitro as measured by proliferation of a cell line that proliferates in response to granulocyte colony-stimulating factor.

2. The method of claim 1, wherein said cysteine variant comprises a cysteine residue substituted for A141.

3. The method of claim 1, wherein said cysteine variant comprises a non-cysteine amino acid substituted for C17.

4. The method of claim 1, wherein said cysteine variant comprises a cysteine residue substituted for A141 and a non-cysteine amino acid substituted for C17.

5. The method of claim 1, wherein said cysteine variant is modified with a cysteine-reactive moiety.

6. The method of claim 1, wherein said cysteine variant is modified with a cysteine-reactive moiety and wherein said cysteine variant comprises a non-cysteine amino acid substituted for C17.

7. The method of claim 5, wherein said cysteine-reactive moiety is a polyethylene glycol.

8. The method of claim 6, wherein said cysteine-reactive moiety is a polyethylene glycol.

9. The method of claim 1, wherein said composition is administered by a route selected from the group consisting of intravenous administration, intraperitoneal administration, intramuscular administration, intranodal administration, intracoronary administration, intraarterial administration, subcutaneous administration, transdermal delivery, intratracheal administration, intraarticular administration, intraventricular administration, inhalation, intranasal, intracranial, intraspinal, intraocular, aural, intranasal, oral, pulmonary administration, impregnation of a catheter, and direct injection into a tissue.

10. The method of claim 1, wherein said composition is administered by intravenous administration.

11. The method of claim 1, wherein said composition is administered by subcutaneous administration.

12. The method of claim 1, wherein said disease is neutropenia.

13. The method of claim 12, wherein said neutropenia is selected from the group consisting of: (a) neutropenia resulting from chemotherapy; (b) neutropenia associated with bone marrow transplantation; (c) neutropenia associated with infection with the human immunodeficiency virus; (d) neutropenia associated with burns, surgery, dilatation, anemia and neonatal septicemia; (e) severe chronic neutropenia; and (f) neutropenia associated with aplastic anemia and acute leukemia.

14. The method of claim 12, wherein said neutropenia is neutropenia resulting from chemotherapy.

15. The method of claim 1, wherein said cysteine variant comprises a cysteine residue substituted for P2.

16. The method of claim 1, wherein said cysteine variant comprises a cysteine residue substituted for S7.

17. The method of claim 1, wherein said cysteine variant comprises a cysteine residue substituted for W58.

18. The method of claim 1, wherein said cysteine variant comprises a cysteine residue substituted for A68.

19. The method of claim 1, wherein said cysteine variant comprises a cysteine residue substituted for E93.

20. The method of claim 1, wherein said cysteine variant comprises a cysteine residue substituted for A129.

21. The method of claim 1, wherein said cysteine variant comprises a cysteine residue substituted for Q131.

22. The method of claim 1, wherein said cysteine variant comprises a cysteine residue substituted for T133.

23. The method of claim 1, wherein said cysteine variant comprises a cysteine residue substituted for Q134.

24. The method of claim 1, wherein said cysteine variant comprises a cysteine residue substituted for A136.

25. The method of claim 1, wherein said cysteine variant comprises a cysteine residue substituted for A139.

26. The method of claim 1, wherein said cysteine variant comprises a cysteine residue added preceding the first amino acid of the mature protein.

27. The method of claim 1, wherein said cysteine variant comprises a cysteine residue added following the last amino acid of the mature protein.

28. The method of claim 1 wherein the cysteine variant comprises a cysteine residue substituted for P2 and a second cysteine substituted for A141.

* * * * *

SEQUENCE LISTING

<160> NUMBER OF SEQ ID NOS: 41

<210> SEQ ID NO 1
<211> LENGTH: 191
<212> TYPE: PRT
<213> ORGANISM: Homo sapiens

<400> SEQUENCE: 1

```
Phe Pro Thr Ile Pro Leu Ser Arg Leu Phe Asp Asn Ala Met Leu Arg
 1               5                  10                  15

Ala His Arg Leu His Gln Leu Ala Phe Asp Thr Tyr Gln Glu Phe Glu
             20                  25                  30

Glu Ala Tyr Ile Pro Lys Glu Gln Lys Tyr Ser Phe Leu Gln Asn Pro
         35                  40                  45

Gln Thr Ser Leu Cys Phe Ser Glu Ser Ile Pro Thr Pro Ser Asn Arg
     50                  55                  60

Glu Glu Thr Gln Gln Lys Ser Asn Leu Glu Leu Leu Arg Ile Ser Leu
 65                  70                  75                  80

Leu Leu Ile Gln Ser Trp Leu Glu Pro Val Gln Phe Leu Arg Ser Val
                 85                  90                  95

Phe Ala Asn Ser Leu Val Tyr Gly Ala Ser Asp Ser Asn Val Tyr Asp
             100                 105                 110

Leu Leu Lys Asp Leu Glu Glu Gly Ile Gln Thr Leu Met Gly Arg Leu
         115                 120                 125

Glu Asp Gly Ser Pro Arg Thr Gly Gln Ile Phe Lys Gln Thr Tyr Ser
     130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                 165                 170                 175

Leu Arg Ile Val Gln Cys Arg Ser Val Glu Gly Ser Cys Gly Phe
             180                 185                 190
```

<210> SEQ ID NO 2
<211> LENGTH: 166
<212> TYPE: PRT
<213> ORGANISM: Homo sapiens

<400> SEQUENCE: 2

```
Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
             20                  25                  30

Cys Ser Leu Asn Glu Asn Ile Thr Val Pro Asp Thr Lys Val Asn Phe
         35                  40                  45

Tyr Ala Trp Lys Arg Met Glu Val Gly Gln Gln Ala Val Glu Val Trp
     50                  55                  60

Gln Gly Leu Ala Leu Leu Ser Glu Ala Val Leu Arg Gly Gln Ala Leu
 65                  70                  75                  80
```

-continued

```
Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165
```

<210> SEQ ID NO 3
<211> LENGTH: 165
<212> TYPE: PRT
<213> ORGANISM: Homo sapiens

<400> SEQUENCE: 3

```
Cys Asp Leu Pro Gln Thr His Ser Leu Gly Ser Arg Arg Thr Leu Met
  1               5                  10                  15

Leu Leu Ala Gln Met Arg Arg Ile Ser Leu Phe Ser Cys Leu Lys Asp
             20                  25                  30

Arg His Asp Phe Gly Phe Pro Gln Glu Glu Phe Gly Asn Gln Phe Gln
         35                  40                  45

Lys Ala Glu Thr Ile Pro Val Leu His Glu Met Ile Gln Gln Ile Phe
     50                  55                  60

Asn Leu Phe Ser Thr Lys Asp Ser Ser Ala Ala Trp Asp Glu Thr Leu
 65                  70                  75                  80

Leu Asp Lys Phe Tyr Thr Glu Leu Tyr Gln Gln Leu Asn Asp Leu Glu
                 85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165
```

<210> SEQ ID NO 4
<211> LENGTH: 166
<212> TYPE: PRT
<213> ORGANISM: Homo sapiens

<400> SEQUENCE: 4

```
Cys Asp Leu Pro Glu Thr His Ser Leu Asp Asn Arg Arg Thr Leu Met
  1               5                  10                  15

Leu Leu Ala Gln Met Ser Arg Ile Ser Pro Ser Ser Cys Leu Met Asp
             20                  25                  30

Arg His Asp Phe Gly Phe Pro Gln Glu Glu Phe Asp Gly Asn Gln Phe
         35                  40                  45

Gln Lys Ala Pro Ala Ile Ser Val Leu His Glu Leu Ile Gln Gln Ile
     50                  55                  60

Phe Asn Leu Phe Thr Thr Lys Asp Ser Ser Ala Ala Trp Asp Glu Asp
```

```
                65                  70                  75                  80
Leu Leu Asp Lys Phe Cys Thr Glu Leu Tyr Gln Gln Leu Asn Asp Leu
                    85                  90                  95

Glu Ala Cys Val Met Gln Glu Arg Val Gly Glu Thr Pro Leu Met
                100                 105                 110

Asn Ala Asp Ser Ile Leu Ala Val Lys Lys Tyr Phe Arg Arg Ile Thr
                115                 120                 125

Leu Tyr Leu Thr Glu Lys Lys Tyr Ser Pro Cys Ala Trp Glu Val Val
            130                 135                 140

Arg Ala Glu Ile Met Arg Ser Leu Ser Leu Ser Thr Asn Leu Gln Glu
145                 150                 155                 160

Arg Leu Arg Arg Lys Glu
                165

<210> SEQ ID NO 5
<211> LENGTH: 166
<212> TYPE: PRT
<213> ORGANISM: Homo sapiens

<400> SEQUENCE: 5

Met Ser Tyr Asn Leu Leu Gly Phe Leu Gln Arg Ser Ser Asn Phe Gln
  1               5                  10                  15

Cys Gln Lys Leu Leu Trp Gln Leu Asn Gly Arg Leu Glu Tyr Cys Leu
                20                  25                  30

Lys Asp Arg Met Asn Phe Asp Ile Pro Glu Glu Ile Lys Gln Leu Gln
            35                  40                  45

Gln Phe Gln Lys Glu Asp Ala Ala Leu Thr Ile Tyr Glu Met Leu Gln
        50                  55                  60

Asn Ile Phe Ala Ile Phe Arg Gln Asp Ser Ser Ser Thr Gly Trp Asn
 65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
                100                 105                 110

Arg Gly Lys Leu Met Ser Ser Leu His Leu Lys Arg Tyr Tyr Gly Arg
            115                 120                 125

Ile Leu His Tyr Leu Lys Ala Lys Glu Tyr Ser His Cys Ala Trp Thr
        130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 6
<211> LENGTH: 174
<212> TYPE: PRT
<213> ORGANISM: Homo sapiens

<400> SEQUENCE: 6

Thr Pro Leu Gly Pro Ala Ser Ser Leu Pro Gln Ser Phe Leu Leu Lys
  1               5                  10                  15

Cys Leu Glu Gln Val Arg Lys Ile Gln Gly Asp Gly Ala Ala Leu Gln
                20                  25                  30

Glu Lys Leu Cys Ala Thr Tyr Lys Leu Cys His Pro Glu Glu Leu Val
            35                  40                  45

Leu Leu Gly His Ser Leu Gly Ile Pro Trp Ala Pro Leu Ser Ser Cys
        50                  55                  60
```

-continued

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170

<210> SEQ ID NO 7
<211> LENGTH: 332
<212> TYPE: PRT
<213> ORGANISM: Homo sapiens

<400> SEQUENCE: 7

Ser Pro Ala Pro Pro Ala Cys Asp Leu Arg Val Leu Ser Lys Leu Leu
1               5                   10                  15

Arg Asp Ser His Val Leu His Ser Arg Leu Ser Gln Cys Pro Glu Val
            20                  25                  30

His Pro Leu Pro Thr Pro Val Leu Leu Pro Ala Val Asp Phe Ser Leu
        35                  40                  45

Gly Glu Trp Lys Thr Gln Met Glu Glu Thr Lys Ala Gln Asp Ile Leu
    50                  55                  60

Gly Ala Val Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
            100                 105                 110

Pro Pro Gln Gly Arg Thr Thr Ala His Lys Asp Pro Asn Ala Ile Phe
        115                 120                 125

Leu Ser Phe Gln His Leu Leu Arg Gly Lys Val Arg Phe Leu Met Leu
    130                 135                 140

Val Gly Gly Ser Thr Leu Cys Val Arg Arg Ala Pro Pro Thr Thr Ala
145                 150                 155                 160

Val Pro Ser Arg Thr Ser Leu Val Leu Thr Leu Asn Glu Leu Pro Asn
                165                 170                 175

Arg Thr Ser Gly Leu Leu Glu Thr Asn Phe Thr Ala Ser Ala Arg Thr
            180                 185                 190

Thr Gly Ser Gly Leu Leu Lys Trp Gln Gln Gly Phe Arg Ala Lys Ile
        195                 200                 205

Pro Gly Leu Leu Asn Gln Thr Ser Arg Ser Leu Asp Gln Ile Pro Gly
    210                 215                 220

Tyr Leu Asn Arg Ile His Glu Leu Leu Asn Gly Thr Arg Gly Leu Phe
225                 230                 235                 240

Pro Gly Pro Ser Arg Arg Thr Leu Gly Ala Pro Asp Ile Ser Ser Gly
                245                 250                 255

Thr Ser Asp Thr Gly Ser Leu Pro Pro Asn Leu Gln Pro Gly Tyr Ser
            260                 265                 270

```
Pro Ser Pro Thr His Pro Pro Thr Gly Gly Tyr Thr Leu Phe Pro Leu
        275                 280                 285

Pro Pro Thr Leu Pro Thr Pro Val Val Gln Leu His Pro Leu Leu Pro
        290                 295                 300

Asp Pro Ser Ala Pro Thr Pro Thr Pro Thr Ser Pro Leu Leu Asn Thr
305                 310                 315                 320

Ser Tyr Thr His Ser Gln Asn Leu Ser Gln Glu Gly
            325                 330
```

<210> SEQ ID NO 8
<211> LENGTH: 127
<212> TYPE: PRT
<213> ORGANISM: Homo sapiens

<400> SEQUENCE: 8

```
Ala Pro Ala Arg Ser Pro Ser Pro Ser Thr Gln Pro Trp Glu His Val
1               5                   10                  15

Asn Ala Ile Gln Glu Ala Arg Arg Leu Leu Asn Leu Ser Arg Asp Thr
            20                  25                  30

Ala Ala Glu Met Asn Glu Thr Val Glu Val Ile Ser Glu Met Phe Asp
        35                  40                  45

Leu Gln Glu Pro Thr Cys Leu Gln Thr Arg Leu Glu Leu Tyr Lys Gln
    50                  55                  60

Gly Leu Arg Gly Ser Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Ile Ile Thr Phe Glu Ser Phe Lys Glu Asn Leu Lys Asp
            100                 105                 110

Phe Leu Leu Val Ile Pro Phe Asp Cys Trp Glu Pro Val Gln Glu
        115                 120                 125
```

<210> SEQ ID NO 9
<211> LENGTH: 133
<212> TYPE: PRT
<213> ORGANISM: Homo sapiens

<400> SEQUENCE: 9

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130
```

```
<210> SEQ ID NO 10
<211> LENGTH: 152
<212> TYPE: PRT
<213> ORGANISM: Homo sapiens

<400> SEQUENCE: 10

Met Ser Arg Leu Pro Val Leu Leu Leu Gln Leu Leu Val Arg Pro
1               5                   10                  15

Gly Leu Gln Ala Pro Met Thr Gln Thr Thr Pro Leu Lys Thr Ser Trp
            20                  25                  30

Val Asn Cys Ser Asn Met Ile Asp Glu Ile Ile Thr His Leu Lys Gln
                35                  40                  45

Pro Pro Leu Pro Leu Leu Asp Phe Asn Asn Leu Asn Gly Glu Asp Gln
        50                  55                  60

Asp Ile Leu Met Glu Asn Asn Leu Arg Arg Pro Asn Leu Glu Ala Phe
65                  70                  75                  80

Asn Arg Ala Val Lys Ser Leu Gln Asn Ala Ser Ala Ile Glu Ser Ile
                85                  90                  95

Leu Lys Asn Leu Leu Pro Cys Leu Pro Leu Ala Thr Ala Ala Pro Thr
            100                 105                 110

Arg His Pro Ile His Ile Lys Asp Gly Asp Trp Asn Glu Phe Arg Arg
        115                 120                 125

Lys Leu Thr Phe Tyr Leu Lys Thr Leu Glu Asn Ala Gln Ala Gln Gln
130                 135                 140

Thr Thr Leu Ser Leu Ala Ile Phe
145                 150

<210> SEQ ID NO 11
<211> LENGTH: 129
<212> TYPE: PRT
<213> ORGANISM: Homo sapiens

<400> SEQUENCE: 11

His Lys Cys Asp Ile Thr Leu Gln Glu Ile Ile Lys Thr Leu Asn Ser
1               5                   10                  15

Leu Thr Glu Gln Lys Thr Leu Cys Thr Glu Leu Thr Val Thr Asp Ile
            20                  25                  30

Phe Ala Ala Ser Lys Asn Thr Thr Glu Lys Glu Thr Phe Cys Arg Ala
        35                  40                  45

Ala Thr Val Leu Arg Gln Phe Tyr Ser His His Glu Lys Asp Thr Arg
    50                  55                  60

Cys Leu Gly Ala Thr Ala Gln Gln Phe His Arg His Lys Gln Leu Ile
65                  70                  75                  80

Arg Phe Leu Lys Arg Leu Asp Arg Asn Leu Trp Gly Leu Ala Gly Leu
                85                  90                  95

Asn Ser Cys Pro Val Lys Glu Ala Asn Gln Ser Thr Leu Glu Asn Phe
            100                 105                 110

Leu Glu Arg Leu Lys Thr Ile Met Arg Glu Lys Tyr Ser Lys Cys Ser
        115                 120                 125

Ser

<210> SEQ ID NO 12
<211> LENGTH: 134
<212> TYPE: PRT
<213> ORGANISM: Homo sapiens

<400> SEQUENCE: 12
```

```
Met Arg Met Leu Leu His Leu Ser Leu Leu Ala Leu Gly Ala Ala Tyr
1               5                   10                  15

Val Tyr Ala Ile Pro Thr Glu Ile Pro Thr Ser Ala Leu Val Lys Glu
                20                  25                  30

Thr Leu Ala Leu Leu Ser Thr His Arg Thr Leu Leu Ile Ala Asn Glu
            35                  40                  45

Thr Leu Arg Ile Pro Val Pro Val His Lys Asn His Gln Leu Cys Thr
        50                  55                  60

Glu Glu Ile Phe Gln Gly Ile Gly Thr Leu Glu Ser Gln Thr Val Gln
65                  70                  75                  80

Gly Gly Thr Val Glu Arg Leu Phe Lys Asn Leu Ser Leu Ile Lys Lys
                85                  90                  95

Tyr Ile Asp Gly Gln Lys Lys Lys Cys Gly Glu Glu Arg Arg Arg Val
                100                 105                 110

Asn Gln Phe Leu Asp Tyr Leu Gln Glu Phe Leu Gly Val Met Asn Thr
            115                 120                 125

Glu Trp Ile Ile Glu Ser
            130
```

<210> SEQ ID NO 13
<211> LENGTH: 212
<212> TYPE: PRT
<213> ORGANISM: Homo sapiens

<400> SEQUENCE: 13

```
Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
                20                  25                  30

Gly Glu Asp Ser Lys Asp Val Ala Ala Pro His Arg Gln Pro Leu Thr
            35                  40                  45

Ser Ser Glu Arg Ile Asp Lys Gln Ile Arg Tyr Ile Leu Asp Gly Ile
        50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
                100                 105                 110

Val Lys Ile Ile Thr Gly Leu Leu Glu Phe Glu Val Tyr Leu Glu Tyr
            115                 120                 125

Leu Gln Asn Arg Phe Glu Ser Ser Glu Glu Gln Ala Arg Ala Val Gln
130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
        195                 200                 205

Leu Arg Gln Met
    210
```

<210> SEQ ID NO 14
<211> LENGTH: 177

```
<212> TYPE: PRT
<213> ORGANISM: Homo sapiens

<400> SEQUENCE: 14

Met Phe His Val Ser Phe Arg Tyr Ile Phe Gly Leu Pro Pro Leu Ile
1               5                   10                  15

Leu Val Leu Leu Pro Val Ala Ser Ser Asp Cys Asp Ile Glu Gly Lys
            20                  25                  30

Asp Gly Lys Gln Tyr Glu Ser Val Leu Met Val Ser Ile Asp Gln Leu
        35                  40                  45

Leu Asp Ser Met Lys Glu Ile Gly Ser Asn Cys Leu Asn Asn Glu Phe
    50                  55                  60

Asn Phe Phe Lys Arg His Ile Cys Asp Ala Asn Lys Glu Gly Met Phe
65                  70                  75                  80

Leu Phe Arg Ala Ala Arg Lys Leu Arg Gln Phe Leu Lys Met Asn Ser
                85                  90                  95

Thr Gly Asp Phe Asp Leu His Leu Leu Lys Val Ser Glu Gly Thr Thr
            100                 105                 110

Ile Leu Leu Asn Cys Thr Gly Gln Val Lys Gly Arg Lys Pro Ala Ala
        115                 120                 125

Leu Gly Glu Ala Gln Pro Thr Lys Ser Leu Glu Glu Asn Lys Ser Leu
    130                 135                 140

Lys Glu Gln Lys Lys Leu Asn Asp Leu Cys Phe Leu Lys Arg Leu Leu
145                 150                 155                 160

Gln Glu Ile Lys Thr Cys Trp Asn Lys Ile Leu Met Gly Thr Lys Glu
                165                 170                 175

His

<210> SEQ ID NO 15
<211> LENGTH: 144
<212> TYPE: PRT
<213> ORGANISM: Homo sapiens

<400> SEQUENCE: 15

Met Leu Leu Ala Met Val Leu Thr Ser Ala Leu Leu Leu Cys Ser Val
1               5                   10                  15

Ala Gly Gln Gly Cys Pro Thr Leu Ala Gly Ile Leu Asp Ile Asn Phe
            20                  25                  30

Leu Ile Asn Lys Met Gln Glu Asp Pro Ala Ser Lys Cys His Cys Ser
        35                  40                  45

Ala Asn Val Thr Ser Cys Leu Cys Leu Gly Ile Pro Ser Asp Asn Cys
    50                  55                  60

Thr Arg Pro Cys Phe Ser Glu Arg Leu Ser Gln Met Thr Asn Thr Thr
65                  70                  75                  80

Met Gln Thr Arg Tyr Pro Leu Ile Phe Ser Arg Val Lys Lys Ser Val
                85                  90                  95

Glu Val Leu Lys Asn Asn Lys Cys Pro Tyr Phe Ser Cys Glu Gln Pro
            100                 105                 110

Cys Asn Gln Thr Thr Ala Gly Asn Ala Leu Thr Phe Leu Lys Ser Leu
        115                 120                 125

Leu Glu Ile Phe Gln Lys Glu Lys Met Arg Gly Met Arg Gly Lys Ile
    130                 135                 140

<210> SEQ ID NO 16
<211> LENGTH: 178
<212> TYPE: PRT
<213> ORGANISM: Homo sapiens
```

<400> SEQUENCE: 16

```
Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
            20                  25                  30

Phe Pro Gly Asn Leu Pro Asn Met Leu Arg Asp Leu Arg Asp Ala Phe
        35                  40                  45

Ser Arg Val Lys Thr Phe Phe Gln Met Lys Asp Gln Leu Asp Asn Leu
    50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Ala His Val Asn Ser Leu
            100                 105                 110

Gly Glu Asn Leu Lys Thr Leu Arg Leu Arg Leu Arg Arg Cys His Arg
        115                 120                 125

Phe Leu Pro Cys Glu Asn Lys Ser Lys Ala Val Glu Gln Val Lys Asn
    130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn
```

<210> SEQ ID NO 17
<211> LENGTH: 199
<212> TYPE: PRT
<213> ORGANISM: Homo sapiens

<400> SEQUENCE: 17

```
Met Asn Cys Val Cys Arg Leu Val Leu Val Val Leu Ser Leu Trp Pro
1               5                   10                  15

Asp Thr Ala Val Ala Pro Gly Pro Pro Pro Gly Pro Pro Arg Val Ser
            20                  25                  30

Pro Asp Pro Arg Ala Glu Leu Asp Ser Thr Val Leu Leu Thr Arg Ser
        35                  40                  45

Leu Leu Ala Asp Thr Arg Gln Leu Ala Ala Gln Leu Arg Asp Lys Phe
    50                  55                  60

Pro Ala Asp Gly Asp His Asn Leu Asp Ser Leu Pro Thr Leu Ala Met
65                  70                  75                  80

Ser Ala Gly Ala Leu Gly Ala Leu Gln Leu Pro Gly Val Leu Thr Arg
                85                  90                  95

Leu Arg Ala Asp Leu Leu Ser Tyr Leu Arg His Val Gln Trp Leu Arg
            100                 105                 110

Arg Ala Gly Gly Ser Ser Leu Lys Thr Leu Glu Pro Glu Leu Gly Thr
        115                 120                 125

Leu Gln Ala Arg Leu Asp Arg Leu Leu Arg Arg Leu Gln Leu Leu Met
    130                 135                 140

Ser Arg Leu Ala Leu Pro Gln Pro Pro Asp Pro Pro Ala Pro Pro Pro
145                 150                 155                 160

Leu Ala Pro Pro Ser Ser Ala Trp Gly Gly Ile Arg Ala Ala His Ala
                165                 170                 175

Ile Leu Gly Gly Leu His Leu Thr Leu Asp Trp Ala Val Arg Gly Leu
```

Leu Leu Leu Lys Thr Arg Leu
        195

<210> SEQ ID NO 18
<211> LENGTH: 219
<212> TYPE: PRT
<213> ORGANISM: Homo sapiens

<400> SEQUENCE: 18

Met Cys Pro Ala Arg Ser Leu Leu Val Ala Thr Leu Val Leu Leu
 1               5                  10                  15

Asp His Leu Ser Leu Ala Arg Asn Leu Pro Val Ala Thr Pro Asp Pro
                20                  25                  30

Gly Met Phe Pro Cys Leu His His Ser Gln Asn Leu Leu Arg Ala Val
            35                  40                  45

Ser Asn Met Leu Gln Lys Ala Arg Gln Thr Leu Glu Phe Tyr Pro Cys
        50                  55                  60

Thr Ser Glu Glu Ile Asp His Glu Asp Ile Thr Lys Asp Lys Thr Ser
65                  70                  75                  80

Thr Val Glu Ala Cys Leu Pro Leu Glu Leu Thr Lys Asn Glu Ser Cys
                85                  90                  95

Leu Asn Ser Arg Glu Thr Ser Phe Ile Thr Asn Gly Ser Cys Leu Ala
            100                 105                 110

Ser Arg Lys Thr Ser Phe Met Met Ala Leu Cys Leu Ser Ser Ile Tyr
        115                 120                 125

Glu Asp Leu Lys Met Tyr Gln Val Glu Phe Lys Thr Met Asn Ala Lys
    130                 135                 140

Leu Leu Met Asp Pro Lys Arg Gln Ile Phe Leu Asp Gln Asn Met Leu
145                 150                 155                 160

Ala Val Ile Asp Glu Leu Met Gln Ala Leu Asn Phe Asn Ser Glu Thr
                165                 170                 175

Val Pro Gln Lys Ser Ser Leu Glu Glu Pro Asp Phe Tyr Lys Thr Lys
            180                 185                 190

Ile Lys Leu Cys Ile Leu Leu His Ala Phe Arg Ile Arg Ala Val Thr
        195                 200                 205

Ile Asp Arg Val Thr Ser Tyr Leu Asn Ala Ser
    210                 215

<210> SEQ ID NO 19
<211> LENGTH: 132
<212> TYPE: PRT
<213> ORGANISM: Homo sapiens

<400> SEQUENCE: 19

Met Ala Leu Leu Leu Thr Thr Val Ile Ala Leu Thr Cys Leu Gly Gly
 1               5                  10                  15

Phe Ala Ser Pro Gly Pro Val Pro Pro Ser Thr Ala Leu Arg Glu Leu
                20                  25                  30

Ile Glu Glu Leu Val Asn Ile Thr Gln Asn Gln Lys Ala Pro Leu Cys
            35                  40                  45

Asn Gly Ser Met Val Trp Ser Ile Asn Leu Thr Ala Gly Met Tyr Cys
        50                  55                  60

Ala Ala Leu Glu Ser Leu Ile Asn Val Ser Gly Cys Ser Ala Ile Glu
65                  70                  75                  80

Lys Thr Gln Arg Met Leu Ser Gly Phe Cys Pro His Lys Val Ser Ala
                85                  90                  95

```
Gly Gln Phe Ser Ser Leu His Val Arg Asp Thr Lys Ile Glu Val Ala
                100                 105                 110

Gln Phe Val Lys Asp Leu Leu Leu His Leu Lys Lys Leu Phe Arg Glu
            115                 120                 125

Gly Arg Phe Asn
        130

<210> SEQ ID NO 20
<211> LENGTH: 114
<212> TYPE: PRT
<213> ORGANISM: Homo sapiens

<400> SEQUENCE: 20

Asn Trp Val Asn Val Ile Ser Asp Leu Lys Lys Ile Glu Asp Leu Ile
  1               5                  10                  15

Gln Ser Met His Ile Asp Ala Thr Leu Tyr Thr Glu Ser Asp Val His
             20                  25                  30

Pro Ser Cys Lys Val Thr Ala Met Lys Cys Phe Leu Leu Glu Leu Gln
         35                  40                  45

Val Ile Ser Leu Glu Ser Gly Asp Ala Ser Ile His Asp Thr Val Glu
     50                  55                  60

Asn Leu Ile Ile Leu Ala Asn Asn Ser Leu Ser Ser Asn Gly Asn Val
 65                  70                  75                  80

Thr Glu Ser Gly Cys Lys Glu Cys Glu Glu Leu Glu Glu Lys Asn Ile
                 85                  90                  95

Lys Glu Phe Leu Gln Ser Phe Val His Ile Val Gln Met Phe Ile Asn
            100                 105                 110

Thr Ser

<210> SEQ ID NO 21
<211> LENGTH: 252
<212> TYPE: PRT
<213> ORGANISM: Homo sapiens

<400> SEQUENCE: 21

Met Gly Val Leu Leu Thr Gln Arg Thr Leu Leu Ser Leu Val Leu Ala
  1               5                  10                  15

Leu Leu Phe Pro Ser Met Ala Ser Met Ala Ala Ile Gly Ser Cys Ser
             20                  25                  30

Lys Glu Tyr Arg Val Leu Leu Gly Gln Leu Gln Lys Gln Thr Asp Leu
         35                  40                  45

Met Gln Asp Thr Ser Arg Leu Leu Asp Pro Tyr Ile Arg Ile Gln Gly
     50                  55                  60

Leu Asp Val Pro Lys Leu Arg Glu His Cys Arg Glu Arg Pro Gly Ala
 65                  70                  75                  80

Phe Pro Ser Glu Glu Thr Leu Arg Gly Leu Gly Arg Arg Gly Phe Leu
                 85                  90                  95

Gln Thr Leu Asn Ala Thr Leu Gly Cys Val Leu His Arg Leu Ala Asp
            100                 105                 110

Leu Glu Gln Arg Leu Pro Lys Ala Gln Asp Leu Glu Arg Ser Gly Leu
            115                 120                 125

Asn Ile Glu Asp Leu Glu Lys Leu Gln Met Ala Arg Pro Asn Ile Leu
            130                 135                 140

Gly Leu Arg Asn Asn Ile Tyr Cys Met Ala Gln Leu Leu Asp Asn Ser
145                 150                 155                 160

Asp Thr Ala Glu Pro Thr Lys Ala Gly Arg Gly Ala Ser Gln Pro Pro
```

```
                    165                 170                 175
Thr Pro Thr Pro Ala Ser Asp Ala Phe Gln Arg Lys Leu Glu Gly Cys
            180                 185                 190

Arg Phe Leu His Gly Tyr His Arg Phe Met His Ser Val Gly Arg Val
        195                 200                 205

Phe Ser Lys Trp Gly Glu Ser Pro Asn Arg Ser Arg Arg His Ser Pro
    210                 215                 220

His Gln Ala Leu Arg Lys Gly Val Arg Thr Arg Pro Ser Arg Lys
225                 230                 235                 240

Gly Lys Arg Leu Met Thr Arg Gly Gln Leu Pro Arg
            245                 250

<210> SEQ ID NO 22
<211> LENGTH: 200
<212> TYPE: PRT
<213> ORGANISM: Homo sapiens

<400> SEQUENCE: 22

Met Ala Phe Thr Glu His Ser Pro Leu Thr Pro His Arg Arg Asp Leu
1               5                   10                  15

Cys Ser Arg Ser Ile Trp Leu Ala Arg Lys Ile Arg Ser Asp Leu Thr
            20                  25                  30

Ala Leu Thr Glu Ser Tyr Val Lys His Gln Gly Leu Asn Lys Asn Ile
        35                  40                  45

Asn Leu Asp Ser Ala Asp Gly Met Pro Val Ala Ser Thr Asp Gln Trp
    50                  55                  60

Ser Glu Leu Thr Glu Ala Glu Arg Leu Gln Glu Asn Leu Gln Ala Tyr
65                  70                  75                  80

Arg Thr Phe His Val Leu Leu Ala Arg Leu Leu Glu Asp Gln Gln Val
                85                  90                  95

His Phe Thr Pro Thr Glu Gly Asp Phe His Gln Ala Ile His Thr Leu
            100                 105                 110

Leu Leu Gln Val Ala Ala Phe Ala Tyr Gln Ile Glu Glu Leu Met Ile
        115                 120                 125

Leu Leu Glu Tyr Lys Ile Pro Arg Asn Glu Ala Asp Gly Met Pro Ile
    130                 135                 140

Asn Val Gly Asp Gly Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
                165                 170                 175

Arg Phe Ile Ser Ser His Gln Thr Gly Ile Pro Ala Arg Gly Ser His
            180                 185                 190

Tyr Ile Ala Asn Asn Lys Lys Met
        195                 200

<210> SEQ ID NO 23
<211> LENGTH: 181
<212> TYPE: PRT
<213> ORGANISM: Homo sapiens

<400> SEQUENCE: 23

Ser Pro Leu Pro Ile Thr Pro Val Asn Ala Thr Cys Ala Ile Arg His
1               5                   10                  15

Pro Cys His Asn Asn Leu Met Asn Gln Ile Arg Ser Gln Leu Ala Gln
            20                  25                  30

Leu Asn Gly Ser Ala Asn Ala Leu Phe Ile Leu Tyr Tyr Thr Ala Gln
        35                  40                  45
```

```
Gly Glu Pro Phe Pro Asn Asn Leu Asp Lys Leu Cys Gly Pro Asn Val
        50                  55                  60

Thr Asp Phe Pro Pro Phe His Ala Asn Gly Thr Glu Lys Ala Lys Leu
 65                  70                  75                  80

Val Glu Leu Tyr Arg Ile Val Val Tyr Leu Gly Thr Ser Leu Gly Asn
                 85                  90                  95

Ile Thr Arg Asp Gln Lys Ile Leu Asn Pro Ser Ala Leu Ser Leu His
            100                 105                 110

Ser Lys Leu Asn Ala Thr Ala Asp Ile Leu Arg Gly Leu Leu Ser Asn
            115                 120                 125

Val Leu Cys Arg Leu Cys Ser Lys Tyr His Val Gly His Val Asp Val
        130                 135                 140

Thr Tyr Gly Pro Pro Asp Thr Ser Gly Lys Asp Val Phe Gln Lys Lys
145                 150                 155                 160

Lys Leu Gly Cys Gln Leu Leu Gly Lys Tyr Lys Gln Ile Ile Ala Val
                165                 170                 175

Leu Ala Gln Ala Phe
            180

<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence:PCR Primer

<400> SEQUENCE: 24
catatgttcc caaccattcc cttatccag                                    29

<210> SEQ ID NO 25
<211> LENGTH: 33
<212> TYPE: DNA
<213> ORGANISM: Artificial Sequence
<220> FEATURE:
<223> OTHER INFORMATION: Description of Artificial Sequence:PCR Primer

<400> SEQUENCE: 25
gggggatcct cactagaagc cacagctgcc ctc                               33

<210> SEQ ID NO 26
<211> LENGTH: 39
<212> TYPE: DNA
<213> ORGANISM: Artificial Sequence
<220> FEATURE:
<223> OTHER INFORMATION: Description of Artificial Sequence:PCR Primer

<400> SEQUENCE: 26
ccccggatcc gccaccatgg atctctggca gctgctgtt                         39

<210> SEQ ID NO 27
<211> LENGTH: 40
<212> TYPE: DNA
<213> ORGANISM: Artificial Sequence
<220> FEATURE:
<223> OTHER INFORMATION: Description of Artificial Sequence:PCR Primer

<400> SEQUENCE: 27
ccccgtcgac tctagagcta ttaaatacgt agctcttggg                        40

<210> SEQ ID NO 28
<211> LENGTH: 32
<212> TYPE: DNA
```

<213> ORGANISM: Artificial Sequence
<220> FEATURE:
<223> OTHER INFORMATION: Description of Artificial Sequence:PCR Primer

<400> SEQUENCE: 28
cgcggatccg attagaatcc acagctcccc tc                                    32

<210> SEQ ID NO 29
<211> LENGTH: 66
<212> TYPE: DNA
<213> ORGANISM: Artificial Sequence
<220> FEATURE:
<223> OTHER INFORMATION: Description of Artificial Sequence:PCR Primer

<400> SEQUENCE: 29 cccctctag acatatgaag aagaacatcg cattcctgct ggcatctatg ttcgttttct       60
ctatcg                                                                 66

<210> SEQ ID NO 30
<211> LENGTH: 65
<212> TYPE: DNA
<213> ORGANISM: Artificial Sequence
<220> FEATURE:
<223> OTHER INFORMATION: Description of Artificial Sequence:PCR Primer

<400> SEQUENCE: 30
gcatctatgt tcgttttctc tatcgctacc aacgcttacg cattcccaac cattccctta      60
tccag                                                                  65

<210> SEQ ID NO 31
<211> LENGTH: 62
<212> TYPE: DNA
<213> ORGANISM: Artificial Sequence
<220> FEATURE:
<223> OTHER INFORMATION: Description of Artificial Sequence:PCR Primer

<400> SEQUENCE: 31
gcagtggcac tggctggttt cgctaccgta gcgcaggcct cccaaccat tcccttatcc       60 ag                                                                     62

<210> SEQ ID NO 32
<211> LENGTH: 59
<212> TYPE: DNA
<213> ORGANISM: Artificial Sequence
<220> FEATURE:
<223> OTHER INFORMATION: Description of Artificial Sequence:PCR Primer

<400> SEQUENCE: 32
ccccgtcgac acatatgaag aagacagcta tcgcgattgc agtggcactg gctggtttc       59

<210> SEQ ID NO 33
<211> LENGTH: 36
<212> TYPE: DNA
<213> ORGANISM: Artificial Sequence
<220> FEATURE:
<223> OTHER INFORMATION: Description of Artificial Sequence:PCR Primer

<400> SEQUENCE: 33
ctgcttgaag atctgcccac accgggggct gccatc                                36

<210> SEQ ID NO 34
<211> LENGTH: 24
<212> TYPE: DNA
<213> ORGANISM: Artificial Sequence
<220> FEATURE:

-continued

<223> OTHER INFORMATION: Description of Artificial Sequence:PCR Primer

<400> SEQUENCE: 34
gtagcgcagg ccttcccaac catt                                              24

<210> SEQ ID NO 35
<211> LENGTH: 39
<212> TYPE: DNA
<213> ORGANISM: Artificial Sequence
<220> FEATURE:
<223> OTHER INFORMATION: Description of Artificial Sequence:PCR Primer

<400> SEQUENCE: 35
ctgcttgaag atctgcccag tccgggggca gccatcttc                              39

<210> SEQ ID NO 36
<211> LENGTH: 51
<212> TYPE: DNA
<213> ORGANISM: Artificial Sequence
<220> FEATURE:
<223> OTHER INFORMATION: Description of Artificial Sequence:PCR Primer

<400> SEQUENCE: 36
gggcagatct tcaagcagac ctacagcaag ttcgactgca actcacacaa c                51

<210> SEQ ID NO 37
<211> LENGTH: 34
<212> TYPE: DNA
<213> ORGANISM: Artificial Sequence
<220> FEATURE:
<223> OTHER INFORMATION: Description of Artificial Sequence:PCR Primer

<400> SEQUENCE: 37
cgcggtaccc gggatccgat tagaatccac agct                                   34

<210> SEQ ID NO 38
<211> LENGTH: 36
<212> TYPE: DNA
<213> ORGANISM: Artificial Sequence
<220> FEATURE:
<223> OTHER INFORMATION: Description of Artificial Sequence:PCR Primer

<400> SEQUENCE: 38
gggcagatct tcaagcagac ctactgcaag ttcgac                                 36

<210> SEQ ID NO 39
<211> LENGTH: 42
<212> TYPE: DNA
<213> ORGANISM: Artificial Sequence
<220> FEATURE:
<223> OTHER INFORMATION: Description of Artificial Sequence:PCR Primer

<400> SEQUENCE: 39
cgcggtaccg gatccttagc agaagccaca gctgccctcc ac                          42

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence:PCR Primer

<400> SEQUENCE: 40
gtagcgcagg ccttcccaac catt                                              24

<210> SEQ ID NO 41

```
<211> LENGTH: 40
<212> TYPE: DNA
<213> ORGANISM: Artificial Sequence
<220> FEATURE:
<223> OTHER INFORMATION: Description of Artificial Sequence:PCR Primer

<400> SEQUENCE: 41
ccccgtcgac tctagagcca ttagatacaa agctcttggg                          40
```